(12) United States Patent
Silverstein

(10) Patent No.: US 9,907,513 B2
(45) Date of Patent: *Mar. 6, 2018

(54) PERCUTANEOUS MAGNETIC GASTROSTOMY

(71) Applicant: Bard Access Systems, Inc., Salt Lake City, UT (US)

(72) Inventor: Fred E. Silverstein, Seattle, WA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 668 days.

This patent is subject to a terminal disclaimer.

(21) Appl. No.: 13/887,166

(22) Filed: May 3, 2013

(65) Prior Publication Data

US 2013/0317338 A1    Nov. 28, 2013

Related U.S. Application Data

(63) Continuation of application No. 12/575,456, filed on Oct. 7, 2009, now Pat. No. 8,437,833.

(Continued)

(51) Int. Cl.
*A61B 5/05* (2006.01)
*A61B 5/00* (2006.01)
(Continued)

(52) U.S. Cl.
CPC .............. *A61B 5/742* (2013.01); *A61B 5/06* (2013.01); *A61B 5/061* (2013.01); *A61B 5/062* (2013.01); *A61B 5/7405* (2013.01); *A61B 17/3415* (2013.01); *A61B 34/20* (2016.02); *A61M 25/0127* (2013.01); *A61B 17/3478* (2013.01); *A61B 2017/003* (2013.01); *A61B 2017/00477* (2013.01); *A61B 2017/00876* (2013.01); *A61B 2017/3407* (2013.01);
(Continued)

(58) Field of Classification Search
CPC ......... A61B 5/7405; A61B 5/06; A61B 5/062; A61B 5/061; A61B 17/3478; A61B 2034/2051
USPC ........................................ 600/407, 424, 427
See application file for complete search history.

(56) References Cited

U.S. PATENT DOCUMENTS 3,133,244 A    5/1964   Wojtulewicz
3,297,020 A    1/1967   Mathiesen
(Continued)

FOREIGN PATENT DOCUMENTS

AU         642647        11/1990
AU      1860597 B2        6/1999
(Continued)

OTHER PUBLICATIONS

Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.

(Continued)

*Primary Examiner* — Joel Lamprecht
(74) *Attorney, Agent, or Firm* — Rutan & Tucker, LLP

(57) ABSTRACT

A medical device system includes a needle having a tip including a permanent magnet, and a magnet sensing device including a plurality of sensors configured to detect the magnetic field of the permanent magnet. The magnet sensing device is operable to localize a position of the permanent magnet relative to the magnet sensing device and to indicate a path of the needle on a display.

7 Claims, 32 Drawing Sheets

Light is poorly seen or diffused

Related U.S. Application Data

(60) Provisional application No. 61/103,419, filed on Oct. 7, 2008.

(51) Int. Cl.
| | | |
|---|---|---|
| *A61B 5/06* | (2006.01) | |
| *A61B 17/34* | (2006.01) | |
| *A61M 25/01* | (2006.01) | |
| *A61B 34/20* | (2016.01) | |
| *A61B 17/00* | (2006.01) | |
| *A61M 25/10* | (2013.01) | |
| *A61M 25/06* | (2006.01) | |
| *A61B 90/00* | (2016.01) | |
| *A61B 34/10* | (2016.01) | |

(52) U.S. Cl.
CPC . *A61B 2034/107* (2016.02); *A61B 2034/2051* (2016.02); *A61B 2090/373* (2016.02); *A61B 2090/3954* (2016.02); *A61M 25/10* (2013.01); *A61M 2025/0681* (2013.01)

(56) References Cited

U.S. PATENT DOCUMENTS

| | | |
|---|---|---|
| 3,625,200 A | 12/1971 | Muller |
| 3,674,014 A | 7/1972 | Tillander et al. |
| 3,817,241 A | 6/1974 | Grausz |
| 3,847,157 A | 11/1974 | Caillouette et al. |
| 3,868,565 A | 2/1975 | Kuipers |
| 3,896,373 A | 7/1975 | Zelby |
| 3,902,501 A | 9/1975 | Citron et al. |
| 3,986,373 A | 10/1976 | Goodlaxson |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder et al. |
| 4,173,228 A | 11/1979 | Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,327,723 A | 5/1982 | Frankhouser |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,417,886 A | 11/1983 | Frankhouser et al. |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,587,975 A | 5/1986 | Salo et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,660,571 A | 4/1987 | Hess et al. |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner et al. |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,790,809 A | 12/1988 | Kuntz |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,836,214 A | 6/1989 | Sramek |
| 4,840,182 A | 6/1989 | Carlson |
| 4,840,622 A | 6/1989 | Hardy |
| 4,841,977 A | 6/1989 | Griffith et al. |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,873,987 A | 10/1989 | Djordjevich et al. |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,917,669 A | 4/1990 | Bonaldo |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |

(56) References Cited

U.S. PATENT DOCUMENTS

| | | |
|---|---|---|
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,184,601 A | 2/1993 | Putman |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer et al. |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout et al. |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A | 11/1994 | Stoy et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada et al. |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |

(56) References Cited

U.S. PATENT DOCUMENTS

| | | |
|---|---|---|
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman et al. |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A | 7/1998 | Thome et al. |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer et al. |
| 5,792,055 A | 8/1998 | McKinnon et al. |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,842,998 A | 12/1998 | Gopakumaran et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,931,863 A | 8/1999 | Griffin, III et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,951,472 A | 9/1999 | Van Vaals et al. |
| 5,951,598 A | 9/1999 | Bishay et al. |

(56) References Cited

U.S. PATENT DOCUMENTS

| | | |
|---|---|---|
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,971,933 A | 10/1999 | Gopakumaran et al. |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,022,342 A | 2/2000 | Mukherjee |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,059,718 A | 5/2000 | Taniguchi et al. |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,081,737 A | 6/2000 | Shah |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,107,699 A | 8/2000 | Swanson |
| 6,112,111 A | 8/2000 | Glantz |
| 6,112,115 A | 8/2000 | Feldman et al. |
| 6,113,504 A | 9/2000 | Kuesters |
| 6,115,624 A | 9/2000 | Lewis et al. |
| 6,120,445 A | 9/2000 | Grunwald |
| 6,122,538 A | 9/2000 | Sliwa, Jr. et al. |
| 6,128,174 A | 10/2000 | Ritter et al. |
| 6,129,668 A | 10/2000 | Haynor et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,139,540 A | 10/2000 | Rost et al. |
| 6,144,300 A | 11/2000 | Dames et al. |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,165,977 A | 12/2000 | Mochly-Rosen |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,187,744 B1 | 2/2001 | Rooney |
| 6,190,370 B1 | 2/2001 | Tsui |
| 6,191,136 B1 | 2/2001 | Marban |
| 6,193,743 B1 | 2/2001 | Brayton et al. |
| 6,197,001 B1 | 3/2001 | Wilson et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,216,027 B1 | 4/2001 | Willis et al. |
| 6,216,028 B1 | 4/2001 | Haynor et al. |
| 6,216,029 B1 | 4/2001 | Paltieli |
| 6,223,087 B1 | 4/2001 | Williams |
| 6,226,547 B1 | 5/2001 | Lockhart et al. |
| 6,230,042 B1 | 5/2001 | Slettenmark |
| 6,230,046 B1 | 5/2001 | Crane et al. |
| 6,231,518 B1 | 5/2001 | Grabek et al. |
| 6,233,476 B1 | 5/2001 | Strommer et al. |
| 6,233,994 B1 | 5/2001 | Roy et al. |
| 6,236,883 B1 | 5/2001 | Ciaccio et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,253,770 B1 | 7/2001 | Acker et al. |
| 6,258,035 B1 | 7/2001 | Hoeksel et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,270,493 B1 | 8/2001 | Lalonde et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,287,260 B1 | 9/2001 | Hascoet et al. |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,306,105 B1 | 10/2001 | Rooney et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames et al. |
| 6,323,770 B1 | 11/2001 | Dames et al. |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames et al. |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |

(56) References Cited

U.S. PATENT DOCUMENTS

| | | |
|---|---|---|
| 6,350,160 B1 | 2/2002 | Feuersanger et al. |
| 6,352,363 B1 | 3/2002 | Munger et al. |
| 6,354,999 B1 | 3/2002 | Dgany et al. |
| 6,355,026 B1 | 3/2002 | Mick |
| 6,356,791 B1 | 3/2002 | Westlund et al. |
| 6,360,123 B1 | 3/2002 | Kimchi et al. |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames et al. |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,398,738 B1 | 6/2002 | Millar |
| 6,401,723 B1 | 6/2002 | Garibaldi et al. |
| 6,406,422 B1 | 6/2002 | Landesberg |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,456,874 B1 | 9/2002 | Hafer et al. |
| 6,459,919 B1 | 10/2002 | Lys et al. |
| 6,463,121 B1 | 10/2002 | Milnes |
| 6,466,815 B1 | 10/2002 | Saito et al. |
| 6,471,656 B1 | 10/2002 | Shalman et al. |
| 6,471,658 B1 | 10/2002 | Daniels et al. |
| 6,471,700 B1 | 10/2002 | Burbank et al. |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari et al. |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,494,832 B1 | 12/2002 | Feldman et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,506,159 B2 | 1/2003 | Hascoet et al. |
| 6,507,751 B2 | 1/2003 | Blume et al. |
| 6,508,802 B1 | 1/2003 | Rosengart et al. |
| 6,511,413 B2 | 1/2003 | Landesberg |
| 6,512,958 B1 | 1/2003 | Swoyer et al. |
| 6,514,226 B1 | 2/2003 | Levin et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith et al. |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,505 B1 | 11/2003 | Tsugita |
| 6,652,506 B2 | 11/2003 | Bowe et al. |
| 6,660,024 B1 | 12/2003 | Flaherty et al. |
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |

(56) References Cited

U.S. PATENT DOCUMENTS

| | | |
|---|---|---|
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito et al. |
| 6,754,596 B2 | 6/2004 | Ashe |
| 6,755,789 B2 | 6/2004 | Stringer et al. |
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke et al. |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop et al. |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,986,744 B1 | 1/2006 | Krivitski |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,048,733 B2 | 5/2006 | Hartley et al. |
| 7,054,228 B1 | 5/2006 | Hickling |
| 7,065,403 B1 | 6/2006 | Mouchawar et al. |
| 7,066,914 B2 | 6/2006 | Andersen |
| 7,066,924 B1 | 6/2006 | Garibaldi et al. |
| 7,069,072 B2 | 6/2006 | Jansen et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,059 B2 | 8/2006 | Geddes et al. |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,112,197 B2 | 9/2006 | Hartley et al. |
| 7,128,734 B1 | 10/2006 | Wilson et al. |
| 7,132,804 B2 | 11/2006 | Lys et al. |
| 7,137,976 B2 | 11/2006 | Ritter et al. |
| 7,141,019 B2 | 11/2006 | Pearlman |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,169,109 B2 | 1/2007 | Jansen et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,189,205 B2 | 3/2007 | McMorrow et al. |
| 7,189,208 B1 | 3/2007 | Beatty et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,236,820 B2 | 6/2007 | Mabary et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |

(56) References Cited

U.S. PATENT DOCUMENTS

| | | |
|---|---|---|
| 7,252,633 B2 | 8/2007 | Obata et al. |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,300,430 B2 | 11/2007 | Wilson et al. |
| 7,302,288 B1 | 11/2007 | Schellenberg |
| 7,308,296 B2 | 12/2007 | Lys et al. |
| 7,310,150 B2 | 12/2007 | Guillermo et al. |
| 7,311,702 B2 | 12/2007 | Tallarida et al. |
| 7,321,228 B2 | 1/2008 | Govari |
| 7,326,241 B2 | 2/2008 | Jang |
| 7,327,872 B2 | 2/2008 | Vaillant et al. |
| 7,342,058 B2 | 3/2008 | Peppmoller et al. |
| 7,349,732 B1 | 3/2008 | Kil et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,381,204 B2 | 6/2008 | Wilson et al. |
| 7,382,949 B2 | 6/2008 | Bouma et al. |
| 7,384,407 B2 | 6/2008 | Rodriguez et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| 7,454,244 B2 | 11/2008 | Kassab et al. |
| D585,556 S | 1/2009 | Kosaku |
| 7,479,141 B2 | 1/2009 | Kleen et al. |
| 7,519,424 B2 | 4/2009 | Dennis et al. |
| 7,529,584 B2 | 5/2009 | Laske et al. |
| 7,534,223 B2 | 5/2009 | Boutilette et al. |
| 7,538,859 B2 | 5/2009 | Tearney et al. |
| 7,543,239 B2 | 6/2009 | Viswanathan et al. |
| 7,546,158 B2 | 6/2009 | Allison et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,606,615 B2 | 10/2009 | Makower et al. |
| 7,616,992 B2 | 11/2009 | Dennis et al. |
| 7,627,376 B2 | 12/2009 | Dennis et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,660,623 B2 | 2/2010 | Hunter et al. |
| 7,665,893 B2 | 2/2010 | Buchalter |
| 7,668,583 B2 | 2/2010 | Fegert et al. |
| 7,697,972 B2 | 4/2010 | Verard et al. |
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,828,528 B2 | 11/2010 | Estes et al. |
| 7,831,294 B2 | 11/2010 | Viswanathan |
| 7,833,168 B2 | 11/2010 | Taylor et al. |
| 7,833,214 B2 | 11/2010 | Wilson et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,873,402 B2 | 1/2011 | Shachar |
| 7,909,815 B2 | 3/2011 | Whitmore, III et al. |
| 7,931,596 B2 | 4/2011 | Rachlin et al. |
| 7,947,040 B2 | 5/2011 | Davies et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,057,394 B2 | 11/2011 | Dala-Krishna |
| 8,060,185 B2 | 11/2011 | Hunter et al. |
| 8,078,274 B2 | 12/2011 | Kassab |
| 8,078,279 B2 | 12/2011 | Dennis et al. |
| 8,082,032 B2 | 12/2011 | Kassab et al. |
| 8,088,072 B2 | 1/2012 | Munrow et al. |
| 8,090,430 B2 | 1/2012 | Makower et al. |
| 8,099,161 B2 | 1/2012 | Kassab |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |
| 8,150,522 B2 | 4/2012 | Echauz et al. |
| 8,152,724 B2 | 4/2012 | Ridley et al. |
| 8,204,582 B2 | 6/2012 | Zantos et al. |
| 8,214,018 B2 | 7/2012 | Markowitz et al. |
| 8,221,402 B2 | 7/2012 | Francischelli et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,326,419 B2 | 12/2012 | Rosenberg et al. |
| 8,340,751 B2 | 12/2012 | Markowitz et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,616 B2 | 3/2013 | Verard et al. |
| 8,409,103 B2 | 4/2013 | Grunwald et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| D684,265 S | 6/2013 | Cadera |
| 8,456,182 B2 | 6/2013 | Bar-Tal et al. |
| 8,478,382 B2 | 7/2013 | Burnside et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,527,036 B2 | 9/2013 | Jalde et al. |
| 8,538,509 B2 | 9/2013 | Harlev et al. |
| 8,644,907 B2 | 2/2014 | Hartmann et al. |
| 8,690,776 B2 | 4/2014 | Razzaque et al. |
| 8,734,440 B2 | 5/2014 | Wu |
| 8,774,907 B2 | 7/2014 | Rothenberg |
| 8,781,555 B2 | 7/2014 | Burnside et al. |
| 8,784,336 B2 | 7/2014 | Bown et al. |
| 8,801,693 B2 | 8/2014 | He et al. |
| 8,849,382 B2 | 9/2014 | Cox et al. |
| 8,858,455 B2 | 10/2014 | Rothenberg |
| 8,934,961 B2 | 1/2015 | Lakin et al. |
| 9,125,578 B2 | 9/2015 | Grunwald |
| 9,339,206 B2 | 5/2016 | Grunwald |
| 9,456,766 B2 | 10/2016 | Cox et al. |
| 9,492,097 B2 | 11/2016 | Wilkes et al. |
| 9,521,961 B2 | 12/2016 | Silverstein et al. |

(56) References Cited

U.S. PATENT DOCUMENTS

| | | |
|---|---|---|
| 9,526,440 B2 | 12/2016 | Burnside et al. |
| 9,532,724 B2 | 1/2017 | Grunwald |
| 9,554,716 B2 | 1/2017 | Burnside et al. |
| 9,636,031 B2 | 5/2017 | Cox |
| 9,642,986 B2 | 5/2017 | Beasley |
| 9,649,048 B2 | 5/2017 | Cox et al. |
| 9,681,823 B2 | 6/2017 | Messerly et al. |
| 9,833,169 B2 | 12/2017 | Rothenberg |
| 9,839,372 B2 | 12/2017 | Bukhman et al. |
| 2002/0010392 A1 | 1/2002 | Desai |
| 2002/0016549 A1 | 2/2002 | Mejia |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0049488 A1 | 4/2002 | Boneau |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0129952 A1 | 9/2002 | Matsudate et al. |
| 2002/0133079 A1 | 9/2002 | Sandhu |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0165537 A1 | 11/2002 | Kelley et al. |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013966 A1 | 1/2003 | Barnes et al. |
| 2003/0013986 A1 | 1/2003 | Saadat |
| 2003/0018251 A1 | 1/2003 | Solomon |
| 2003/0036696 A1 | 2/2003 | Willis et al. |
| 2003/0040671 A1 | 2/2003 | Somogyi et al. |
| 2003/0040743 A1 | 2/2003 | Cosman et al. |
| 2003/0072805 A1 | 4/2003 | Miyazawa et al. |
| 2003/0073901 A1 | 4/2003 | Simon et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |
| 2003/0139661 A1 | 7/2003 | Kimchy et al. |
| 2003/0149328 A1 | 8/2003 | Elliott et al. |
| 2003/0149368 A1 | 8/2003 | Hennemann et al. |
| 2003/0152290 A1 | 8/2003 | Odell |
| 2003/0160721 A1 | 8/2003 | Gilboa et al. |
| 2003/0163037 A1 | 8/2003 | Bladen et al. |
| 2003/0163142 A1 | 8/2003 | Paltieli et al. |
| 2003/0171691 A1 | 9/2003 | Casscells et al. |
| 2003/0173953 A1 | 9/2003 | Ashe |
| 2003/0181892 A1 | 9/2003 | Pajunk et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2003/0236445 A1 | 12/2003 | Couvillon |
| 2004/0010189 A1 | 1/2004 | van Sloun et al. |
| 2004/0015070 A1 | 1/2004 | Liang et al. |
| 2004/0024301 A1 | 2/2004 | Hockett et al. |
| 2004/0030319 A1 | 2/2004 | Korkor et al. |
| 2004/0054278 A1 | 3/2004 | Kimchy et al. |
| 2004/0059237 A1 | 3/2004 | Narayan et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0092962 A1 | 5/2004 | Thornton et al. |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1 | 7/2004 | Le et al. |
| 2004/0138564 A1 | 7/2004 | Hwang et al. |
| 2004/0138570 A1 | 7/2004 | Nita et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1 | 11/2004 | Frankowski et al. |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |

(56) References Cited

U.S. PATENT DOCUMENTS

| | | |
|---|---|---|
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2006/0009759 A1 | 1/2006 | Chrisitian et al. |
| 2006/0015003 A1 | 1/2006 | Moaddes et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0068074 A1 | 3/2006 | Stefandl |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0122514 A1 | 6/2006 | Byrd et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0206037 A1 | 9/2006 | Braxton |
| 2006/0211944 A1 | 9/2006 | Mauge et al. |
| 2006/0217655 A1 | 9/2006 | Vitullo et al. |
| 2006/0224188 A1 | 10/2006 | Libbus et al. |
| 2006/0241432 A1 | 10/2006 | Herline et al. |
| 2006/0247746 A1 | 11/2006 | Danek et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0032746 A1 | 2/2007 | Sell |
| 2007/0038113 A1 | 2/2007 | Oonuki et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0027320 A1 | 1/2008 | Bolorforosh et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0125772 A1 | 5/2008 | Stone et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255475 A1 | 10/2008 | Kondrosky et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0082661 A1 | 3/2009 | Saladin et al. |
| 2009/0084382 A1 | 4/2009 | Jalde et al. |
| 2009/0101577 A1 | 4/2009 | Fulkerson et al. |
| 2009/0118612 A1 | 5/2009 | Grunwald et al. |

(56) References Cited

U.S. PATENT DOCUMENTS

| | | |
|---|---|---|
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0203989 A1 | 8/2009 | Burnside et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0253976 A1 | 10/2009 | Harlev et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0297441 A1 | 12/2009 | Canham et al. |
| 2010/0004543 A1 | 1/2010 | Ahlund et al. |
| 2010/0004547 A1 | 1/2010 | Scholz et al. |
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0168557 A1 | 7/2010 | Deno et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1 | 8/2011 | Grunwald |
| 2011/0196255 A1 | 8/2011 | Kassab |
| 2011/0237935 A1 | 9/2011 | Kalpin et al. |
| 2011/0245659 A1 | 10/2011 | Ma et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0295108 A1 | 12/2011 | Cox et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0035460 A1 | 2/2012 | Stangenes et al. |
| 2012/0046562 A1 | 2/2012 | Powers et al. |
| 2012/0059249 A1 | 3/2012 | Verard et al. |
| 2012/0059270 A1 | 3/2012 | Grunwald |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0220854 A1 | 8/2012 | Messerly et al. |
| 2012/0283582 A1 | 11/2012 | Mahapatra et al. |
| 2012/0296200 A1 | 11/2012 | Shachar et al. |
| 2012/0310052 A1 | 12/2012 | Mahapatra et al. |
| 2012/0310066 A1 | 12/2012 | Shachar et al. |
| 2012/0316440 A1 | 12/2012 | Munrow et al. |
| 2013/0006102 A1 | 1/2013 | Wilkes et al. |
| 2013/0018248 A1 | 1/2013 | Hurezan |
| 2013/0035590 A1 | 2/2013 | Ma et al. |
| 2013/0041269 A1 | 2/2013 | Stahmann et al. |
| 2013/0060116 A1 | 3/2013 | Messerly et al. |
| 2013/0085416 A1 | 4/2013 | Mest |
| 2013/0102890 A1 | 4/2013 | Dib |
| 2013/0123597 A1 | 5/2013 | Rothenberg |
| 2013/0169272 A1 | 7/2013 | Eichler et al. |
| 2013/0217999 A1 | 8/2013 | Burnside et al. |
| 2013/0245434 A1 | 9/2013 | Messerly et al. |
| 2013/0296691 A1 | 11/2013 | Ashe |
| 2013/0303896 A1 | 11/2013 | Kalpin et al. |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0031674 A1 | 1/2014 | Newman et al. |
| 2014/0046261 A1 | 2/2014 | Newman et al. |
| 2014/0094694 A1 | 4/2014 | Moctezuma De La Barrera |
| 2014/0094768 A1 | 4/2014 | Stangenes et al. |
| 2014/0107475 A1 | 4/2014 | Cox et al. |
| 2014/0163356 A2 | 6/2014 | Burnside et al. |
| 2014/0180074 A1 | 6/2014 | Green et al. |
| 2014/0187990 A1 | 7/2014 | Banet et al. |
| 2014/0188133 A1 | 7/2014 | Misener |
| 2014/0228689 A1 | 8/2014 | Ishikawa et al. |
| 2014/0243659 A1 | 8/2014 | Rothenberg |
| 2014/0249505 A1 | 9/2014 | Bukhman |
| 2014/0257080 A1 | 9/2014 | Dunbar et al. |
| 2014/0275957 A1 | 9/2014 | Lupotti |
| 2014/0275990 A1 | 9/2014 | Hagy et al. |
| 2014/0303492 A1 | 10/2014 | Burnside et al. |

(56) References Cited

U.S. PATENT DOCUMENTS

| | | |
|---|---|---|
| 2014/0309624 A1 | 10/2014 | Bown et al. |
| 2014/0343398 A1 | 11/2014 | He et al. |
| 2015/0005621 A1 | 1/2015 | Liu |
| 2015/0018701 A1 | 1/2015 | Cox et al. |
| 2015/0025402 A1 | 1/2015 | Rothenberg |
| 2015/0051489 A1 | 2/2015 | Caluser et al. |
| 2015/0080716 A1 | 3/2015 | Powers et al. |
| 2015/0216446 A1 | 8/2015 | Bukhman et al. |
| 2015/0297114 A1 | 10/2015 | Cox et al. |
| 2016/0374589 A1 | 12/2016 | Misener et al. |
| 2017/0000367 A1 | 1/2017 | Grunwald |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0151022 A1 | 6/2017 | Jascob et al. |
| 2017/0231700 A1 | 8/2017 | Cox et al. |
| 2017/0281029 A1 | 10/2017 | Messerly et al. |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006202149 | 6/2006 |
| AU | 2006904933 | 9/2006 |
| AU | 2006283022 B2 | 2/2012 |
| CA | 2420676 | 2/2002 |
| CA | 2619909 C | 1/2014 |
| CN | 2031655 U | 2/1989 |
| CN | 1672649 A | 9/2005 |
| CN | 1913833 A | 2/2007 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103189009 A | 7/2013 |
| DE | 4319033 C1 | 6/1994 |
| EP | 0359697 | 3/1990 |
| EP | 0362821 | 4/1990 |
| EP | 0399536 A1 | 11/1990 |
| EP | 0823261 A2 | 2/1998 |
| EP | 0928976 A2 | 7/1999 |
| EP | 1025805 A1 | 8/2000 |
| EP | 1311226 A1 | 5/2003 |
| EP | 1504713 A1 | 2/2005 |
| EP | 1717601 A2 | 11/2006 |
| EP | 1932477 A1 | 6/2008 |
| EP | 2313143 A1 | 4/2011 |
| EP | 2337491 A1 | 6/2011 |
| EP | 2440122 A1 | 4/2012 |
| EP | 2464407 A2 | 6/2012 |
| EP | 2482719 A1 | 8/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2618727 A1 | 7/2013 |
| EP | 2632360 A1 | 9/2013 |
| EP | 2219526 B1 | 3/2014 |
| EP | 2712547 A1 | 4/2014 |
| EP | 2992825 B1 | 5/2017 |
| EP | 2265175 B1 | 8/2017 |
| FR | 2545349 | 11/1984 |
| IN | 9721/DELNP/2011 | 1/2013 |
| JP | 01097440 | 4/1989 |
| JP | 03173542 A | 7/1991 |
| JP | 4090741 | 8/1992 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001161683 | 6/2001 |
| JP | 2001-514533 A | 9/2001 |
| JP | 2001-524339 A | 12/2001 |
| JP | 2001340334 | 12/2001 |
| JP | 2002-224069 A | 8/2002 |
| JP | 2002-529133 A | 9/2002 |
| JP | 2002-541947 A | 12/2002 |
| JP | 2003-010138 A | 1/2003 |
| JP | 2003501127 A | 1/2003 |
| JP | 2003061752 A | 3/2003 |
| JP | 2003299654 | 10/2003 |
| JP | 2003334191 | 11/2003 |
| JP | 2002520893 | 2/2004 |
| JP | 2004505748 T | 2/2004 |
| JP | 2004515298 A | 5/2004 |
| JP | 2006508744 A | 3/2006 |
| JP | 2006-338526 A | 12/2006 |
| JP | 2007-000226 A | 1/2007 |
| JP | 2007-068989 A | 3/2007 |
| JP | 2007-105450 A | 4/2007 |
| JP | 2007-313122 A | 12/2007 |
| JP | 2009/271123 A | 11/2009 |
| JP | 5010604 | 6/2012 |
| JP | 2012-529929 | 11/2012 |
| JP | 2013-518676 A | 5/2013 |
| JP | 2013-526959 A | 6/2013 |
| JP | 2013-526961 A | 6/2013 |
| WO | 1980002376 A1 | 11/1980 |
| WO | 9112836 A1 | 9/1991 |
| WO | 1992003090 | 3/1992 |
| WO | 1994003159 A1 | 2/1994 |
| WO | 1994004938 | 3/1994 |
| WO | 1996005768 A1 | 2/1996 |
| WO | 1996007352 A1 | 3/1996 |
| WO | 1996041119 | 12/1996 |
| WO | 1997029683 A1 | 8/1997 |
| WO | 1997043989 A1 | 11/1997 |
| WO | 1998025159 A1 | 6/1998 |
| WO | 98/29032 A1 | 7/1998 |
| WO | 1998035611 A1 | 8/1998 |
| WO | 199916495 A1 | 4/1999 |
| WO | 1999027837 A2 | 6/1999 |
| WO | 9949407 A1 | 9/1999 |
| WO | 2000019906 | 4/2000 |
| WO | 2000027281 A1 | 5/2000 |
| WO | 2000040155 | 7/2000 |
| WO | 2000063658 A2 | 10/2000 |
| WO | 2000074775 A1 | 12/2000 |
| WO | 2001013792 A1 | 3/2001 |
| WO | 2001039683 A1 | 6/2001 |
| WO | 2001076479 A1 | 10/2001 |
| WO | 02/07794 A2 | 1/2002 |
| WO | 2002015973 A1 | 2/2002 |
| WO | 2002019905 A1 | 3/2002 |
| WO | 2002025277 A1 | 3/2002 |
| WO | 2002085442 A1 | 10/2002 |
| WO | 2003061752 | 7/2003 |
| WO | 2003077759 A1 | 9/2003 |
| WO | 03/088833 A1 | 10/2003 |
| WO | 2003091495 A1 | 11/2003 |
| WO | 2004002303 A1 | 1/2004 |
| WO | 2004049970 A2 | 6/2004 |
| WO | 2005033524 A1 | 4/2005 |
| WO | 2005033574 A1 | 4/2005 |
| WO | 2005117690 A1 | 12/2005 |
| WO | 2005117733 A2 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |

(56) References Cited

FOREIGN PATENT DOCUMENTS

| | | |
|---|---|---|
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 | 3/2008 |
| WO | 2008083111 | 7/2008 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |
| WO | 2009000439 A1 | 12/2008 |
| WO | 2009002514 A2 | 12/2008 |
| WO | 2009003138 A1 | 12/2008 |
| WO | 2009009064 A1 | 1/2009 |
| WO | 2009057774 A1 | 5/2009 |
| WO | 2009063166 A1 | 5/2009 |
| WO | 2009067654 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010029906 A1 | 3/2010 |
| WO | 2010030820 A1 | 3/2010 |
| WO | 2010132857 A1 | 11/2010 |
| WO | 2010132985 A1 | 11/2010 |
| WO | 2010143196 A1 | 12/2010 |
| WO | 2010144922 A1 | 12/2010 |
| WO | 2011019760 A2 | 2/2011 |
| WO | 2011041450 A1 | 4/2011 |
| WO | 2011044421 A1 | 4/2011 |
| WO | 2011057289 A2 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2011150376 A1 | 12/2011 |
| WO | 2012021542 A2 | 2/2012 |
| WO | 2012024577 A2 | 2/2012 |
| WO | 2012039866 A1 | 3/2012 |
| WO | 2012040487 A1 | 3/2012 |
| WO | 2012058461 A1 | 5/2012 |
| WO | 2012083245 A1 | 6/2012 |
| WO | 2012088535 A1 | 6/2012 |
| WO | 2012110955 A1 | 8/2012 |
| WO | 2012173697 A1 | 12/2012 |
| WO | 2013006713 A2 | 1/2013 |
| WO | 2013006817 A1 | 1/2013 |
| WO | 2013034175 A1 | 3/2013 |
| WO | 2014052894 A2 | 4/2014 |
| WO | 2014062728 A1 | 4/2014 |
| WO | 2014138652 A1 | 9/2014 |
| WO | 2014138918 A1 | 9/2014 |
| WO | 2015/120256 A2 | 8/2015 |
| WO | 2016/210325 A1 | 12/2016 |

OTHER PUBLICATIONS

Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.

Markovich, Mary B., Central Venous Catheter Tip Placement: Determination of Posterior Malposition-A Case Study, JAVA, vol. 11, No. 2, pp. 85-89, 2006.

Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.

McDonnall, "Intra-Atrial Electrocardiography (ECG) for Catheter Placement." Literature review prepared for Bard Access Systems, Oct. 2007.

McGee et al., "Accurate Placement of Central Venous Catheters: A Prospective, Randomize, Multicenter Trail." Critical Care Medicine, vol. 21 No. 8, Aug. 1993.

MedGraphics, CardioPerfect® Resting/Stress ECG System, 3 pages, 2001.

Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.

Michenfelder, John et al, Air Embolism During Neurosurgery. A New Method of Treatment, Anesthesia and Analgesia. Current Researches, pp. 390-395, vol. 45, No. 4, Jul.-Aug. 1966.

MICROBIRD$^{TM}$ Miniaturized DC Magnetic Sensors for Intra-body Navigation and Localization, Specifications, 2005.

MICRONIX CathRite$^{TM}$ Cardiac Access Device Brochure. Jun. 2004.

Micronix Pty Ltd "CathRite" Guiding Styled Core Manufacturing, Jun. 15, 2006.

Murthy, Vrudhula et al, Analysis of Power Spectral Densities of Electrocardiograms, Mathematical Biosciences, pp. 41-51, vol. 12 No. 1-2, Oct. 1971.

Nadroo, AM et al, Changes in Upper Extremity Position Cause Migration of Peripherally Inserted Central Catheters in Neonates, Pediatrics, pp. 131-136, vol. 110, Jul. 2002.

Nakatani, K et al, Accurate Placement of Central Venous Catheters—ECG-guided method vs Patient Height Method, MASUI, pp. 34-38, vol. 51 No. 1, Jan. 2002.

Nazarian, GK et al, Changes in Tunneled Catheter Tip Position when a patient is Upright, J Vasc Interv Radiol, pp. 437-441, vol. 8 No. 3, May-Jun. 1997.

NEUROMETER® CPT, Clinical Applications. Neurotron , Inc. website: www.neurotron.com/CLINAPS.html, last accessed Oct. 23, 2006.

NEUROMETER® CPT, Frequently Asked Questions. Neurotron , Inc. website: www.neurotron.com/CPTFAQ/html, last accessed Oct. 23, 2006.

NEUROMETER® CPT, Products Page. Neurotron , Inc. website: www.neurotron.com/products.html, last accessed Oct. 23, 2006.

NEUROMETER® Electrodiagnostic Neuroselective Sensory Nerve Evaluation: Charts, Tables, Documents & Downloads. Neurotron , Inc. website: www.neurotron.com/downloads.html, last accessed Oct. 23, 2006.

Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.

Palesty, JA et al, Routine Chest Radiographs Following Central Venous Recatherization over a Wire are not Justified, Am J Surg, pp. 618-621, vol. 176 No. 6, Dec. 1998.

Paliotti, Roberta P. et al, Intravascular Doppler Technique for Monitoring Renal Venous Blood Flow in Man, J Nephrol, pp. 57-62, 2003.

Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.

Pawlik, et al., "Central Venous Catheter Placement: Comparison of the Intravascular Guidewire and the Fluid Column Electrocardiograms." European Journal of Anaesthesiology, vol. 41, pp. 594-599, 2004.

PCT/US2006/033079 filed Aug. 24, 2006 International Preliminary Report on Patentability dated Feb. 26, 2008.

(56) References Cited

OTHER PUBLICATIONS

PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.

DELTEC Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
EP 08855396.1 filed Jun. 15, 2010 European Search Report dated Jul. 31, 2012.
EP 09808901.4 filed Aug. 21, 2009 European Search Report dated May 23, 2012.
EP 09813632.8 filed Apr. 5, 2011 European Search Report dated Jul. 4, 2012.
EP 12177438.4 filed Jul. 23, 2012 European Search Report dated Dec. 4, 2012.
EP 12177438.4 filed Jul. 23, 2012 extended European Search Report dated Mar. 25, 2013.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov-Dec 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hill, Bradley et al, Abstract of article discussing VasaNova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.

(56) References Cited

OTHER PUBLICATIONS

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Joosting, Jean-Pierre, "Dual-interface RFID-compatible EEPROM enables remote access to electronic device parameters," EE Times, Mar. 8, 2010.
JP 2008-528151 filed Aug. 24, 2006 Notice of Grant dated May 6, 2012.
JP 2010-504220 filed Sep. 3, 2009 Office Action dated May 21, 2012.
Kim, Ko et al, Positioning Internal Jugular Venous Catheters using the Right Third Intercostal Space in Children, Acta Anaesthesiol Scand, pp. 1284-1286, vol. 47 No. 10, Nov. 2003.
Kjelstrup T et al, Positioning of Central Venous Catheters using ECG, Tidssk nor Laegeforen, pp. 599-601, vol. 111 No. 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Interv Radiol, pp. 443-447, vol. 8 No. 3, May-Jun. 1997.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intraluminal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.
AU 2011289513 filed Jan. 21, 2013 Examiner's Report dated Jul. 5, 2013.
AU 2012202293 filed Apr. 19, 2012 Examination Report No. 1 dated Apr. 24, 2013.
AU 2013204243 filed Apr. 12, 2013 Examiner's Report dated Jun. 5, 2013.
CN 200880012117.4 filed Apr. 16, 2008 Third Office Action dated Apr. 27, 2013.
CN 200880125528.4 filed Nov. 25, 2008 Third Office Action dated Jul. 1, 2013.
EP 08855396.1 filed Jun. 15, 2010 Intent to Grant dated Jul. 5, 2013.
EP 09707467.8 supplemental European search report dated Jun. 18, 2013.
EP 09808901.4 filed Aug. 21, 2009 Examination Report dated May 10, 2013.
EP 09813632.8 filed Apr. 5, 2011 Office Action dated Apr. 30, 2013.
JP 2010-504220 filed Sep. 3, 2009 Final Office Action dated Apr. 18, 2013.
PCT/US2011/047127 filed Aug. 9, 2011 International Preliminary Report on Patentability dated Apr. 18, 2013.
PCT/US2011/058138 filed Oct. 27, 2011 International Preliminary Report on Patentability dated May 10, 2013.
PCT/US2011/067268 filed Dec. 23, 2011 International Preliminary Report on Patentability dated Jul. 4, 2013.
U.S. Appl. No. 12/900,750, filed Oct. 8, 2010 Non-Final Office Action dated Jun. 3, 2013.
U.S. Appl. No. 13/213,622, filed Aug. 19, 2011 Final Office Action dated Feb. 19, 2013.
U.S. Appl. No. 13/336,919, filed Dec. 23, 2011 Advisory Action dated May 23, 2013.
U.S. Appl. No. 29/428,649, filed Aug. 1, 2012 Notice of Allowance dated Jul. 5, 2013.
Stereotaxis, Expanding the Possibilites of Interventional Medicine: Remote Navigation and Automation, pp. 1-8, Apr. 2011.
Tepa® Health Innovation PC based ECG System Introduction and Technical Specifications, EKG Master USB, 2 pages, Nov. 2003.
The FloWire Doppler Guide Wire located <http://www.volcanocorp.com/products/flowire-doppler-guide-wire.php>, 2011.
TRAXAL Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602, filed Aug. 23, 2006 Final Office Action dated Apr. 8, 2010.
U.S. Appl. No. 11/466,602, filed Aug. 23, 2006 Final Office Action dated Jan. 30, 2009.
U.S. Appl. No. 11/466,602, filed Aug. 23, 2006 Non-Final Office Action dated Mar. 28, 2013.
U.S. Appl. No. 11/466,602, filed Aug. 23, 2006 Non-Final Office Action dated Sep. 25, 2009.
U.S. Appl. No. 11/466,602, filed Aug. 23, 2006 Notice of Allowance dated Dec. 3, 2012.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 11/552,094, filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Non-Final Office Action dated Jul. 20, 2011.
U.S. Appl. No. 12/426,175, filed Apr. 17, 2009 Non-Final Office Action dated Dec. 3, 2012.
U.S. Appl. No. 12/427,244, filed Apr. 21, 2009 Non-Final Office Action dated Jan. 19, 2012.
U.S. Appl. No. 12/545,762, filed Aug. 21, 2009 Final Office Action dated Mar. 7, 2013.
U.S. Appl. No. 12/545,762, filed Aug. 21, 2009 Non-Final Office Action dated Aug. 1, 2012.
U.S. Appl. No. 12/557,401, filed Sep. 10, 2009 Non-Final Office Action dated Apr. 24, 2012.
U.S. Appl. No. 12/575,456, filed Oct. 7, 2009 Non-Final Office Action dated Oct. 5, 2012.
U.S. Appl. No. 12/715,556, filed Mar. 2, 2010 Non-Final Office Action dated Sep. 13, 2012.
U.S. Appl. No. 12/854,083, filed Aug. 10, 2010 Non-Final Office Action dated Jan. 29, 2013.

(56) References Cited

OTHER PUBLICATIONS

U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 13/118,138, filed May 27, 2011 Final Office Action dated Apr. 3, 2013.
U.S. Appl. No. 13/118,138, filed May 27, 2011 Non-Final Office Action dated Oct. 3, 2012.
U.S. Appl. No. 13/213,622, filed Aug. 19, 2011 Non-Final Office Action dated Jul. 31, 2012.
U.S. Appl. No. 13/283,395, filed Oct. 27, 2011 Non-Final Office Action dated Apr. 23, 2013.
U.S. Appl. No. 13/336,919, filed Dec. 23, 2011 Final Office Action dated Mar. 1, 2013.
U.S. Appl. No. 13/336,919, filed Dec. 23, 2011 Non-Final Office Action dated Oct. 16, 2012.
U.S. Appl. No. 13/337,987, filed Dec. 27, 2011 Non-Final Office Action dated Mar. 15, 2013.
Valdivieso, J.R. Perez, et al., Evaluation of a formula for optimal positioning of a central venous catheter inserted through the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak© Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak$^{TM}$ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAV, vol. 13, No. 4, pp. 179-185, 2008.
Polos, PG. et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack®catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N. et al, Assessment of Distal Tip Position of Long Term Central Venous Feeding Catheters using Transesophageal Echocardiology, JPEN J Parenter Enteral Nutr, pp. 39-41, vol. 25 No. 1, Jan./Feb. 2001.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. 1988 Jan;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.

(56) References Cited

OTHER PUBLICATIONS

Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiography Using J-Wire." Paediatric Anaesthesia vol. 9, pp. 501-504, 1999.
Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
Stereotaxis Magetic Navigation System with Navigant™ User Interface, 2005 Brochure.
Wilson, R. G. et al, Right Atrial Electrocardiography in Placement of Central Venous Catheters, The Lancet, pp. 462-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
Yoon, SZ et al, Usefulness of the Carina as a Radiographic Landmark for Central Venous Catheter Placement in Paediatric Patients, Br J Anaesth, Jul. 2005.
Yoshida, Teruhisa et al, Detection of Concealed Left Sided Accessory Atrioventricular Pathway by P Wave Signal Averaged Electrocardiogram, J Am Coll Cardiol, pp. 55-62, 1999.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Zachariou, Zacharias et al., Intra-atrial ECG recording: a new and safe method for implantation of Broviac catheters in children, Pediatr Surg Int (1994) 9: 457-458.
"ASCENSION to Launch New 3D Guidance$_{TM}$ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans RAECG Adapter-Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2006283022 filed Aug. 24, 2006 Office Action dated Dec. 22, 2010.
AU 2008329807 exam requested Aug. 13, 2012 Examination Report No. 1 dated Feb. 15, 2013.
AURORA® System Technical Specifications, Oct. 2003.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JM et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
BioAdvance Lumen Vu, Greenhouse Fund Feb. 2004 Recipient, www.bioadvance.com <http://www.bioadvance.com>, 2005.
Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. Bard, CathTracku Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
CA 2,619,909 filed Aug. 24, 2006 Examiner's Report dated Oct. 26, 2012.

(56) References Cited

OTHER PUBLICATIONS

Cadman, A et al, To Clot or Not to Clot? That is the question in Central Venous Catheters, Clinical Radiology, pp. 349-355, vol. 59 No. 4, Apr. 2004.
Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventinal Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and Computing, pp. 331-334, vol. 17 No. 6, Aug. 2002.
Cavatorta, et al., "Central Venous Catheter Placement in Hemodialysis: Evaluation of Electrocardiography Using a Guidewire." The Journal of Vascular Access, vol. 2, pp. 45-50, 2001.
Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, Ki et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.
Clifford, et al. "Assessment of Hepatic Motion Secondary to Respiration for Computer Assisted Interventions." Computer Aided Surgery, vol. 7, pp. 291-299, 2002.
CN 200880012117.4 filed Apr. 16, 2008 First Office Action dated Dec. 23, 2011.
CN 200880012117.4 filed Apr. 16, 2008 Second Office Action dated Oct. 8, 2012.
CN 200880125528.4 filed Nov. 25, 2008 First Office Action dated Jun. 5, 2012.
CN 200880125528.4 filed Nov. 25, 2008 Second Office Action dated Mar. 6, 2013.
CN 200980123021.X filed Dec. 17, 2010 First Office Action dated Nov. 19, 2012.
CN 200980144663.8 filed May 9, 2011 First Office Action dated Dec. 5, 2012.
Colley, Peter S et al, ECG-Guided Placement of Sorenson CVP Catheters via Arm Veins, Anesthesia and Analgesia, pp. 953-956, vol. 63, 1984.
AU 2008329807 exam requested Aug. 13, 2012 Notice of Acceptance dated Feb. 14, 2014.
AU 2013201648 filed Mar. 19, 2013 Examiner's Report dated Mar. 5, 2014.
AU 2013201648 filed Mar. 19, 2013 Examiner's Report dated Oct. 14, 2013.
CN 200980123021.X filed Dec. 17, 2010 Second Office Action dated Aug. 13, 2013.
CN 200980144663.8 filed May 9, 2011 Second Office Action dated Aug. 22, 2013.
CN 201080035659.0 filed Feb. 10, 2012 First Office Action dated Jan. 26, 2014.
CN 201080053838.7 filed May 28, 2012 First Office Action dated Jan. 6, 2014.
EP 12177438.4 filed Jul. 23, 2012 Communication dated Jan. 13, 2014.
JP 2010-535117 filed May 26, 2011 First Office Action dated Aug. 5, 2013.
PCT/US13/62409 filed Sep. 27, 2013 International Search Report and Written Opinion dated Feb. 24, 2014.
PCT/US2013/065121 filed Oct. 15, 2013 International Search Report and Written Opinion dated Jan. 16, 2014.
U.S. Appl. No. 11/466,602, filed Aug. 23, 2006 Final Office Action dated Oct. 28, 2013.
U.S. Appl. No. 11/466,602, filed Aug. 23, 2006 Notice of Allowance dated Mar. 14, 2014.
U.S. Appl. No. 12/426,175, filed Apr. 17, 2009 Advisory Action dated Nov. 26, 2013.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/545,762, filed Aug. 21, 2009 Non-Final Office Action dated Dec. 13, 2013.
U.S. Appl. No. 12/557,401, filed Sep. 10, 2009 Non-Final Office Action dated Jan. 6, 2014.
U.S. Appl. No. 12/715,556, filed Mar. 2, 2010 Final Office Action dated Oct. 2, 2013.
U.S. Appl. No. 12/815,331, filed Jun. 14, 2010 Advisory Action dated Oct. 4, 2013.
U.S. Appl. No. 12/815,331, filed Jun. 14, 2010 Final Office Action dated Jul. 26, 2013.
U.S. Appl. No. 12/815,331, filed Jun. 14, 2010 Non-Final Office Action dated Jan. 22, 2013.
U.S. Appl. No. 12/854,083, filed Aug. 10, 2010 Final Office Action dated Aug. 15, 2013.
U.S. Appl. No. 12/854,083, filed Aug. 10, 2010 Non-Final Office Action dated Jan. 29, 2014.
U.S. Appl. No. 12/893,916, filed Sep. 29, 2010 Non-Final Office Action dated Dec. 24, 2013.
U.S. Appl. No. 13/019,939, filed Feb. 2, 2011 Non-Final Office Action dated Oct. 11, 2013.
U.S. Appl. No. 13/118,138, filed May 27, 2011 Final Office Action dated Aug. 1, 2013.
U.S. Appl. No. 13/336,919, filed Dec. 23, 2011 Non-Final Office Action dated Dec. 27, 2013.
U.S. Appl. No. 13/469,932, filed May 11, 2012 Non-Final Office Action dated Jan. 3, 2014.
U.S. Appl. No. 13/665,420, filed Oct. 31, 2012 Non-Final Office Action dated Jan. 6, 2014.
JP 2012-552060 filed Aug. 1, 2012 Office Action dated Nov. 12, 2014.
JP 2012-552060 filed Aug. 1, 2012 Second Office Action dated Nov. 6, 2015.
JP 2013-512046 filed Nov. 26, 2012 Decision of Rejection dated Dec. 8, 2015.
JP 2013-512046 filed Nov. 26, 2012 First Office Action dated Mar. 23, 2015.
JP 2013-512051 filed Nov. 26, 2012 First Office Action dated Mar. 23, 2015.

(56) References Cited

OTHER PUBLICATIONS

JP 2013-524999 filed Jan. 22, 2013 First Office Action dated Jun. 1, 2015.
Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.
MX/a/2012/013672 filed Nov. 23, 2012 First Office Action dated Aug. 10, 2015.
MX/a/2012/013858 filed Nov. 28, 2012 First Office Action dated Sep. 26, 2014.
MX/a/2012/013858 filed Nov. 28, 2012 Second Office Action dated Jun. 10, 2015.
PCT/US2009/041051 filed Apr. 17, 2009 International Preliminary Report on Patentability dated Apr. 8, 2014.
PCT/US2011/048403 filed Aug. 19, 2011 International Preliminary Report on Patentability dated Jul. 30, 2013.
PCT/US2014/022019 filed Mar. 7, 2014 International Search Report and Written Opinion dated Jun. 11, 2014.
PCT/US2015/014795 filed Feb. 6, 2015 International Search Report and Written Opinion dated May 14, 2015.
Pittiruti, et al, "The intracavitary ECG method for positioning the tip of central venous catheters: results of an Italian multicenter study," J Vasc Access, pp. 1-9, Nov. 21, 2011.
Pittiruti, et al. "The electrocardiographic method for positioning the tip of central venous catheters" JAVA, pp. 1-12, Feb. 12, 2011.
RU 2011150917 filed Dec. 15, 2011 First Office Action dated Apr. 24, 2014.
RU 2011150917 filed Dec. 15, 2011 Second Office Action dated Aug. 28, 2014.
U.S. Appl. No. 1/118,033, filed May 27, 2011 Non-Final Office Action dated Jul. 8, 2015.
U.S. Appl. No. 12/426,175, filed Apr. 17, 2009 Examiner's Answer dated Oct. 7, 2014.
U.S. Appl. No. 12/545,762, filed Aug. 21, 2009 Non-Final Office Action dated Nov. 7, 2014.
U.S. Appl. No. 12/545,762, filed Aug. 21, 2009 Non-Final Office Action dated Sep. 11, 2015.
U.S. Appl. No. 12/815,331, filed Jun. 14, 2010 Advisory Action dated Mar. 5, 2015.
U.S. Appl. No. 12/815,331, filed Jun. 14, 2010 Final Office Action dated Dec. 23, 2014.
U.S. Appl. No. 12/815,331, filed Jun. 14, 2010 Final Office Action dated Nov. 4, 2015.
U.S. Appl. No. 12/815,331, filed Jun. 14, 2010 Non-Final Office Action dated Jul. 2, 2014.
U.S. Appl. No. 12/815,331, filed Jun. 14, 2010 Non-Final Office Action dated Jun. 1, 2015.
U.S. Appl. No. 12/854,083, filed Aug. 10, 2010 Advisory Action dated Sep. 8, 2014.
U.S. Appl. No. 12/854,083, filed Aug. 10, 2010 Final Office Action dated Aug. 21, 2015.
U.S. Appl. No. 12/854,083, filed Aug. 10, 2010 Final Office Action dated Jul. 1, 2014.
U.S. Appl. No. 12/854,083, filed Aug. 10, 2010 Non-Final Office Action dated Feb. 1, 2016.
U.S. Appl. No. 12/854,083, filed Aug. 10, 2010 Non-Final Office Action dated Mar. 16, 2015.
U.S. Appl. No. 12/893,916, filed Sep. 29, 2010 Advisory Action dated Aug. 15, 2014.
U.S. Appl. No. 12/893,916, filed Sep. 29, 2010 Final Office Action dated Jan. 15, 2015.
U.S. Appl. No. 12/893,916, filed Sep. 29, 2010 Final Office Action dated Jun. 18, 2014.
U.S. Appl. No. 12/893,916, filed Sep. 29, 2010 Non-Final Office Action dated Sep. 10, 2015.
U.S. Appl. No. 12/893,916, filed Sep. 29, 2010 Non-Final Office Action dated Sep. 25, 2014.
U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated Feb. 9. 2015.
U.S. Appl. No. 13/118,033, filed May 27, 2011 Non-Final Office Action dated Feb. 3, 2015.
U.S. Appl. No. 13/118,033, filed May 27, 2011 Non-Final Office Action dated May 22, 2014.
U.S. Appl. No. 13/118,138, filed May 27, 2011 Non-Final Office Action dated Jul. 15, 2015.
U.S. Appl. No. 13/118,138, filed May 27, 2011 Non-Final Office Action dated Oct. 9, 2014.
U.S. Appl. No. 13/213,622, filed Aug. 19, 2011 Non-Final Office Action dated May 22, 2014.
U.S. Appl. No. 13/240,171, filed Sep. 22, 2011 Advisory Action dated Aug. 18, 2015.
U.S. Appl. No. 13/240,171, filed Sep. 22, 2011 Final Office Action dated Jun. 10, 2015.
U.S. Appl. No. 13/240,171, filed Sep. 22, 2011 Non-Final Office Action dated Dec. 1, 2015.
U.S. Appl. No. 13/240,171, filed Sep. 22, 2011 Non-Final Office Action dated Dec. 26, 2014.
U.S. Appl. No. 13/283,395, filed Oct. 27, 2011 Advisory Action dated Jan. 28, 2014.
U.S. Appl. No. 13/283,395, filed Oct. 27, 2011 Final Office Action dated Nov. 14, 2013.
AU 2010300677 filed Mar. 12, 2012 First Examination Report dated Mar. 9, 2014.
AU 2013202824 filed Apr. 6, 2013 First Examiner's Report dated Mar. 10, 2014.
Benzadon, M. N. et al: "Comparison of the Amplitude of the P-Wave from Intracardiac Electrocardiogram Obtained by Means of a Central Venous Catheter Filled With Saline Solution to That Obtained Via Esophageal Electrocardiogram", American Journal of Cardiology, Cahners Publishing Co., Newton, MA, U.S., vol. 98, No. 7, Oct. 1, 2006 (Oct. 1, 2006), pp. 978-981.
CA 2,721,715 filed Apr. 17, 2009 Examiner's Report dated Aug. 18, 2015.
CN 200980123021.X filed Dec. 17, 2010 Third Office Action dated Apr. 22, 2014.
CN 200980144663.8 filed May 9, 2011 Fifth Office Action dated May 26, 2015.
CN 200980144663.8 filed May 9, 2011 Fourth Office Action dated Nov. 15, 2014.
CN 200980144663.8 filed May 9, 2011 Third Office Action dated May 4, 2014.
CN 201080035659.0 filed Feb. 10, 2012 Second Office Action dated Oct. 9, 2014.
CN 201080035659.0 filed Feb. 10, 2012 Third Office Action dated Mar. 19, 2015.
CN 201080053838.7 filed May 28, 2012 Fourth Office Action dated Jun. 2, 2015.
CN 201080053838.7 filed May 28, 2012 Second Office Action dated Jun. 17, 2014.
CN 201080053838.7 filed May 28, 2012 Third Office Action dated Dec. 4, 2014.
CN 201180016462.7 filed Sep. 27, 2012 First Office Action dated Mar. 21, 2014.
CN 201180016462.7 filed Sep. 27, 2012 Second Office Action dated Dec. 9, 2014.
CN 201180016462.7 filed Sep. 27, 2012 Third Office Action dated Jun. 10, 2015.
CN 201180037065.8 filed Jan. 28, 2013 First Office Action dated Jun. 2, 2015.
CN 201180037065.8 filed Jan. 28, 2013 First Office Action dated Sep. 28, 2014.
CN 201180037068.1 filed Jan. 28, 2013 First Office Action dated Apr. 20, 2015.
CN 201180037068.1 filed Jan. 28, 2013 First Office Action dated Sep. 9, 2014.
CN 201180037068.1 filed Jan. 28, 2013 Third Office Action dated Oct. 19, 2015.
CN 201180040151.4 filed Feb. 19, 2013 First Office Action dated Oct. 28, 2014.

(56) References Cited

OTHER PUBLICATIONS

CN 201180040151.4 filed Feb. 19, 2013 Second Office Action dated Jun. 19, 2015.
CN 201180040151.4 filed Feb. 19, 2013 Third Office Action dated Dec. 10, 2015.
CN 201180043512.0 filed Mar. 8, 2013 First Office Action dated Jul. 31, 2014.
CN 201180043512.0 filed Mar. 8, 2013 Second Office Action dated Apr. 14, 2015.
CN 201180052587.5 filed Apr. 28, 2013 First Office Action dated Jan. 26, 2015.
CN 201180052587.5 filed Apr. 28, 2013 Second Office Action dated Aug. 19, 2015.
CN 201180068309.9 filed Aug. 22, 2013 First Office Action dated Oct. 16, 2014.
CN 201180068309.9 filed Aug. 22, 2013 Second Office Action dated May 6, 2015.
CN 201180068309.9 filed Aug. 22, 2013 Third Office Action dated Sep. 2, 2015.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10821193.9 filed Mar. 27 2012 Partial European Search Report dated Oct. 9, 2015.
EP 11 818 828.3 filed Mar. 18, 2013 Extended European Search Report dated Dec. 10, 2014.
EP 11787515.3 filed Dec. 12, 2012 partial European search report dated Jun. 23, 2015.
EP 11787515.3 filed Dec. 12, 2012 partial European search report dated Oct. 27, 2015.
EP 11787527.8 filed Dec. 19 2012 Extended European Search Report dated Oct. 9, 2015.
EP 11787527.8 filed Dec. 19, 2012 partial European search report dated May 26, 2015.
EP 11837113.7 filed May 28, 2013 Extended European Search Report dated Apr. 24, 2014.
EP 12177438.4 filed Jul. 23, 2012 European Search Report dated Jun. 7, 2015.
EP 12177438.4 filed Jul. 23, 2012 Examination Report dated Dec. 5, 2014.
EP 12807886.2 filed Jan. 15, 2014 Extended European Search Report dated Feb. 6, 2015.
EP 13194818.4 filed Nov. 28, 2013 extended European search report dated Feb. 28, 2014.
EP 14151268.1 filed Jan. 15, 2014 European Search Report dated Feb. 21, 2014.
EP14197136.6 filed Dec. 10, 2014 Extended European Search Report dated May 26, 2015.
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
JP 2012-515222 filed Dec. 9, 2011 Office Action dated Feb. 23, 2015.
JP 2012-515222 filed Dec. 9, 2011 Office Action dated Mar. 24, 2014.
U.S. Appl. No. 13/336,919, filed Dec. 23, 2011 Final Office Action dated Dec. 19, 2014.
U.S. Appl. No. 13/336,919, filed Dec. 23, 2011 Non-Final Office Action dated Jul. 9, 2015.
U.S. Appl. No. 13/469,932, filed May 11, 2012 Non-Final Office Action dated Jul. 31, 2014.
U.S. Appl. No. 13/469,932, filed May 11, 2012 Non-Final Office Action dated Sep. 4, 2015.
U.S. Appl. No. 13/665,420, filed Oct. 31, 2012 Non-Final Office Action dated Jul. 9, 2015.
U.S. Appl. No. 13/665,420, filed Oct. 31, 2012 Non-Final Office Action dated Oct. 9, 2014.
U.S. Appl. No. 13/737,806, filed Jan. 9, 2013 Notice of Allowance dated Oct. 31, 2013.
U.S. Appl. No. 13/887,166, filed May 3, 2013 Examiner's Answer dated Jul. 16, 2015.
U.S. Appl. No. 13/890,158, filed May 8, 2013 Non-Final Office Action dated Aug. 15, 2014.
U.S. Appl. No. 13/890,158, filed May 8, 2013 Non-Final Office Action dated Jul. 9, 2015.
U.S. Appl. No. 13/969,265, filed Aug. 16, 2013 Non-Final Office Action dated Dec. 19, 2013.
U.S. Appl. No. 13/969,265, filed Aug. 16, 2013 Notice of Allowance dated Jun. 23, 2014.
U.S. Appl. No. 14/141,046, filed Dec. 26, 2013 Non-Final Office Action dated Feb. 11, 2015.
U.S. Appl. No. 14/141,046, filed Dec. 26, 2013 Non-Final Office Action dated Jun. 20, 2014.
U.S. Appl. No. 14/141,046, filed Dec. 26, 2013 Non-Final Office Action dated Nov. 5, 2015.
U.S. Appl. No. 14/201,300, filed Mar. 7, 2014 Non-Final Office Action dated Jan. 6, 2016.
U.S. Appl. No. 14/270,241, filed May 5, 2014 Non-Final Office Action dated Apr. 23, 2015.
U.S. Appl. No. 14/270,241, filed May 5, 2014 Notice of Allowance dated Oct. 7, 2015.
U.S. Appl. No. 14/309,511, filed Jun. 19, 2014 Non-Final Office Action, dated Sep. 24, 2015.
U.S. Appl. No. 14/317,501, filed Jun. 27, 2014 Advisory Action dated Sep. 16, 2015.
U.S. Appl. No. 14/317,501, filed Jun. 27, 2014 Final Office Action dated Jul. 1, 2015.
U.S. Appl. No. 14/317,501, filed Jun. 27, 2014 Non-Final Office Action dated Mar. 3, 2015.
U.S. Appl. No. 14/317,501, filed Jun. 27, 2014 Non-Final Office Action dated Sep. 12, 2014.
U.S. Appl. No. 14/449,061, filed Jul. 31, 2014 Final Office Action dated Nov. 6, 2015.
U.S. Appl. No. 14/449,061, filed Jul. 31, 2014 Non-Final Office Action dated Apr. 27, 2015.
U.S. Appl. No. 14/506,552, filed Oct. 3, 2014 Non-Final Office Action dated Oct. 1, 2015.
U.S. Appl. No. 14/548,151, filed Nov. 19, 2014 Non-Final Office Action dated Jun. 5, 2015.
Zaidi, Naveed A., et al. "Room temperature magnetic order in an organic magnet derived from polyaniline." 2004, Polymer, vol. 45, pp. 5683-5689.
CN 201180052587.5 filed Apr. 28, 2013 Office Action dated Feb. 24, 2016.
JP 2013-512046 filed Nov. 26, 2012 Office Action dated May 16, 2016.
U.S. Appl. No. 12/893,916, filed Sep. 29, 2010 Final Office Action dated Mar. 25, 2016.
U.S. Appl. No. 13/118,033, filed May 27, 2011 Final Office Action dated Apr. 1, 2016.
U.S. Appl. No. 13/118,138, filed May 27, 2011 Final Office Action dated Apr. 1, 2016.
U.S. Appl. No. 13/240,171, filed Sep. 22, 2011 Final Office Action dated May 6, 2016.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.
U.S. Appl. No. 14/040,205, filed Sep. 27, 2013 Non-Final Office Action dated Mar. 10, 2016.
U.S. Appl. No. 14/201,300, filed Mar. 7, 2014 Final Office Action dated May 5, 2016.
U.S. Appl. No. 14/449,061, filed Jul. 31, 2014 Notice of Allowance dated Apr. 13, 2016.
U.S. Appl. No. 14/498,887, filed Sep. 26, 2014 Non-Final Office Action dated Feb. 19, 2016.
CN 200880012117.4 filed Apr. 16, 2008 Fourth Office Action dated Sep. 4, 2013.

(56) References Cited

OTHER PUBLICATIONS

CN 201180037065.8 filed Jan. 28, 2013 Third Office Action dated Nov. 24, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201410009216.4 filed Jan. 8, 2014 Second Office Action dated Sep. 25, 2015.
EP 09743249.6 filed Oct. 18, 2010 Extended European Search Report dated Jan. 13, 2016.
EP 11740309.7 filed Aug. 23, 2012 Extended European Search Report dated Aug. 3, 2015.
EP 15179061.5 filed Jul. 30, 2015 Extended European Search Report dated Jan. 14, 2016.
JP 2010-504220 filed Sep. 3, 2009 Office Action dated Apr. 1, 2014.
JP 2010-504220 filed Sep. 3, 2009 Office Action dated Apr. 18, 2013.
JP2013-530322 filed Mar. 18, 2013, First Office Action dated Jul. 31, 2015.
MX/a/2013/001317 filed Jan. 31, 2013 First Office Action dated Nov. 26, 2015.
U.S. Appl. No. 12/369,625, filed Feb. 11, 2009 Notice of Panel Decision dated Aug. 1, 2012.
U.S. Appl. No. 12/545,762, filed Aug. 21, 2009 Non-Final Office Action dated Feb. 16, 2016.
U.S. Appl. No. 13/337,987 filed Dec. 27, 2011 Examiner's Answer dated Jul. 2, 2014.
U.S. Appl. No. 13/337,987, filed Dec. 27, 2011 Final Office Action dated Sep. 19, 2013.
U.S. Appl. No. 13/858,782, filed Apr. 8, 2013 Notice of Allowance dated Oct. 9, 2014.
CN 201410009216.4 filed Jan. 8, 2014 Office Action dated Jun. 15, 2016.
KR 10-2012-7000866 filed Jan. 11, 2012 First Office Action dated Jun. 16, 2016.
RU 2013158008 filed Dec. 26, 2013 First Office Action dated May 27, 2016.
U.S. Appl. No. 12/893,916, filed Sep. 29, 2010 Advisory Action dated Jun. 2, 2016.
U.S. Appl. No. 13/240,171, filed Sep. 22, 2011 Advisory Action dated Jul. 22, 2016.
U.S. Appl. No. 13/336,919, filed Dec. 23, 2011 Notice of Allowance dated Jul. 26, 2016.
U.S. Appl. No. 13/469,932, filed May 11, 2012 Advisory Action dated Jun. 27, 2016.
U.S. Appl. No. 13/890,158, filed May 8, 2013 Advisory Action dated Jul. 26, 2016.
U.S. Appl. No. 14/141,046, filed Dec. 26, 2013 Advisory Action dated Aug. 4, 2016.
U.S. Appl. No. 14/201,300, filed Mar. 7, 2014 Advisory Action dated Jul. 18, 2016.
U.S. Appl. No. 14/309,511, filed Jun. 19, 2014 Notice of Allowance, dated Jul. 26, 2016.
U.S. Appl. No. 14/317,501, filed Jun. 27, 2014 Examiner's Answer dated Jun. 30, 2016.
U.S. Appl. No. 14/498,887, filed Sep. 26, 2014 Advisory Action dated Aug. 22, 2016.
U.S. Appl. No. 14/498,887, filed Sep. 26, 2014 Final Office Action dated Jun. 15, 2016.
U.S. Appl. No. 14/548,151, filed Nov. 19, 2014 Advisory Action dated Jul. 22, 2016.
CN 201180037065.8 filed Jan. 28, 2013 Fourth Office Action dated May 5, 2016.
JP 2014-519081 filed Dec. 27, 2013 First Office Action dated Apr. 26, 2016.
JP2013-530322 filed Mar. 18, 2013, Office Action dated May 2, 2016.
U.S. Appl. No. 14/141,046, filed Dec. 26, 2013 Final Office Action dated May 11, 2016.
AU 2012278809 filed Nov. 12, 2013 Notice of Acceptance dated Sep. 13, 2016.
CA 2,721,715 filed Apr. 17, 2009 Examiner's Report dated Oct. 25, 2016.
CN 201180037065.8 filed Jan. 28, 2013 Notice of Grant dated Aug. 30, 2016.
EP 13840356.3 filed Apr. 27, 2015 Partial European Search Report dated Oct. 19, 2016.
EP 13846380.7 filed May 15, 2015 Partial European Search Report dated Sep. 30, 2016.
EP 14761249.3 Filed Sep. 3, 2015 Extended European Search Report dated Sep. 19, 2016.
KR 10-2012-7000866 filed Jan. 11, 2012 Second Office Action dated Nov. 3, 2016.
PCT/US2016/039356 filed Jun. 24, 2016 International Search Report and Written Opinion dated Sep. 16, 2016.
U.S. Appl. No. 12/426,175, filed Apr. 17, 2009 Decision on Appeal dated Nov. 7, 2016.
U.S. Appl. No. 12/545,762, filed Aug. 21, 2009 Non-Final Office Action dated Sep. 26, 2016.
U.S. Appl. No. 12/893,916, filed Sep. 29, 2010 Non-Final Office Action dated Aug. 31, 2016.
U.S. Appl. No. 13/118,033, filed May 27, 2011 Notice of Allowance dated Sep. 2, 2016.
U.S. Appl. No. 14/040,205, filed Sep. 27, 2013 Final Office Action dated Oct. 19, 2016.
U.S. Appl. No. 14/054,700, filed Oct. 15, 2013 Final Office Action dated Oct. 19, 2016.
U.S. Appl. No. 14/201,300, filed Mar. 7, 2014 Non-Final Office Action dated Aug. 24, 2016.
U.S. Appl. No. 14/548,151, filed Nov. 19, 2014 Non-Final Office Action dated Sep. 28, 2016.
CN 201510144728.6 filed Apr. 17, 2015 Office Action dated Jan. 23, 2017.
CO 15110530 filed May 14, 2015 Office Action dated Nov. 25, 2016.
U.S. Appl. No. 12/426,175, filed Apr. 17, 2009 Notice of Allowance dated Dec. 13, 2016.
U.S. Appl. No. 14/040,205, filed Sep. 27, 2013 Advisory Action dated Dec. 15, 2016.
U.S. Appl. No. 14/054,700, filed Oct. 15, 2013 Advisory Action dated Dec. 15, 2016.
U.S. Appl. No. 14/201,300, filed Mar. 7, 2014 Final Office Action dated Dec. 19, 2016.
U.S. Appl. No. 14/615,932, filed Feb. 6, 2015 Non-Final Office dated Dec. 29, 2016.
U.S. Appl. No. 14/846,496, filed Sep. 4, 2015 Non-Final Office Action dated Nov. 25, 2016.
U.S. Appl. No. 15/160,958, filed May 20, 2016 Non-Final Office Action dated Dec. 15, 2016.
CA 2800810 filed Nov. 26, 2012 Office Action dated Mar. 30, 2017.
CN 200980144663.8 filed May 9, 2011 Decision of Re-Examination dated Feb. 21, 2017.
CN 201380065663.5 filed Jun. 15, 2015 Office Action dated Mar. 15, 2017.
EP 09743249.6 filed Oct. 18, 2010 Intention to Grant dated Mar. 2, 2017.
EP 13840356.3 filed Apr. 27, 2015 Extended European Search Report dated Mar. 22, 2017.
JP 2013-530322 filed Mar. 18, 2013, Office Action dated Mar. 2, 2017.
U.S. Appl. No. 12/545,762 filed Aug. 21, 2009 Final Office Action dated Apr. 10, 2017.
U.S. Appl. No. 13/665,420, filed Oct. 31, 2012 Non-Final Office Action dated Mar. 15, 2017.
U.S. Appl. No. 13/890,158, filed May 8, 2013 Non-Final Office Action dated Apr. 7, 2017.
U.S. Appl. No. 14/141,046, filed Dec. 26, 2013 Non-Final Office Action dated Apr. 7, 2017.
U.S. Appl. No. 14/201,300, filed Mar. 7, 2014 Advisory Action dated Mar. 2, 2017.
U.S. Appl. No. 14/201,300, filed Mar. 7, 2014 Non-Final Office Action dated Mar. 30, 2017.

(56) References Cited

OTHER PUBLICATIONS

U.S. Appl. No. 14/548,151, filed Nov. 19, 2014 Final Office Action dated Apr. 19, 2017.
U.S. Appl. No. 15/160,958, filed May 20, 2016 Final Office Action dated Apr. 21, 2017.
U.S. Appl. No. 15/284,355, filed Oct. 3, 2016 Non-Final Office Action dated Apr. 24, 2017.
CO 15110530 filed May 14, 2015 Office Action dated May 8, 2017.
EP 11850625.2 filed Jul. 22, 2013 Extended European Search Report dated Jun. 21, 2017.
EP 15746326.6 filed Jul. 1, 2016 Extended European Search Report dated Jun. 9, 2017.
EP 17157118.5 filed Feb. 21, 2017 Extended European Search Report Jun. 8, 2017.
JP 2015-534770 filed Mar. 26, 2015 Office Action dated Jun. 12, 2017.
U.S. Appl. No. 12/545,762, filed Aug. 21, 2009 Notice of Panel Decision dated Jul. 14, 2017.
U.S. Appl. No. 14/040,205, filed Sep. 27, 2013 Examiner's Answer dated Jul. 20, 2017.
U.S. Appl. No. 14/054,700, filed Oct. 15, 2013 Examiner's Answer dated Jul. 3, 2017.
U.S. Appl. No. 14/201,300, filed Mar. 7, 2014 Final Office Action dated Jul. 10, 2017.
U.S. Appl. No. 15/160,958, filed May 20, 2016 Advisory Action dated Jul. 10, 2017.
U.S. Appl. No. 15/160,958, filed May 20, 2016 Notice of Allowance dated Jul. 26, 2017.
U.S. Appl. No. 15/585,051, filed May 2, 2017 Non-Final Office Action dated Jul. 14, 2017.
CN 201380065663.5 filed Jun. 15, 2015 Office Action dated Oct. 10, 2017.
CN 201510144728.6 filed Apr. 17, 2015 Office Action dated Aug. 29, 2017.
EP 10786978.6 filed Dec. 19, 2011 Office Action dated Aug. 11, 2017.
EP 11827551.0 filed Feb. 7, 2013 Extended European Search Report dated Sep. 19, 2017.
EP 14197137.4 filed Dec. 10, 2014 Office Action dated, Sep. 20, 2017.
EP 14761249.3 Filed Sep. 3, 2015 Office Action dated Sep. 28, 2017.
KR 10-2013-7006933 filed Mar. 19, 2013 Office Action dated Aug. 7, 2017.
RU 2015111669 filed Apr. 1, 2015 Office Action dated Sep. 5, 2017.
U.S. Appl. No. 14/548,151, filed Nov. 19, 2014 Advisory Action dated Aug. 1, 2017.
U.S. Appl. No. 14/548,151, filed Nov. 19, 2014 Non-Final Office Action dated Sep. 21, 2017.
U.S. Appl. No. 14/788,305, filed Jun. 30, 2015 Restriction Requirement dated Aug. 25, 2017.
CN 201610166569.4 filed Dec. 23, 2010, Office Action dated Nov. 1, 2017.
JP 2013-530322 filed Mar. 18, 2013, Office Action dated Nov. 6, 2017.
U.S. Appl. No. 13/890,158, filed May 8, 2013 Final Office Action dated Nov. 21, 2017.
U.S. Appl. No. 14/141,046, filed Dec. 26, 2013 Final Office Action dated Dec. 11, 2017.
U.S. Appl. No. 14/317,501, filed Jun. 27, 2014 Decision on Appeal dated Nov. 17, 2017.
U.S. Appl. No. 14/788,305, filed Jun. 30, 2015 Non-Final Office Action dated Jan. 10, 2018.
U.S. Appl. No. 15/284,355, filed Oct. 3, 2016 Non-Final Office Action dated Nov. 17, 2017.
U.S. Appl. No. 15/365,698, filed Nov. 30, 2016 Non-Final Office Action dated Dec. 14, 2017.
U.S. Appl. No. 15/365,752, filed Nov. 30, 2016 Non-Final Office Action dated Dec. 13, 2017.

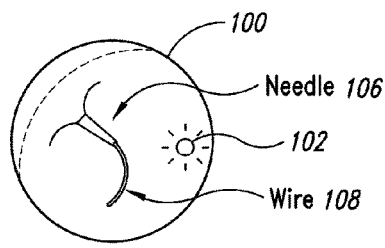
FIG. 5
(Prior Art)
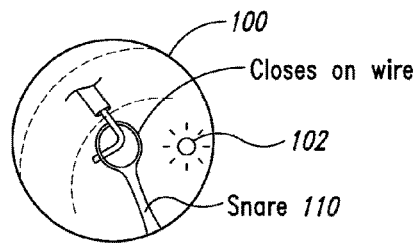
FIG. 6
(Prior Art)
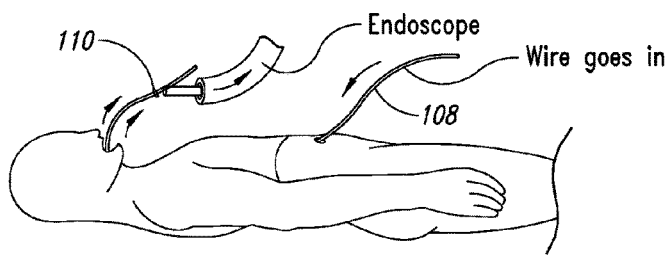
FIG. 7
(Prior Art)
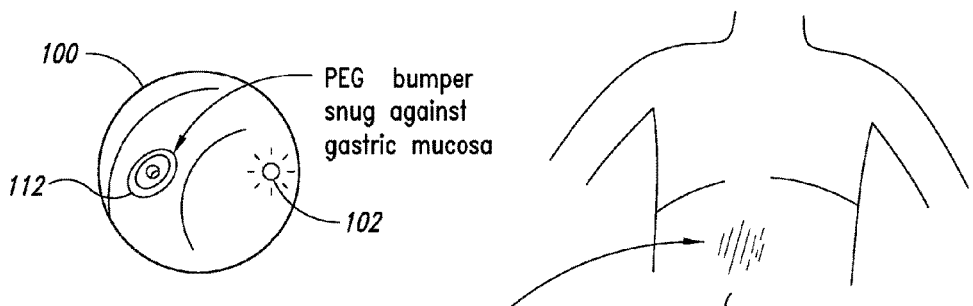
FIG. 8A
(Prior Art)
FIG. 8B

Can also just push bumper through outside to inside

PERCUTANEOUS MAGNETIC GASTROSTOMY

CROSS-REFERENCE TO RELATED APPLICATION

This application is a continuation of U.S. patent application Ser. No. 12/575,456, filed Oct. 7, 2009, now U.S. Pat. No. 8,437,833, which claims the benefit under 35 U.S.C. § 119(e) of U.S. Provisional Patent Application Ser. No. 61/103,419, filed Oct. 7, 2008, each of which is incorporated herein by reference in its entirety.

TECHNICAL FIELD

The present disclosure generally relates to the medical field and more particularly but not exclusively relates to the placement of feeding tubes or catheters into the body of a patient.

BACKGROUND INFORMATION

In many medical situations, it is necessary to penetrate the solid or semi-solid biological matter of the human body at substantially precise locations. For example, one common medical practice is placement of a percutaneous endoscopic gastrostomy (PEG) tube.

PEG is a procedure used to put a tube into the stomach of a patient who cannot swallow liquids and solids. FIG. 1A illustrates a PEG tube 112 in place in a human body. In some instances, the tube is instead placed into the small bowel via a gastrostomy. PEG is used in a wide variety of circumstances and generally is effective for helping patients. Traditionally, a PEG tube is placed using endoscopic guidance or x-ray guidance. This step is shown in FIG. 1B. For example, in a traditional PEG procedure to place a PEG tube into a patient's stomach 100, an endoscope is used to observe that the patient's esophagus is without obstruction or diverticulae or for other medical reasons, such as to avoid interference with the pylorus 102. An endoscope is also used to inspect the stomach and inflate the stomach to see that the area selected for the gastrostomy can be distended. In this manner, a medical practitioner (who may be an endoscopist) uses an endoscope to select an area of the lower body of the stomach or antrum (the gastric wall) that is particularly suitable for the PEG tube placement. This step is shown in FIG. 1C.

In another step of the traditional placement of a PEG tube procedure, the endoscopist shines the endoscopic light out from the gastric lumen in a darkened room so that a second medical practitioner (who may be any person trained in such medical procedures) can see the light and identify that it is in a reasonable location of the patient's body, e.g., not above the ribs. FIG. 2 shows how an endoscopic light may be seen to varying degree through the skin of a patient.

FIG. 3 shows another step in the traditional placement of a PEG tube in which the endoscopist will watch the second medical practitioner push a finger into the stomach wall and hopefully see the indentation 104 in the area selected by the endoscopist for the PEG tube placement.

FIG. 4A shows another step in the procedure of placing a PEG tube. If the location of the indentation is suitable, and especially if the indentation is clear, this spot is selected. The assistant then makes a small incision in the skin and inserts a needle 106 into the patient in the area in which the endoscope's light was seen.

FIG. 4B shows another step in the traditional placement of a PEG tube in which the endoscopist will watch a needle 106 as it is pushed through the patient's skin and then through the abdominal wall, and the endoscopist will watch the needle tip enter the stomach in the selected area.

FIG. 5 shows another step in the traditional placement of a PEG tube in which the endoscopist will see a wire 108 pass through the needle 106 into the gastric lumen.

FIG. 6 shows another step in the traditional placement of a PEG tube in which the endoscopist will use an endoscopic snare 110 to grasp the wire 108 firmly. The endoscopist uses the snare 110, passed through the biopsy channel of the endoscope, to firmly grab the wire 108. The endoscope and snare 110 are then withdrawn via the patient's mouth, thereby pulling the wire 108 with it. The part of the wire 108 that extends out from the patient's mouth is subsequently attached to a PEG tube.

FIG. 7 shows another step in the traditional placement of a PEG tube in which the endoscopist has withdrawn the entire endoscope, including the snare 110 holding the wire 108 that was passed through the needle 106, and the wire that passes through the needle extends out of the patient's mouth.

Once the wire 108 is successfully passed through the patient, a PEG tube 112 is secured to the end of the wire extending from the patient's mouth. The PEG tube 112 is guided into the patient's mouth and pulled into the patient's stomach 100 as the wire 108 is pulled from the end that passed through the needle 106. Once the PEG tube 112 is in the stomach, it is pulled partially through the gastric and abdominal walls until the bumper of the PEG tube is snug against the gastric mucosa.

FIG. 8A shows another step in the traditional placement of a PEG tube 112 in which an endoscope is again passed into a patient and subsequently used to visually observe that the bumper of the PEG tube 112 is snug against the gastric mucosa.

In other traditional PEG tube placement procedures, endoscopy is not used at all. Instead, x-ray is used to help select a particularly suitable location in the patient's body (e.g., the stomach) for the introduction of the PEG tube. X-ray is used for guiding the PEG tube placement and for inspecting the PEG tube's final position.

BRIEF SUMMARY

The present embodiments address several problems of traditional PEG placement by using new procedures and devices for placement of medical equipment.

One aspect provides an apparatus that includes a flexible piece of medical tubing having a proximal end and a distal end, an element affixed to the distal end, the element having ferromagnetic properties, and a first lumen extending lengthwise through the flexible tube, the lumen configured to pass matter into the patient.

Another aspect provides a system for placing a medical device through a patient having medical tube means for passing matter into the patient, ferromagnetic means affixed to a distal end of the medical tube means for identifying a substantially precise location of the distal end, detection means for locating the distal end of the medical tube means, means for passing a medical wire between a first location occupied by the detection means and a second location occupied by the ferromagnetic means, and means for attaching the medical device to the medical wire.

Another aspect provides an endoscopic-like controllable guide tube apparatus having a flexible tube free of optics, suction, irrigation, and light sources, a channel configured to pass a magnetic tipped medical device, and a control operative to orient a distal end of the flexible tube.

Another aspect provides a magnetic nasogastric tube apparatus having a flexible tube having a proximal end and a distal end, wherein the flexible tube is torsionally rigid, an element affixed to the distal end, the element having ferromagnetic properties, and at least one indicator located near the proximal end operative to communicate the orientation of the distal end relative to the indicator.

Another aspect provides a magnetic gastrostomy placement tube apparatus having a torsionally rigid flexible tube having a proximal end and a distal end, an element affixed to the distal end, the element having ferromagnetic properties, at least one indicator located near the proximal end of the torsionally rigid flexible tube, the indicator operative to communicate an orientation of the distal end relative to the indicator, a channel formed lengthwise along the torsionally rigid flexible tube, the channel operative to pass a guide wire, and an outer surface of the magnetic gastrostomy placement tube configured to be sterilizable.

Another aspect provides a method for placing a magnetic nasogastric tube into a patient having the steps of verifying that the patient's esophagus is unobstructed, placing a distal end of the magnetic nasogastric tube into the patient's mouth, advancing the magnetic nasogastric tube down the patient's throat, advancing the magnetic nasogastric tube through the patient's esophagus; and advancing the magnetic nasogastric tube into the patient's stomach.

Another aspect provides a method of selecting a location on a patient's body for placing a percutaneous gastrostomy tube having the steps of advancing a magnetic nasogastric tube into a patient, locating a distal end of the magnetic nasogastric tube with a magnetic detection sensor device, and positioning the distal end of the magnetic nasogastric tube into a desirable area by manipulating a proximal end of the magnetic nasogastric tube.

Another aspect provides a method of placing a medical device into a patient's body having the steps of advancing a magnetic nasogastric tube into a patient's stomach, locating a distal end of the magnetic nasogastric tube with a magnetic detection sensor device, positioning the distal end of the magnetic nasogastric tube into a desirable area by manipulating a proximal end of the magnetic nasogastric tube, distending the patient's stomach by passing a gas through the magnetic nasogastric tube, passing a needle through the patient's abdominal wall at about the desirable area, passing a medical wire through the patient's abdominal wall, and using the medical wire to position the medical device into the patient's body.

Another aspect provides a method for using an endoscopic-like controllable guide tube having the steps of passing a flexible tube configured on the endoscopic-like controllable guide tube through the mouth of a patient and into the patient's stomach and passing a magnetic nasogastrostomy tube down a channel in the endoscopic-like controllable guide tube.

Another aspect provides a method for installing a percutaneous gastrostomy tube having the steps of passing a magnetic nasogastrostomy tube into the stomach of a patient, verifying that the gastric cavity allows a distal end of the magnetic nasogastrostomy tube to move freely, pressing the distal end of the magnetic nasogastrostomy tube against the patient's gastric wall, placing a magnetic detection sensor device against the patient's abdominal skin, detecting the distal end of the magnetic nasogastrostomy tube with the magnetic detection sensor device, and placing the percutaneous gastrostomy tube through the patient's abdominal wall toward the distal end of the magnetic nasogastrostomy tube.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. One or more embodiments are described hereinafter with reference to the accompanying drawings in which:

FIG. 5 shows a medical wire entering the stomach through a needle as seen by an endoscopist according to the prior art;

FIG. 6 shows a snare, passed via the endoscope, grasping the medical wire according to the prior art;

FIG. 7 shows the snare holding the medical wire is pulled out of the patient according to the prior art;

FIG. 8A shows the bumper of a PEG tube against the gastric wall as seen by an endoscopist according to the prior art;

FIG. 8B shows a circumstance where the light from an endoscope shining on the abdominal wall is vaguely seen;

DETAILED DESCRIPTION

Traditional PEG placement procedures are imperfect, costly, and have many problems. For example, in some situations the endoscope's light is not clear on the abdominal wall. This is especially a problem if the patient is obese with a thick abdominal wall or if organs are between the stomach wall and the anterior abdominal wall (e.g., liver, colon, etc.). Using the endoscopic light to locate a suitable area of the gastric wall is very difficult in some patients, which is a problem not easily solved with current procedures or equipment.

Another example where problems occur with current procedures and equipment is if the patient is obese or if the location is not ideal. In this situation, the indentation made by the medical practitioner pressing against the abdomen from the outside is not clear to the endoscopist. Instead, a vague area moves in response to the outside practitioner's finger. A thick wall, intervening organs, or poor positioning may cause the vague indentation or motion. The indentation may be hard to see endoscopically and in some cases, is a problematic way to determine where the needle will enter the stomach.

Another example of a problem with current procedures and medical devices occurs because the medical practitioners have very little information about the target. The practitioner only knows to insert the needle where the endoscopic light was seen. The practitioner neither knows the direction to advance the needle nor the depth of the stomach wall. For this reason, the needle may be inserted and pushed a considerable depth into the patient before the endoscopist and/or assisting medical practitioner realize that the position is not ideal. The needle may cause injury to the patient when it is deeply advanced and/or advanced multiple times in the wrong direction to the wrong depth.

FIG. 8B, for example, shows a situation where the endoscope's light is not clear on the abdominal wall. This is especially a problem if the patient is obese with a thick abdominal wall or if organs are between the stomach wall and the anterior abdominal wall (e.g., liver or colon). Using this light to locate the selected area of gastric wall is very difficult in some patients, which is a problem that is difficult to solve with current procedures or equipment.

Figure 1A:
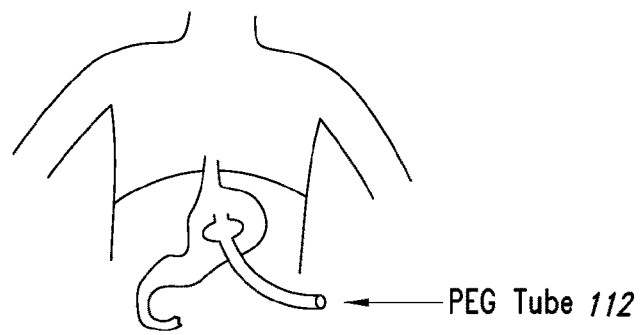
FIG. 1A illustrates a PEG tube in place in a human body.
Figure 1B:
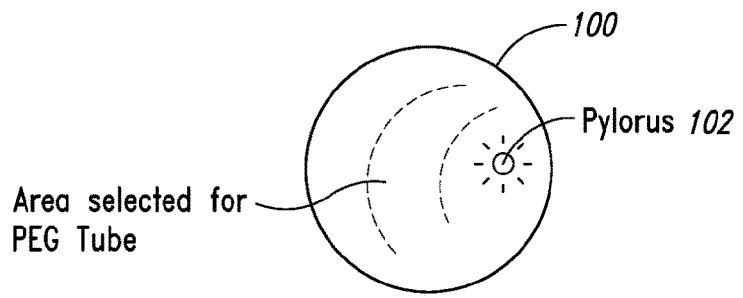
FIG. 1B shows an endoscope is used to inflate the stomach and select an area for the PEG tube according to the prior art.
Figure 1C:
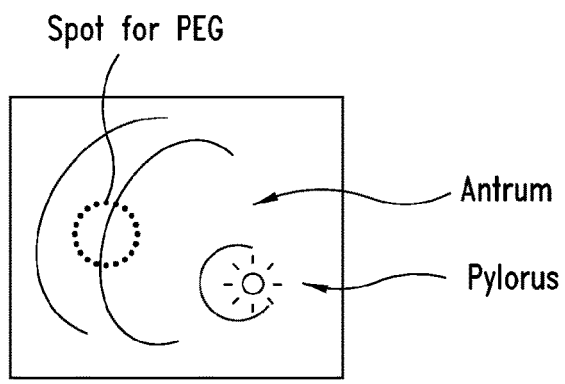
FIG. 1C shows, the view an endoscopist sees when looking at the stomach wall.
Figure 2:
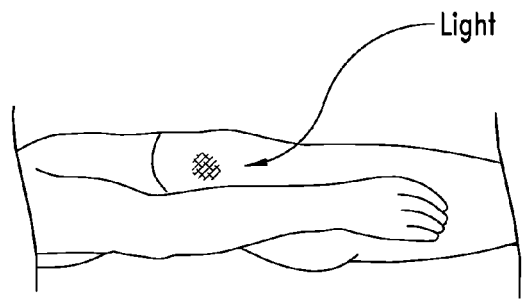
FIG. 2 shows the light of the endoscope is seen to varying degree on the skin of the patient according to the prior art.
Figure 3:
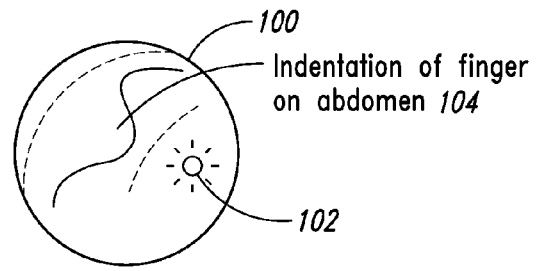
FIG. 3 shows the indentation of the second operator's finger as seen by an endoscopist according to the prior art.
Figure 4A:
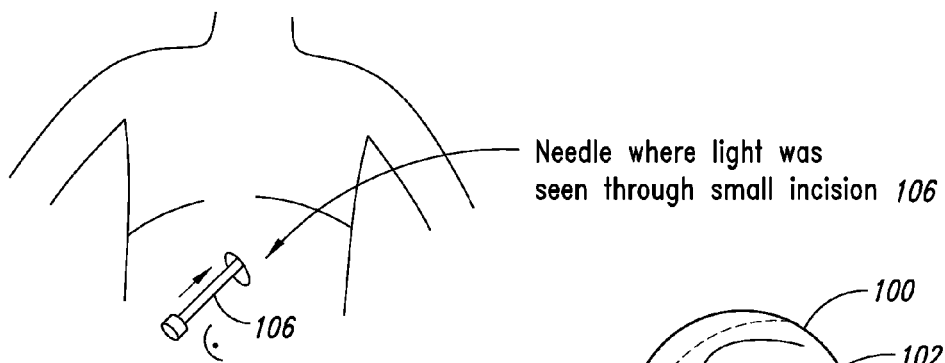
FIG. 4A shows a needle inserted into the patient via a small incision in the area in which the light of the endoscope was seen.
Figure 4B:
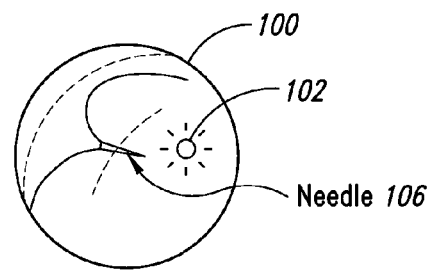
FIG. 4B shows the tip of a needle entering the stomach as seen by an endoscopist according to the prior art.
Figure 8C:
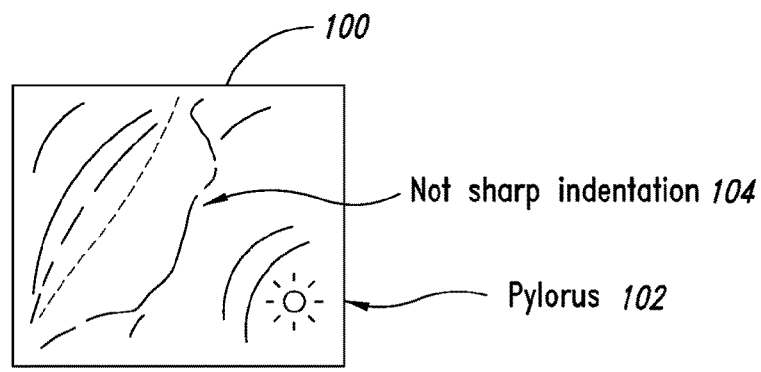
FIG. 8C shows the view an endoscopist sees if the indentation is broad and not clear when seen from the gastric side.

FIG. 8C, for example, shows another situation where problems occur with current procedures and equipment. If the patient is obese or if the location is not suitable, the indentation made by the assistant pressing against the abdomen with a finger 104 from the outside is not clear to the endoscopist. Instead, a vague area moves in response to the outside examiner's finger 104. A thick wall, intervening organs or poor positioning may cause the vague indentation or motion. The indentation may be hard to see and in some cases, is a problematic way to determine where the needle will enter the stomach.

Figure 8D:
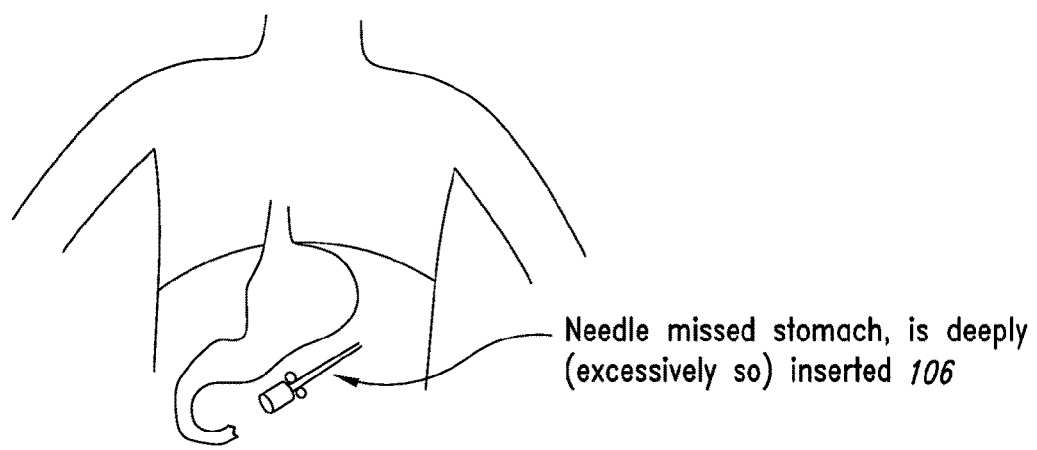
FIG. 8D shows a needle that has missed the stomach, gone deep into the patient, and put the patient in danger of an injured adjacent organ.

FIG. 8D shows another example of the type of problem that may occur with current procedures and medical devices. The assistant has very little information about the target. The assistant only knows to insert the needle 106 where the endoscope light was seen. The assistant neither knows the direction to advance the needle 106 nor the depth of the stomach wall. For this reason, the needle 106 may be inserted and pushed a considerable depth into the patient before the endoscopist and/or medical assistant realize that the position is not suitable. The needle 106 may cause injury to structures or adjacent organs when it is deeply advanced and/or advanced multiple times in the wrong direction to the wrong depth. In fact, it is common to limit the number of passages of the needle 106 to four passes.

Another example of a problem with traditional PEG placement procedures is that the procedures are implemented with costly medical equipment that is also relatively large and immobile. Both endoscopes and x-ray machines typically require large power supply systems and their use is not readily compatible with harsh physical environments. The expense, size, fragility, power requirements, and other limitations means that in some clinical areas, such as in less developed areas, nursing homes, or chronic care facilities, or in emergency situations, or battlefield or military aid station, for example, neither endoscopy nor x-ray is available, and the result is that traditional PEG procedures cannot be performed.

The problems described herein, and many others, may result in the inability to perform a PEG procedure because traditional medical equipment is unavailable. Further, even when the equipment is available, current procedures may result in perforation or other injury of an adjacent organ (for example the colon or liver), or may require multiple insertions, causing pain and trauma to the patient. Another problem is that the procedure may fail to successfully place the PEG tube at all. The current PEG placement procedure and devices have low precision and offer only minimal guidance, especially when the patient is not thin. The minimal guidance is very crude and depends both on the patient's habitus (thin is better for localization) and the medical practitioner's experience and judgment.

According to principles of the present invention, new tools and techniques are provided for integration with a living body as will now be described. These new techniques provides a unique way to precisely determine the location, direction, and depth of the selected site on the gastric wall without the use of endoscopic or x-ray equipment. They allow practitioners to have a higher assurance of the location of the site of penetration into the stomach of the needle and subsequent wire for the PEG tube.

A new alternative to PEG tube placement is presented herein and which can be called Percutaneous Magnetic Gastrostomy (PMG). Percutaneous Magnetic Gastrostomy does not require endoscopy or x-ray and therefore can be less expensive and can be performed in clinical areas in which neither endoscopy nor x-ray is available.

In the new gastrostomy procedures described herein and shown in the associated figures, no x-ray is used, and no endoscopy is necessary. The procedures are fast and guided safely by the presence of the magnetic element on the tip of the device passed into the patient's body. The equipment and procedures may be used in hospitals and may also be used in alternative sites such as a nursing home or in places which do not have x-ray or endoscopy. The gastrostomy equipment and procedures may be used wherever there is an acute need to get fluid and electrolytes into a patient who cannot swallow. Some examples where this equipment and procedures may be used are after trauma, in a third world location or similar environment in which there is simply not enough IV fluid, or on a battlefield to support the intravascular volume of an injured person. Rather than relying on IVs, the equipment and procedures disclosed use the patient's GI tract to rapidly absorb fluid, electrolytes and nutrients.

For example, in some situations, the small bowel is functioning normally and can readily absorb water, electrolytes, and nutrients (e.g., protein, carbohydrates, lipids) plus medications especially if modified with molecular chaperones to move rapidly into the patient via the small bowel mucosa. It may be possible to support a person in this way using non sterile fluids, electrolytes, and nutrients just as in normal food. Passing the fluids and electrolytes directly into the stomach via the gastrostomy tube has several advantages. For example, the fluid and nutrients need not be sterile, but instead can be food and water that one would drink. Also, a large volume can be passed using the stomach as a reservoir, and the speed of absorption of a fluid and electrolyte mixture introduced into the stomach may exceed that of an IV. Further, use of easily absorbed molecules or molecular chaperones may allow medications such as antibiotics to be absorbed from the small bowel very rapidly. This may be essential in a place where the IV solution of the medications is not available. It may be less expensive, and it may allow use of intragastrically delivered (e.g., to the GI tract) medications and does not limit the patient to IV medications only.

On the other hand these fluids and nutrients would not be tolerated if the material was given IV. This could be very important in a poor country or in trauma, or in other situations where IV fluid with sterile components may not be available in a suitable quantity.

In the following description, numerous specific details are given to provide a thorough understanding of embodiments. The invention can be practiced without one or more of the specific details, or with other methods, components, materials, etc., that are equivalent. In some instances, well-known structures, materials, or operations are not shown or described in detail to avoid obscuring aspects of the invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

In the embodiments and descriptions disclosed in the text and figures of the specification, several terms are used, including but not limited to, "magnet," "magnetic element," and elements or components having "magnetic properties."

Those skilled in the art will recognize that the specific terms are non-limiting and include hard or permanent magnets, soft magnets, electromagnets, and other material compositions having ferromagnetic properties. For example, the description of an element as a "magnet" may indicate that the element has or is constructed from a permanent magnet, a ferrous metal, or any other material having ferromagnetic properties.

A. Using a Magnetic Nasogastric Tube to Place a Peg Tube

Figure 9:
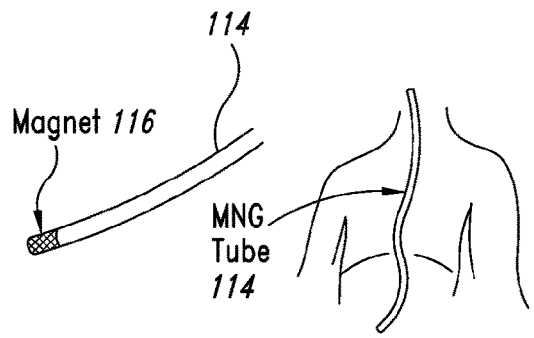
FIG. 9 shows a nasogastric (NG) tube with a magnet is passed into the stomach according to an embodiment.

One or more embodiments of the new approach to percutaneous gastrostomy are illustrated in FIGS. 9-20A and described in detail by way of non-limiting and non-exhaustive examples. FIG. 9 shows elements of a first example. A new type of nasogastric (NG) tube, a magnetic nasogastric (MNG) tube/catheter 114, is placed into the patient's mouth and gently advanced down into the stomach. Additional embodiments of the new type of nasogastric tube will be described later in this section.

Prior to inserting a tube down a patient's throat, the medical practitioner must have a degree of confidence that the esophagus is open. In the new approach to tube placement described herein, the practitioner may note that frequently, a patient with an abnormal esophagus will have symptoms of dysphagia. Also many of these patients will have been endoscoped recently or had an upper GI x-ray for their medical problem. Either will determine if the esophagus is abnormal. If there are symptoms or evidence of an abnormal esophagus, an endoscopy or x-ray should precede the Percutaneous Magnetic Gastrostomy procedure or, alternatively, a traditional PEG procedure may be performed. Ease of passage of the magnetic nasogastric tube is further evidence of a patent esophagus.

In example embodiments, the magnetic nasogastric tube 114 has a magnet 116 on the tip. In some embodiments, the magnetic nasogastric tube 114 has a ferrous metal element or a mass of ferrous material secured at a known location. The encapsulated magnet 116 may be a permanent magnet formed from any number of magnetic materials, including but not limited to AlNiCo, SmCo, and NdFeB types. The permanent magnet may be formed by a variety of process including but not limited to forming alloys, sintering of magnetic powders, and embedding magnetic powders within another binder material. The encapsulated magnet may also be an electromagnet, in which the magnetic field is generated by a steady or an alternating electric current passing through a wire coil of some size and shape, and in which the wire coil may surround a core of magnetically permeable material. The encapsulated magnet may also be a combination of a permanent magnet and electromagnet.

Figure 10A:
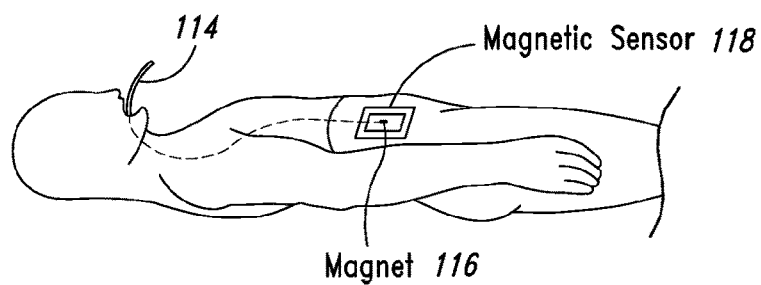
FIG. 10A shows a magnetic detection sensor device "seeing" the magnet in the stomach and assuring that the tip of the tube is actually below the ribs and most likely in the stomach according to an embodiment.
Figure 10B:
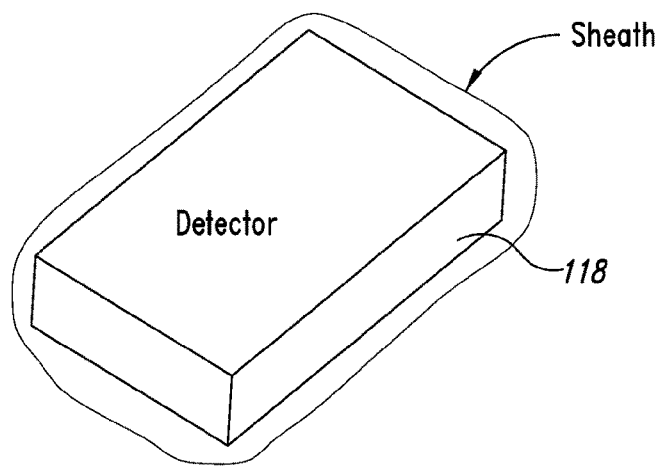
FIG. 10B shows a sensing device covered with a sheath in accordance with one embodiment.

When the desired length is passed (for instance approximately 50 cm for a typical adult patient), FIG. 10A shows a magnetic detection sensor device 118 is placed onto the abdominal wall to look for the magnet. FIG. 10B shows an embodiment of a magnetic detection sensor device 118. The magnetic detection sensor device 118 may also be referred to as a "magnetic sensing device," "sensing device," "sensor device," "detector," or the like.

Figure 11A:
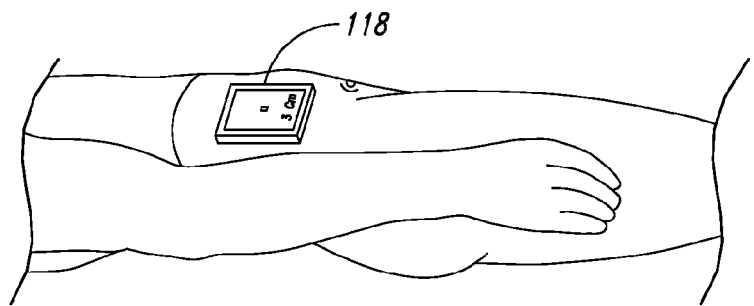
FIG. 11A shows a magnetic detection sensor device locating the magnet and giving a substantially precise distance according to an embodiment.

A disposable or reusable sterile sheath 120 covers the sensing device to prevent contamination with the placement of the needle 106 and wire 108. The sensing device 118 is placed on the patient's abdominal wall. The sensing device 118 can readily locate the magnet 116 on the tip of the magnetic nasogastric tube 114. In some embodiments, an audible indication informs the examiner of the position of the magnet 116. In other embodiments, a display is used in cooperation with an audible indicator or a display is used by itself. Additional examples of techniques that may be used by the magnetic detection sensor device to determine the location and orientation of magnets are disclosed in U.S. Pat. Nos. 5,879,297, 6,129,668, 6,216,028, and 6,263,230. The medical practitioners that are operating the magnetic nasogastric tube and the magnetic detection sensor device may choose an area that is particularly suitable for the Percutaneous Magnetic Gastrostomy tube by rotating the magnetic nasogastric tube and by moving the sensor device until the magnet is "seen" in the desired area. The magnetic detection sensor device, as shown in FIG. 11A, can then determine the distance from the skin to the magnet.

Figure 11B:
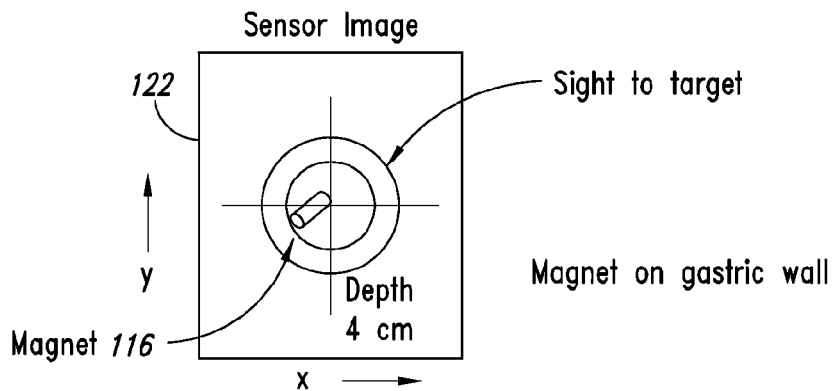
FIG. 11B shows an image on a magnet sensing device, where X and Y are noted as well as Z, depth, along with the direction of a magnet in accordance with one embodiment.

For example, FIG. 11B shows the X and Y position noted on a high-resolution or other suitable display screen 122 that may be integrated with the sensing device 118 or coupled to the sensing device 118.

Figure 11C:
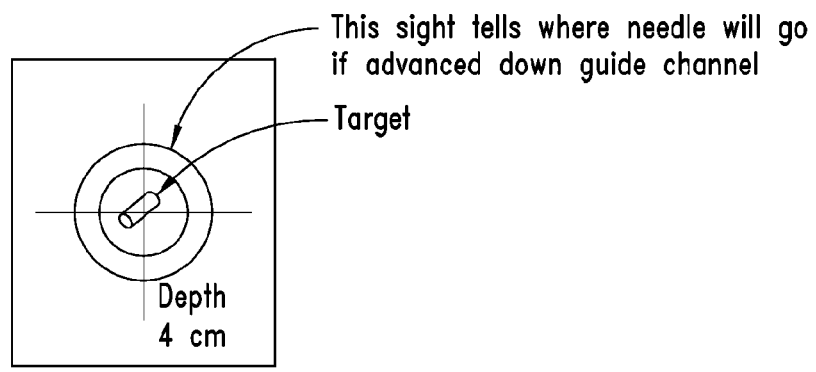
FIG. 11C shows a target guide on a sensing device's screen along with the depth to the magnet in accordance with one embodiment.

An example layout of the display screen 122 can be in the form of target "crosshairs." The distance from the sensing device on the patient's skin to the magnet (i.e., the depth, or Z position) is determined with substantial precision and also shown on the screen 122. In addition, the direction from the skin to the magnet 116 is known and can be displayed on the screen 122 as a target guide. For example, and as represented in FIG. 11C, the sensing device 118 can be repositioned along the outer surface of the stomach of the patient, until the target magnet 116 is centered in the crosshairs of the screen 122.

Figure 12:
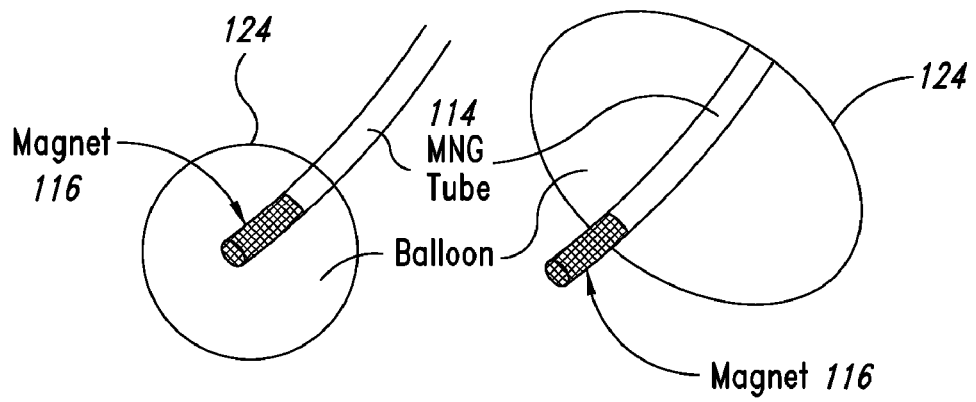
FIG. 12 shows a balloon inflating around or behind the magnet on the magnetic nasogastric tube according to an embodiment.

In some embodiments, once the position and depth of the desired location on the magnetic nasogastric tube 114 is determined, a balloon may be inflated in the stomach 100. FIG. 12 shows a balloon 124 inflating around or behind the magnet on the magnetic nasogastric tube 114 according to an embodiment. In other embodiments, the stomach is inflated without a balloon. The distensibility of the antrum is evaluated in embodiments of the percutaneous magnetic gastrostomy approach by knowing that the balloon or stomach cavity will inflate to an appropriate volume, e.g., approximately 300 cc for a typical adult patient. This may demonstrate that the magnetic nasogastric tube 114 is in the stomach as other areas (e.g., the small bowel) will not gently distend when the area is inflated. In some embodiments, a pressure valve prevents high pressure distension of the balloon 124.

In other embodiments, a combination is used where a balloon 124 is inflated to be sure that the area distends followed by distention of the stomach using a side port on the magnetic nasogastric tube 114. This will create space for a needle tip to enter the stomach away from the stomach's opposite wall and the needle tip may safely contact the magnetic element 116 on the tip of the magnetic nasogastric tube 114.

In some embodiments, the magnetic element is placed in the geometric center of the balloon 124. In some embodiments, the volume of the balloon is approximately 300 cc. In some embodiments, the balloon is filled with sterile water or other media, including air. In some embodiments, rather than placing the magnetic element in the center of the balloon, the balloon may be located behind the magnetic element. Embodiments where the tip of a magnetic nasogastric tube 114 is inside the balloon 124 and where the tip of the magnetic nasogastric tube 114 is outside the balloon 124 are shown in FIG. 12.

Figure 13:
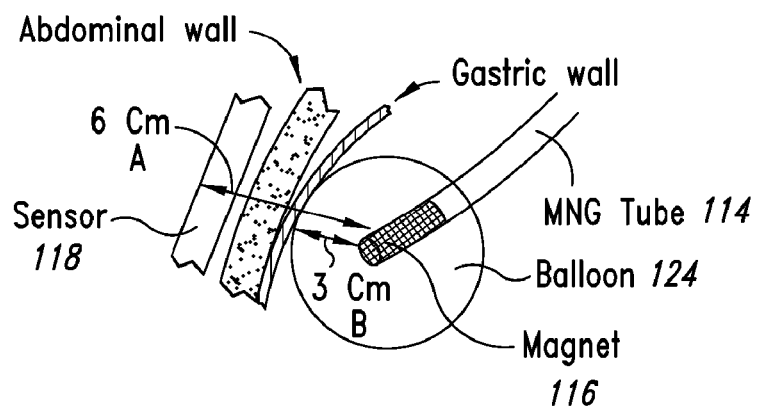
FIG. 13 shows the operator "seeing" the magnet regardless of whether or not the magnet is inside a balloon, and if the magnet is inside the balloon, the operator knows and can compensate appropriately for distances according to an embodiment.

As shown in FIG. 13, the medical practitioner then watches as the magnet 116 moves away by the distance B from the outside of the balloon 124 to the magnet 116 in the center if the centering balloon is used. The inflated balloon 124 lets the operator know that the area being examined is distensible. In other embodiments, the balloon 124 may be inflated while the tip of the magnetic nasogastric tube 114 remains outside of the balloon 124 rather than the balloon 124 inflating around the magnet 116. This allows the medical practitioner to know that the area of the stomach is distensible but allows the magnet 116 to remain pressed against the gastric mucosa.

Accordingly, in embodiments where a balloon 124 is inflated, the area to be used for the PEG tube 112 placement is that where the magnet 116 is located initially and after the balloon 124 is inflated.

Figure 14A:
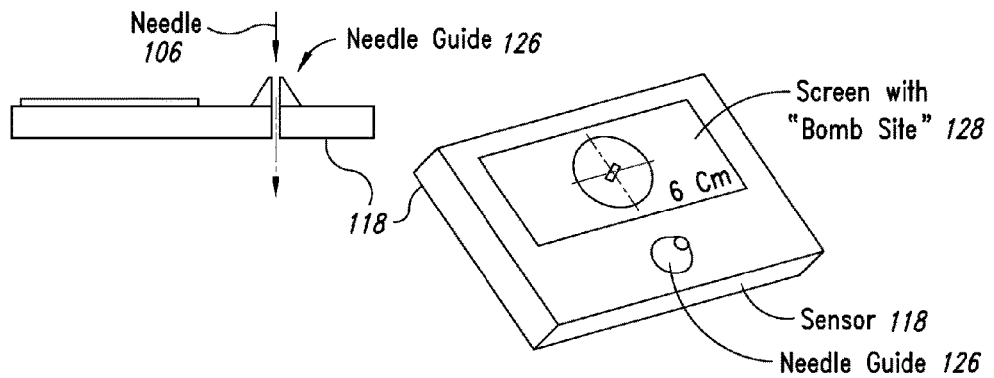
FIG. 14A shows the needle guide directing the needle to the magnet on the magnetic nasogastric tube with substantial precision according to an embodiment.

FIG. 14A shows a magnetic detection sensor device 118 with a guide path 126 for a needle 106 from the outside to be placed into the gastric lumen to touch the magnetic nasogastric tube magnet 116 regardless of whether the magnet 116 is against the mucosa or inside a balloon 124. The detector may provide a visual guide to the magnet 116 and also may provide a fixed needle guide 126 using a bomb site-like mechanism 128. For example, as illustrated in FIGS. 13 and 14A, the detector identifies a distance A, 6 cm, from the sensor's needle guide to the tip of the magnet.

Regardless of what type of indicator and guide the sensor has (e.g., a visual display, a bomb site, a needle guide, etc.), when the new percutaneous magnetic gastrostomy approach is used, an endoscopic light shined from the inside is not needed because the medical practitioner can "see" the magnet on the tip of the magnetic nasogastric catheter with the magnetic detection sensor device. Similarly, when the new percutaneous magnetic gastrostomy approach is used, the finger indentation of traditional PEG tube placement is not needed.

Figure 14B:
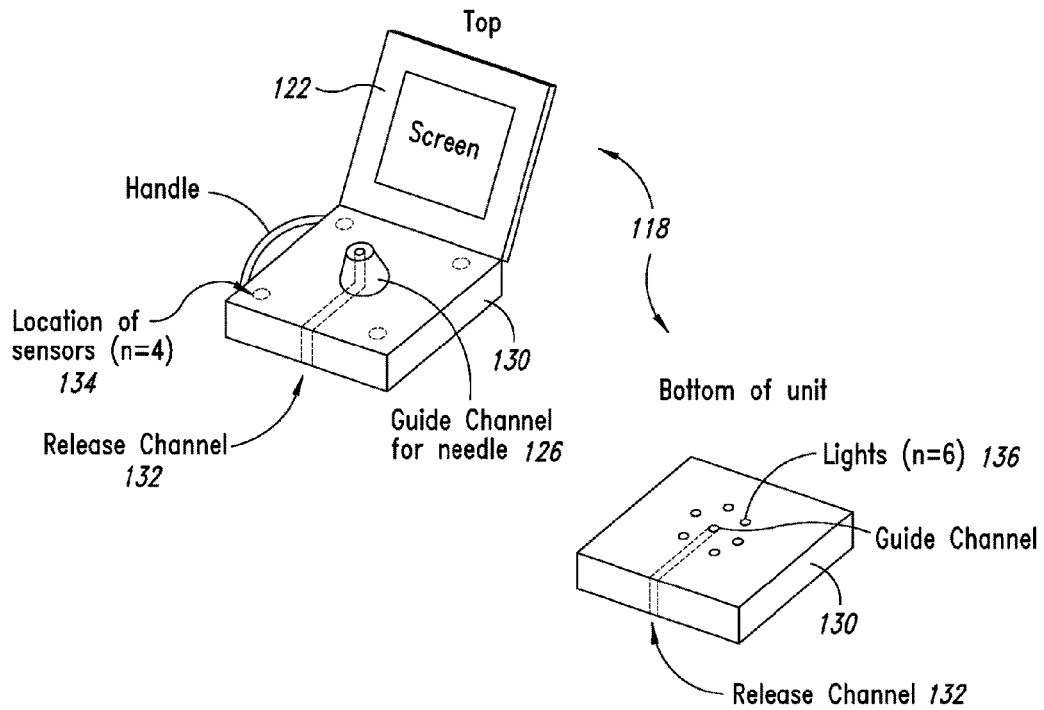
FIG. 14B shows a ring of lights of appropriate frequency and sufficient intensity to penetrate the skin and abdomen and to be readily seen on the inside of the patient by the endoscopist, on the bottom of a sensing device along with a guide channel through the ring used to guide the needle insertion in accordance with one embodiment.

In one embodiment and as shown in FIG. 14B, the sensing device 118 can take the form of a housing that has a folding display screen 122 and a base 130 that carries the magnetic sensors 134 (4 sensors in the illustrated example, located at the corners of the base 130). Centrally located between the sensors 134 and passing linearly through the sensing device 118 is a vertically oriented guide channel 126, through which a needle 106 can be inserted into the patient. In an embodiment, the guide channel 126 corresponds to the center of the "crosshairs" 128 of the display screen 122, such that if the needle 106 is inserted in the guide channel 126, the needle 106 will penetrate substantially at the location indicated by the center of the crosshairs 128, which guides the needle 106 to the magnet 116 location inside the body.

Figure 14C:
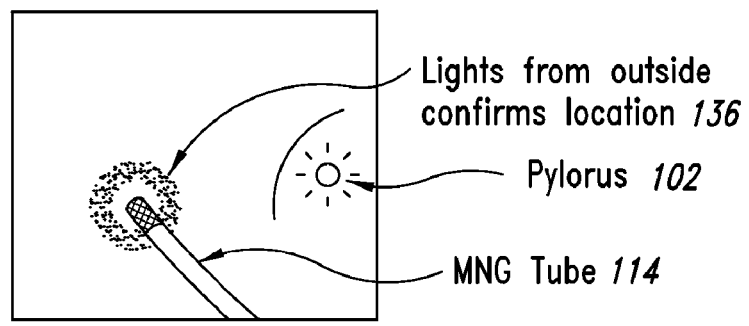
FIG. 14C shows a situation where the endoscopist clearly sees the light from the ring of lights on the bottom of a sensing device in the area targeted for needle placement in accordance with one embodiment.

The sensing device 118 of one embodiment includes a light emitting element. For example, a plurality (such as a ring or circular pattern) of LED lights 136 or other light source on the underside of the housing, such as shown in FIG. 14C. If the location and depth is determined to be adequate, the ring of LED lights 136 is then activated on the bottom 130 of the magnetic sensing device 118 around the guide channel 126. As shown in the embodiment of FIG. 14C, the exit hole of the guide channel 126 is centrally located with respect to the ring of LED lights 136. The ring of lights 136 is of a frequency and/or intensity and/or color suited to penetrate the abdominal wall so that the endoscopist may see it. For example, continuously lit and/or flashing bright LED's may be used if they provide sufficient intensity.

As illustrated in FIG. 14C, the endoscopist may then see the ring of lights 136 (from the sensing device) clearly on the gastric wall and confirm that this is a suitable area for the PEG tube 112 to be inserted. The gastric wall lights up where the magnet is located. This is where the needle 106 will enter the stomach as it goes through the guide channel 126 of the sensor device 118.

An examiner may optionally also use a finger to palpate the abdomen to determine whether the endoscopist can see the indentation, as in the standard practice. If everything looks satisfactory, a small incision is made in the skin, and a needle 106 is inserted into the guide channel 126 in the sensing device 118 through the ring of lights 136. This channel 126 controls the direction of the needle 106 and assures that the direction is orthogonal to the bottom 130 of the sensing device 118 and the ring of lights 136.

Figure 14D:
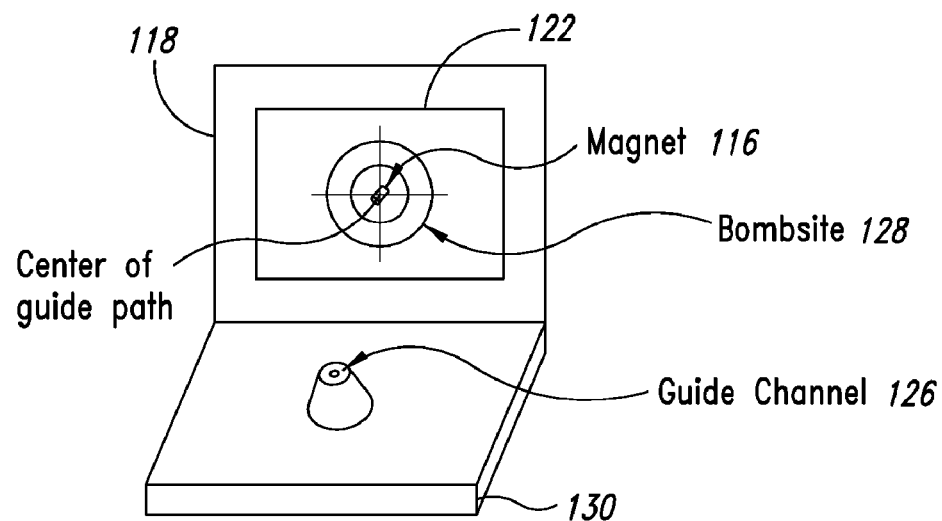
FIG. 14D shows a screen on a sensing device indicating position and depth of a magnet, and the sensing device has a target guide for the guide path of the needle to inform the operator that if the needle is placed into the guide channel and advanced via the guide channel, the needle tip will approach the magnet in accordance with one embodiment.

As shown in FIG. 14D, a guide path on the high resolution screen 122 informs the examiner that by directing the needle 106 along the needle guide channel 126 in the center of the ring a lights 136, and to the indicated depth, the needle 106 will enter the gastric lumen in the substantially precise location of the magnet 116.

In one embodiment, the needle 106 will enter the gastric lumen within several millimeters or even less distance from the magnet 116. When the needle 106 is advanced the desired distance, if an endoscopist is observing, the endoscopist will see the needle 106 enter the stomach via the wall substantially at the location selected.

The distance from the skin to the gastric wall, which is not known with traditional PEG techniques, is determined from the outside with substantial precision by "seeing" the magnetic element on the magnetic nasogastric tube initially and then after the balloon is inflated with the magnet in the center (in embodiments where a balloon is used). That is, the magnetic detection sensor device will provide a medically accurate distance measurement from the sensor to the magnetic element of the magnetic nasogastric tube and to the gastric mucosa.

Referring back to FIG. 13, if the distance is measured after the balloon 124 is inflated and if the magnet 116 is in the center of the balloon 124, the distance from the skin to the gastric mucosa is the distance to the magnet 116 minus the known distance B from the wall of the balloon 124 to the magnet 116. Alternatively the balloon 124 may not be around the magnet 116 but just behind the magnet 116

(towards the mouth) or no balloon may be used and the stomach simply inflated with air or fluid via the magnetic nasogastric tube 114.

Figure 15:
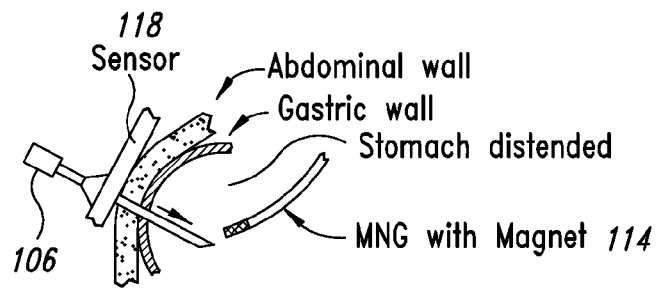
FIG. 15 shows the needle inserted to the measured distance as determined by the magnetic detector according to an embodiment.
Figure 16:
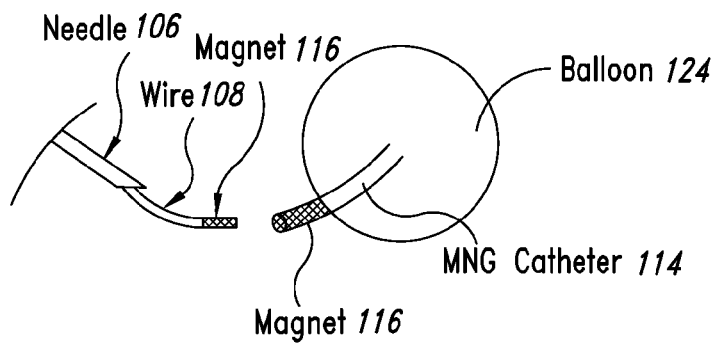
FIG. 16 shows a medical wire with a magnet on the tip is inserted through the needle close to the magnet on the magnetic nasogastric tube according to an embodiment.

Additional elements in the new approach to placing a magnetic nasogastric tube 114 are shown in FIGS. 15 and 16. In FIG. 15, the needle 106 is inserted in a direction and to a depth as indicated on the magnetic detection sensor device 118. Unlike traditional PEG tube placement, where an endoscopist watches the needle 106 enter the stomach 100, seeing the needle 106 enter the stomach 100 in one embodiment of the new percutaneous magnetic gastrostomy approach is not needed because the stomach 100 is inflated using the magnetic nasogastric tube balloon 124 (or inflated with a side port of the magnetic nasogastric tube not the balloon), and the magnetic detection sensor device 118 provides a sufficiently accurate location to which a needle 106 will travel.

In FIG. 16, a wire 108 with an element 116 having magnetic properties at its distal end is inserted into the needle 106 and placed very close to the magnetic element 116 on the magnetic nasogastric catheter 114. In some embodiments, the wire 108 has a strong magnet 116 secured to its distal end. Due to the precision of the magnetic sensor device 118, the wire 108 will be directed to the location of the magnetic element 116 on the magnetic nasogastric tube 114.

Figure 17:
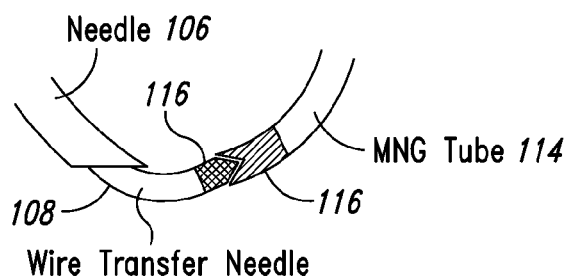
FIG. 17 shows the two magnets sticking together according to an embodiment.

As shown in FIG. 17, when the magnetic elements 116 of the magnetic nasogastric tube 114 and the wire 108 are in proximity, the elements will mutually attract and be coupled together to form a permanent or impermanent junction. A snare to grasp the wire is not needed because the magnet-to-magnet attraction firmly holds the needle wire 108 against the magnetic nasogastric tube magnetic element 116. Similarly, the endoscope to pull out the snare holding onto the needle wire is not necessary because the magnet-to-magnet junction will pull out the needle wire 108 as either the magnetic nasogastric tube 114 is pulled out or the magnet-to-magnet junction is pulled out of a lumen of the magnetic nasogastric tube 114.

In some embodiments the magnetic nasogastric tube and needle wire may interlock together to assure that magnets stay coupled as the wire is withdrawn.

Figure 18:
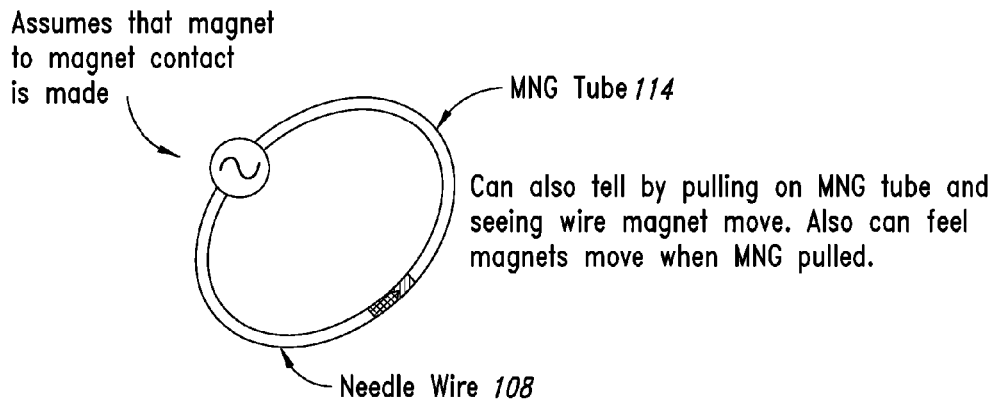
FIG. 18 shows an electric current facilitating a determination that the two magnets are touching according to an embodiment.

In some embodiments, the magnetic nasogastric tube 114 is formed such that the magnetic nasogastric tube 114 or one of its components will conduct a small electric current. As shown in FIG. 18, for example, a small electric current may be introduced onto the wire 108 or magnetic nasogastric tube 114. The small current is then detected by the medical practitioner on a current gauge to indicate that the wire 108 and the magnetic nasogastric tube 114 have made physical contact with each other. The small electrical current (having very low voltage for safety) is just enough to let the medical practitioner know that the two magnets have touched. In other embodiments, physical contact is indicated by expressly moving either the wire 108 or the magnetic nasogastric tube 114 and noticing a corresponding motion on the other component.

Figure 19:
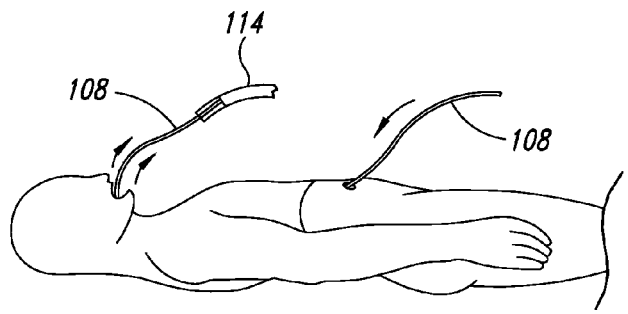
FIG. 19 shows a magnet-to-magnet junction being removed from the patient through the nasogastric tube or with the magnetic nasogastric tube according to an embodiment.

After the magnetic nasogastric tube 114 and the wire 108 have been joined, the wire 108 is advanced through the needle 106 or the hole made by the needle 106 until it passes out through the patient's mouth. As shown in FIG. 19, the magnetic nasogastric tube 114 may be removed from the patient thus pulling the magnet-to-magnet junction with it, or, in alternative embodiments, the magnet-to-magnet junction may also be pulled out via the lumen of the magnetic nasogastric tube 114.

Once the magnet-to-magnet junction is out of the patient's mouth, more wire 108 is pulled through the needle 106 or the hole made by the needle 106 if the needle has been backed out. This creates a situation where the wire 108 entering the hole made by the needle 106 or through the needle 106 is now firmly held outside the patient's mouth. If the magnetic nasogastric tube 114 was removed from the patient, then the magnetic nasogastric tube 114 is removed from the wire 108. If the wire 108 was passed via a lumen on the magnetic nasogastric tube 114, then alternate embodiments allow for the magnetic nasogastric tube 114 to either be removed from the patient or left in place. In some embodiments, the end of the wire 108 extending from the patient's mouth is then attached to the end of the PEG tube. In other embodiments, the PEG tube is placed over the wire 108.

Figure 20A:
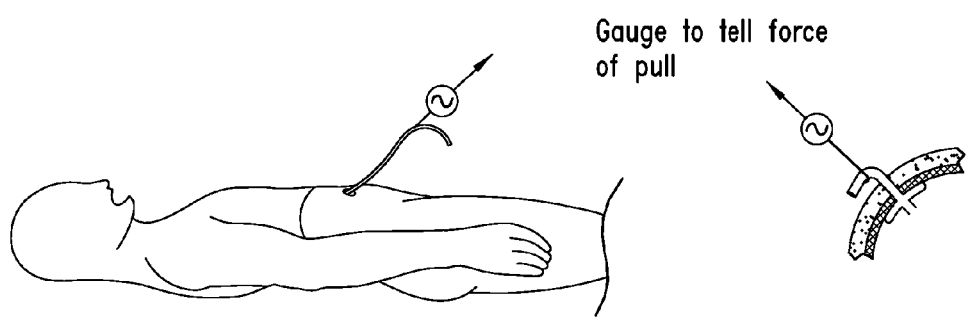
FIG. 20A shows that correct force is being used to pull the PEG tube up against the gastric mucosa, and the PEG tube is being secured in place according to an embodiment.
Figure 20B:
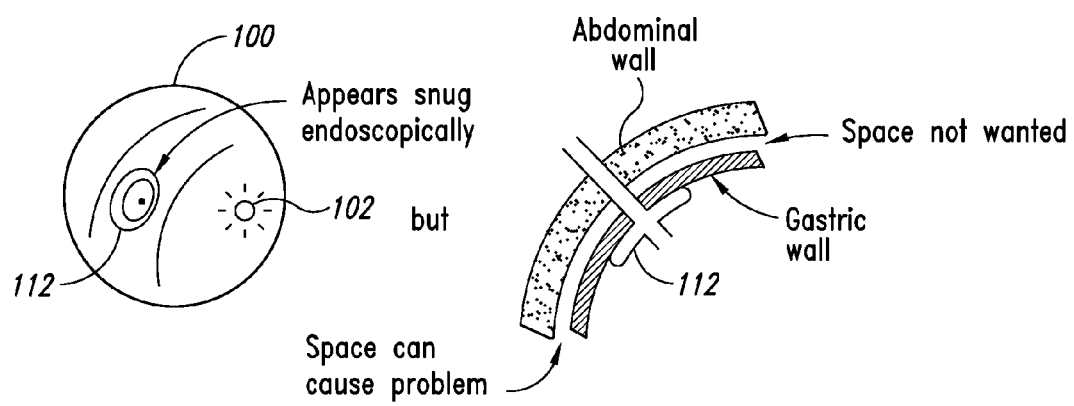
FIG. 20B shows that the bumper looks snug endoscopically, but the gastric mucosa is not up against the abdominal wall according to an embodiment.

As shown in FIG. 20A, the PEG tube is then pulled into the stomach and up against the gastric mucosa. Sufficient pulling force is used to assure that the bumper of the PEG tube is firmly against the mucosa. In some embodiments, a separate gauge or metering device 138 is used to determine that a suitable force is exerted on the wire to appropriately seat the PEG tube. Final inspection of the PEG bumper with an endoscope or x-ray is not needed because a pressure range is given and perhaps measured with a small force measuring device 138 to assure that the bumper is snug against the wall. This pressure measurement is likely a better way to know that the bumper is in the correct place and snug then is endoscopy. For example, as shown in FIG. 20B, if the bumper looks to be in the correct place by endoscopy, this means that even though the tube's bumper is on the mucosa, it is still possible that there is excessive tube between the skin and the outside of the stomach. By knowing the pressure pulling the bumper against the mucosa, a medical practitioner can be sufficiently confident that the bumper is snug and is up against the abdominal wall.

As described in the non-limiting embodiments herein, endoscopy is not necessary when the new approach to percutaneous magnetic gastrostomy placement is used. For many similar reasons, x-ray is also not necessary. For example, the location of the stomach is determined by passing the magnetic nasogastric tube into the stomach (for instance approximately 50 cm from the incisor teeth for a typical adult patient), seeing the magnet in the left upper quadrant (LUQ) of the abdomen, and determining the distance from the magnetic element on the magnetic nasogastric tube to the skin before and after the stomach is inflated, with or without a balloon.

In the embodiments described above, a PEG tube can be placed safely and quickly into the stomach without either an endoscope or x-ray. With the magnetic detection sensor device, distances are clearly known and the targeting of the needle to the tip of the magnetic nasogastric tube (with the magnetic element) is facilitated. The medical practitioner substantially knows the distance to the gastric mucosa, and the substantially precise X, Y, Z location of the tip of the magnetic nasogastric tube. Further, an embodiment of the magnetic detector has a needle guide and/or a bomb site type visual guide to enable the medical practitioner who is inserting the needle to know where to insert the needle tip and the depth necessary to contact the magnet on the tip of the magnetic nasogastric tube. The magnet-to-magnet attachment removes the need for a snare and an electrical current detector may be used to assure that contact is made between the two magnetic elements.

B. Additional Methods for Using a Magnetic Nasogastric Tube

Additional non-limiting and non-exhaustive embodiments for the use of a magnetic nasogastric tube for single pass gastrostomy, from the outside to the inside, are now described with reference to FIGS. 21-28.

Figure 21:
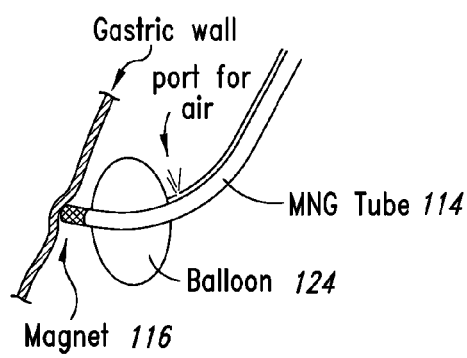
FIG. 21 shows the magnetic nasogastric tube placed into the stomach, inflating the stomach with a balloon on the tip, and the magnet is pushed against the gastric wall according to an embodiment.

In some embodiments, a magnetic nasogastric tube 114 is passed into the stomach. The stomach is inflated, for example with about 300 cc of air and a balloon 124 inflated on the magnetic nasogastric tube 114. In some embodiments, it may not be necessary to use or inflate the gastric balloon 124. Generally, the purpose of the gastric balloon 124 is to provide some confidence that the tip of the magnetic nasogastric catheter 114 is freely mobile. The magnetic nasogastric tube 114 is then pushed against the gastric wall as shown in FIG. 21.

Figure 22:
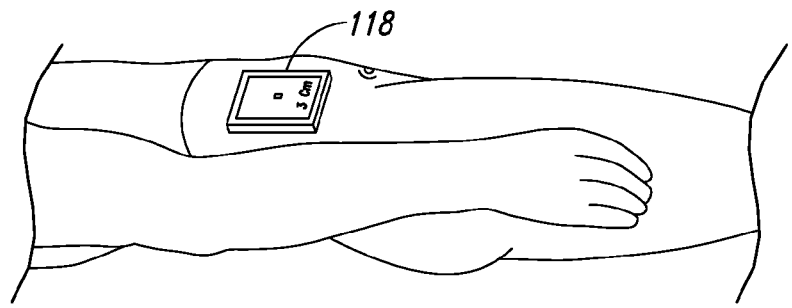
FIG. 22 shows the magnetic detection sensor device determining the distance and location of the magnet on the tip of the magnetic nasogastric tube according to an embodiment.
Figure 23:
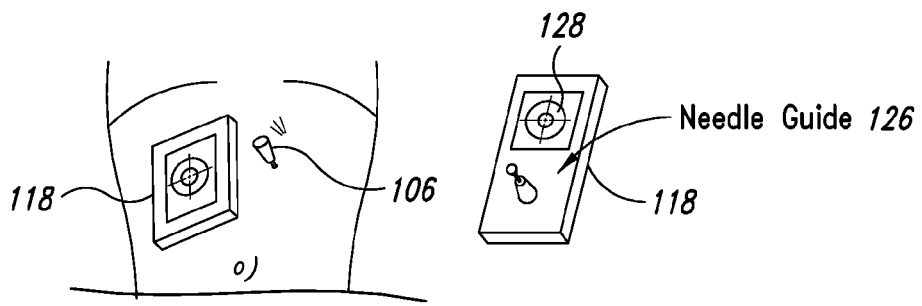
FIG. 23 shows a needle being passed towards the magnet on the magnetic nasogastric tube by using information presented on the magnetic sensor device according to one or more embodiments; in one embodiment a bomb site is used to direct the tip; in another embodiment, a needle guide is used to assure the path of the needle to the magnet; in each embodiment, the direction and the distance is known from the magnetic sensor device.

As shown in FIGS. 22 and 23, a magnetic detection sensor device 118 is then placed on the skin to determine the distance from the skin to the magnet 116 that is on the tip of the magnetic nasogastric tube 114. If this distance is considered suitable by the medical practitioner, for example, 3 cm, a needle 106 is inserted into the abdominal wall towards the magnet 116 on the tip of the magnetic nasogastric tube 114. The needle 106 may be guided by a bomb site 128 on the magnetic detection sensor device 118 and/or a needle guide 126, which provides medical assurance that the needle 106 is directed to the zone identified by the bomb site 128. In some embodiments, the needle 106 is formed as a trocar. In some embodiments, the needle or trocar is sharp; in some embodiments, the needle or trocar is dull.

Figure 24:
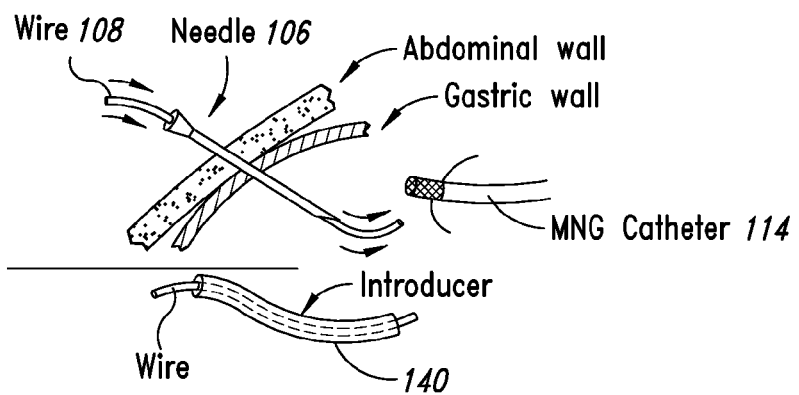
FIG. 24 shows an introducer being passed over the needle or over a wire passed via the needle according to an embodiment.

FIG. 24 shows another step in the new procedure for single pass gastrostomy, from the outside to the inside. Once the needle 106 is in place, a catheter/introducer 140 is passed from the skin into the stomach. In some embodiments, a wire 108 is passed through the needle 106 and the wire 108 guides the introducer 140. In some embodiments, the needle 106 acts as the wire 108 and guides the introducer 140. The tip of this catheter/introducer 140 is tapered or sharp and is passed to the depth indicated by the magnetic detection sensor device 118.

Figure 25:
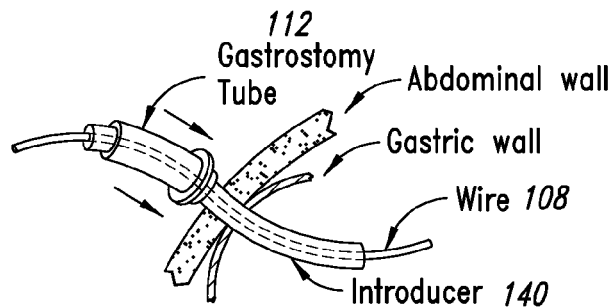
FIG. 25 shows the gastrostomy tube being passed over the introducer according to an embodiment.
Figure 26:
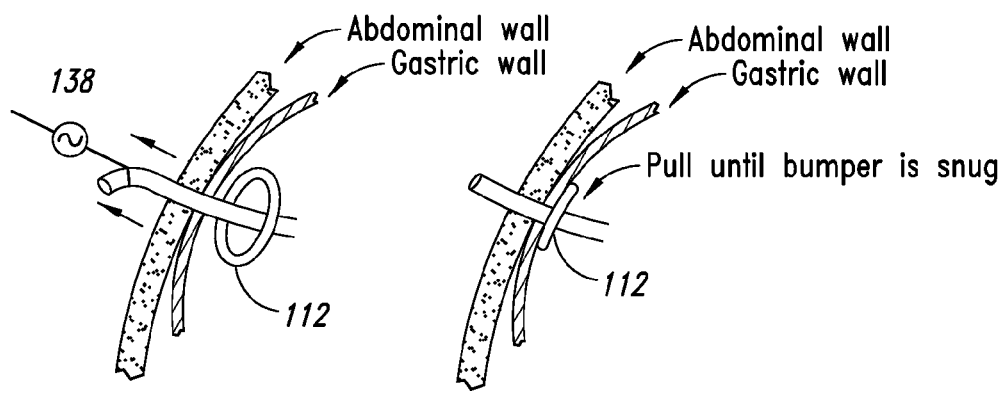
FIG. 26 shows the wire or needle and the introducer being backed out, and the gastrostomy tube left in place after a strain gauge was used to measure pull back force to assure that the bumper was snug according to an embodiment.
Figure 27:
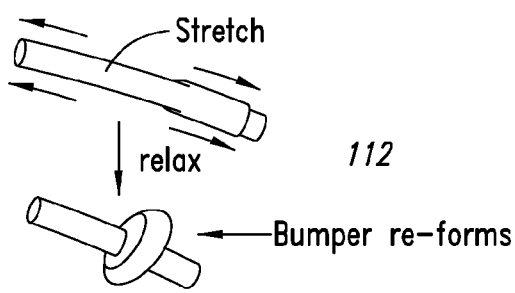
FIG. 27 shows the bumper being compressed and stretched as it is introduced, and once in the gastric lumen, it is released and reassumes its shape as a bumper according to an embodiment.

Additional steps in the new procedure for single pass gastrostomy, from the outside to the inside, are shown in embodiments in FIGS. 25-27. A gastrostomy tube 112 with a rubber or silicon bumper is passed over the sharp introducer 140 until it enters the stomach. The bumper may be compressed as the gastrostomy tube 112 is pushed into position through the gastric wall and when the bumper is inside the stomach, the compressing force is released and the bumper re-assumes its shape as a bumper. When the bumper is in position, the sharp or dull trocar, needle, and/or wire placed via the needle are removed. The gastrostomy tube 112 may then be pulled back with a suitable pulling force. In some embodiments, a stress measuring gauge 138 is used to measure a suitable pressure on the bumper of the gastrostomy tube 112. The gastrostomy tube 112 is then secured in place.

In some embodiments, when the sharp introducer 140 is advanced to the depth indicated by the magnetic sensor device 18 plus, for example, an additional 1 cm, the sharp part is removed leaving a cylindrical introducer with a blunt end over which the gastrostomy catheter is placed. This would prevent injury from the sharp introducer 140 as the gastrostomy tube 112 is pushed into position. When the tip of the gastrostomy tube 112 and the bumper are in the gastric lumen the cylindrical introducer 140 can be removed. The gastrostomy tube 112 is then pulled back perhaps using a strain gauge 138 to get the bumper snugly against the gastric wall.

Figure 28:
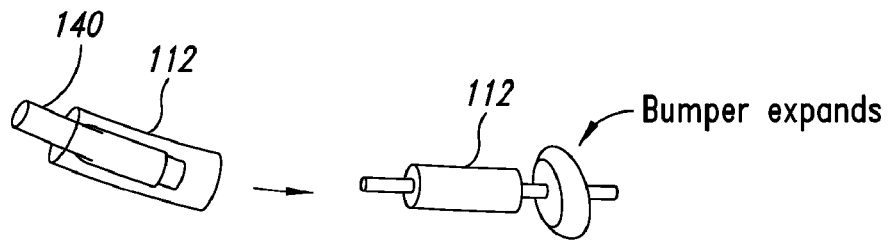
FIG. 28 shows the gastrostomy tube with the stretched bumper being passed down the lumen of the introducer; and after advancing into the stomach, the "stretch" is relaxed, and the bumper forms its shape and can be pulled upon to snugly come up against the gastric mucosa according to an embodiment.

In some embodiments, for example as shown in FIG. 28, the gastrostomy tube 112 with the bumper is passed down the lumen of the introducer 140 with the sharp needle/trocar removed. The gastrostomy tube 112 is stretched so that the bumper closes like an umbrella. Once the gastrostomy tube 112 is in the stomach, the stretching force is relaxed, and the gastrostomy tube 112 will re-assume its shape with the bumper. The cylindrical introducer may then be removed and the gastrostomy tube attached as described herein.

C. A New Magnetic Nasogastric Tube

Additional non-limiting and non-exhaustive embodiments of the new type of nasogastric (NG) tube, the magnetic nasogastric (MNG) tube 114, and procedures for using the magnetic nasogastric tube 114 are now described and shown in FIGS. 29-41. Each of the embodiments described or shown are put forth to present a clearer picture of the magnetic nasogastric tube 114 and procedures, but none of the embodiments alone or in any combination limit the magnetic nasogastric tube and procedures to only that which is shown or described. It is noted that particular features of the magnetic nasogastric tube 114 and procedures shown and described, along with particular structures, components, or methods, are merely provided to present the magnetic nasogastric tube 114 and procedure in a convenient and understandable manner.

Figure 29:
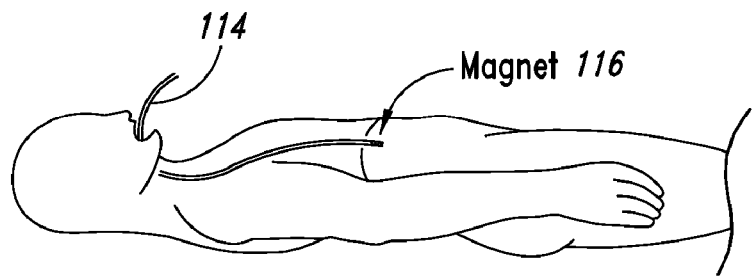
FIG. 29 shows a magnetic nasogastric (MNG) tube is being passed into the stomach according to an embodiment.
Figure 30:
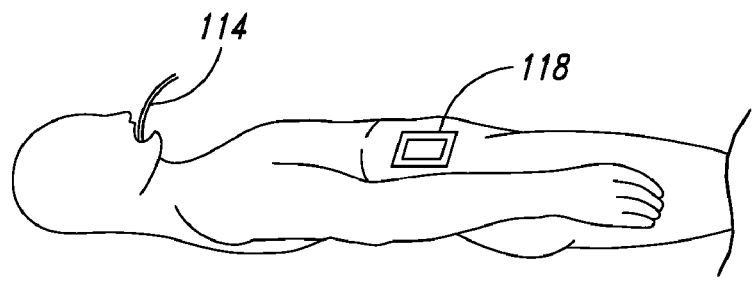
FIG. 30 shows the magnetic detector being placed over the left upper quadrant (LUQ) in a spot suitable for a gastrostomy to exit the skin of the abdominal wall according to an embodiment.
Figure 31:
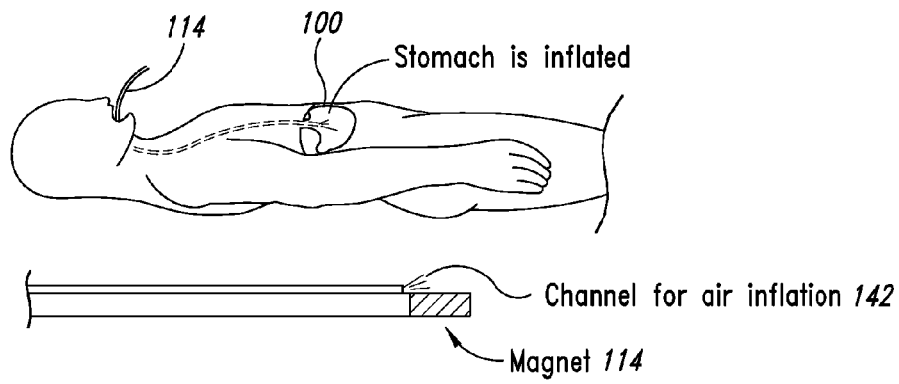
FIG. 31 shows the stomach being inflated via a channel of the magnetic nasogastric tube according to an embodiment.

Embodiments of a single pass tube are used and designed as follows. As shown in FIG. 29, the patient lies supine, and a magnetic nasogastric tube 114 is passed by a medical practitioner approximately 50 cm from the incisor teeth down the esophagus into the stomach. The distance is sufficient to place the distal end of the magnetic nasogastric tube 114 into the stomach of the particular patient. The magnetic nasogastric tube 114 has a magnet 115 at the tip. As shown in FIG. 30, a magnetic detection sensor device 118 is placed over the skin in the LUQ of the abdomen just below the ribs, in a spot suitable for the gastrostomy tube placement. As shown in FIG. 31, the stomach 100 is then inflated with air or another substance placed via an optional channel 142 in the magnetic nasogastric tube 114. In some embodiments, a total of about 300 cc is passed.

The magnetic nasogastric tube, which was advanced gently through the patient's mouth and into the stomach, has a magnet 116 on the tip. The magnetic detection sensor device 118 then is used to detect the presence of the tip of the magnetic nasogastric tube 114 by locating the tube's magnet 116.

Figure 32:
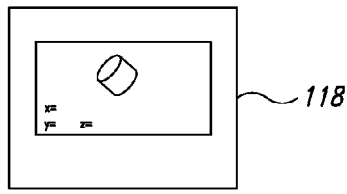
FIG. 32 shows the magnetic detector locating the magnet and determining its orientation and distance to the skin according to an embodiment.

As shown in FIG. 32, the magnetic detection sensor device 118 can also tell the current orientation of the tip of the magnetic nasogastric tube 114 to determine when the tip of the tube is pointed directionally at the magnetic detection sensor device 118. The magnetic nasogastric tube 114 is then gently manipulated and the magnetic detection sensor device 118 quantifies the distance from the magnetic detector 118 to the tip of the tube 114. At this stage of the procedure, the medical practitioner substantially knows the location of the tip of the magnetic nasogastric tube 114, the orientation of the magnetic nasogastric tube 114, and the distance from the skin to the tip of the tube 114.

Figure 33:
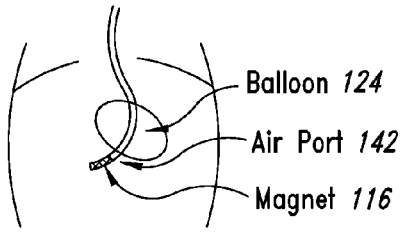
FIG. 33 shows the magnetic nasogastric tube having a balloon, which can be inflated to determine that the area of the magnet is distensible freely; low pressure inflation is used to prevent injury and to be sure that inflation is easy at low pressure according to an embodiment.

Next, as shown in FIG. 33, a balloon 124, may be inflated. In some embodiments, the balloon is formed such that it is attached to the magnetic nasogastric tube 113 just above the magnet 116 and the air inflation port 142. This balloon 124 may have, for example, a volume of about 100 cc. If the balloon 124 inflates easily, the medical practitioner sufficiently knows that the tip of the magnetic nasogastric tube is in a free portion of the stomach.

The continued inflation of the stomach, to a volume of 300 cc for example, may also indicate that the stomach is the site of the distal end of the magnetic nasogastric tube 114. In some embodiments, it may not be necessary to use a balloon on the end of the magnetic nasogastric tube 114.

Figure 34:
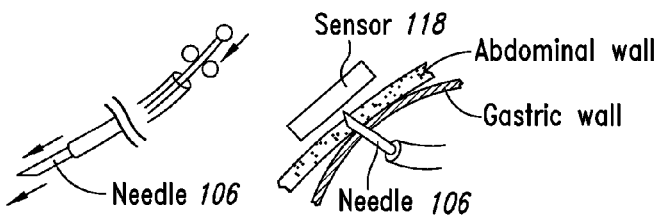
FIG. 34 shows a plunger being used to advance the needle towards the magnetic detection sensor device according to an embodiment.

In some embodiments, the magnetic nasogastric tube 114 is formed such that a sharp needle 106 embedded in the tip of the magnetic nasogastric tube 114 may be advanced or retracted at a suitable time by the medical practitioner. For example, FIG. 34 shows that if the distance, orientation of the tip, and location on the abdominal wall is satisfactory (for example 3 cm, pointing towards the sensor, LUQ 4 cm below rib margin) and the magnetic nasogastric tube 114 is pushed gently against the gastric mucosa, then a special plunger 144 on the proximal end (i.e., the end still outside the patient) of the magnetic nasogastric tube 114 may be advanced and a sharp needle 106 advances out of the distal tip of the magnetic nasogastric catheter 114, moves through the gastric and abdominal walls, and exits the skin where the detector 118 noted the magnetic signal.

Figure 35:
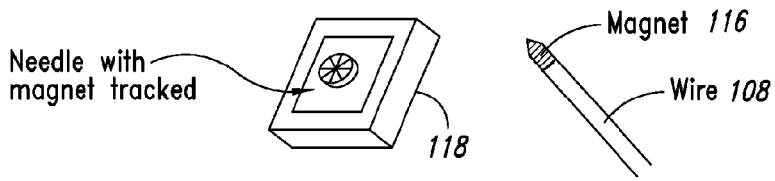
FIG. 35 shows the magnet on the tip of the needle being watched as it moves towards the magnetic sensor according to an embodiment.

In some embodiments, as shown in FIG. 35, the magnet 116 may be placed on the tip of the needle 106 or the needle 106 may be formed from a material having magnetic properties so the examiner can watch the needle 106 as it exits the magnetic nasogastric tube 114 and moves towards the sensor 118 from the inside of the stomach. In some embodiments, the needle is a trocar.

Figure 36:
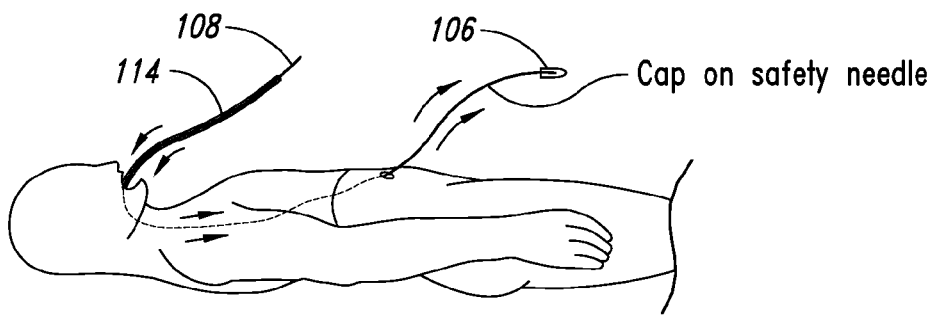
FIG. 36 shows the sharp tip of the needle is covered, and the needle being pulled away from the skin pulling more of the medical wire behind the needle with it according to an embodiment.

FIG. 36 shows that the sharp tip may then be covered for safety and the needle pulled out of the skin. In some embodiments, when the needle 106 is pulled, it will thereby pull more of the wire 108 that was used as a plunger 144 to push the needle 106. In other embodiments, a separate wire 108 may be advanced down the magnetic nasogastric tube 114 and either exit the lumen of the needle 106 or be funneled through a lumen in the trocar.

Figure 37:
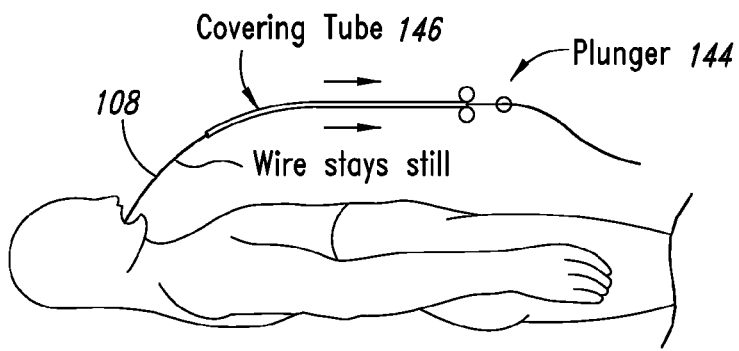
FIG. 37 shows the plunger and covering tube of the magnetic nasogastric tube (with the deflated balloon if the catheter has a balloon) being removed leaving the wire that was used to push the needle according to an embodiment.

Another step is shown in FIG. 37 where the plunger advancer 144 and the covering tube 146 part of the magnetic nasogastric tube 114 is removed from the patient leaving behind the wire 108 and the sharp needle/trocar 106. This leaves the wire from the skin of the abdomen to the mouth.

Figure 38:
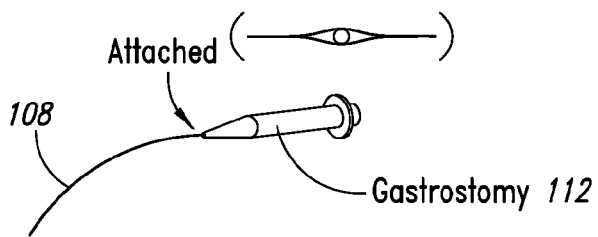
FIG. 38 shows the wire attached to the tapered tip of the gastrostomy tube according to an embodiment.
Figure 39:
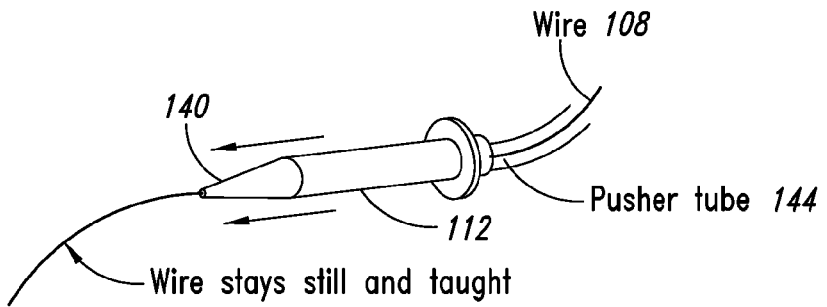
FIG. 39 shows the tapered end of the gastrostomy tube being passed into the stomach over the wire and allowing the wire to act like a guide wire when the gastrostomy tube is pushed using a pusher tube according to an embodiment.

FIG. 38 shows a wire 108 attached to a tapered end of a gastrostomy tube 112. In some embodiments, the wire 108 is then manually attached to the sharp, tapered introducer tip of a gastrostomy tube 112; in other embodiments, the gastrostomy tube 112 is attached during manufacture. In still other embodiments, as shown in FIG. 39, the tapered introducer 140 of the gastrostomy tube 112 is placed over the wire 108 thereby using the wire 108 as a guide wire.

Figure 40:
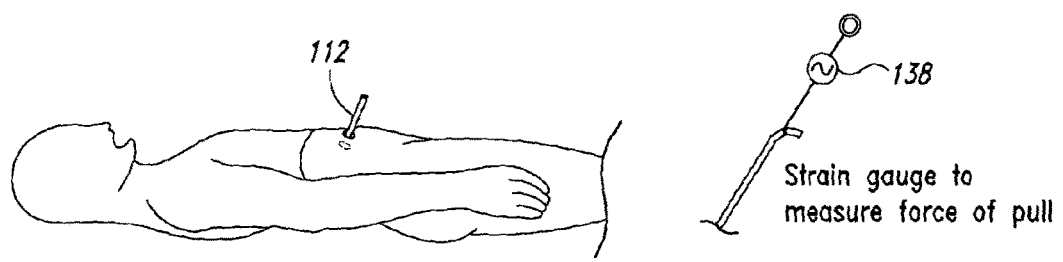
FIG. 40 shows the gastrostomy tube being pulled into position and a strain gauge used to measure a suitable amount of pulling force on the gastrostomy tube to assure a snug fit according to an embodiment.

In some embodiments where the gastrostomy tube is attached to the wire, FIG. 40 shows that the PEG tube 112 is then pulled through the mouth, down the esophagus, into the stomach, and then through the gastric and abdominal walls into a suitable position where it is secured. In some embodiments, a strain gauge 138 determines the proper pulling force for the tube 112. In these embodiments, the wire is removed from the patient as the tube is pulled into the stomach and through the abdominal wall.

Figure 41:
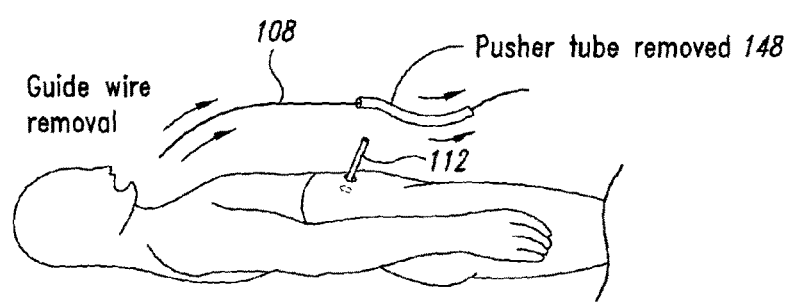
FIG. 41 shows the pusher tube being removed with the guide wire when the gastrostomy is in place according to an embodiment.

Another embodiment is shown in FIG. 41 in situations where the gastrostomy tube 112 is threaded on the wire 108. In these situations, a "pusher tube" 148 is also threaded on the wire and the gastrostomy tube is pushed down the mouth, esophagus, and stomach and out over the wire until it exits the abdominal wall and can then be pulled into position, quantified in terms of pull, and then secured. In this instance the pusher tube 148 is subsequently removed back over the guide wire 108. In some embodiments, the guide wire 108 can be removed with the pusher 148 or after the pusher 148 is removed. The guide wire 108 can be removed via the mouth or via the skin of the abdomen, by pulling it through the gastrostomy tube 112.

In some other gastrostomy tube placement procedures, the tube 112 is pressed from the outside of the abdomen, through a hole in the abdomen, and into the stomach. In some cases, the end of the gastrostomy tube 112 may problematically not be fully passed into the stomach. However, in the embodiments described herein, where the gastrostomy tube 112 is pulled or pushed via the mouth into the stomach, the medical practitioner can be medically confident that the bumper is in the stomach and not in the tissue between the stomach wall and the skin because the bumper is pulled into the stomach via the mouth instead of being pushed into the stomach from the outside of the abdominal wall.

D. Additional Embodiments of a Magnetic Nasogastric Tube

Additional non-limiting and non-exhaustive embodiments using the new equipment and new procedures are shown in FIGS. 42-50 and described below. In some embodiments, when a gastrostomy guide wire is to be passed from the inside of the stomach through the gastric and abdominal walls to the outside, some additional features of the equipment or procedure may be used.

Figure 42:
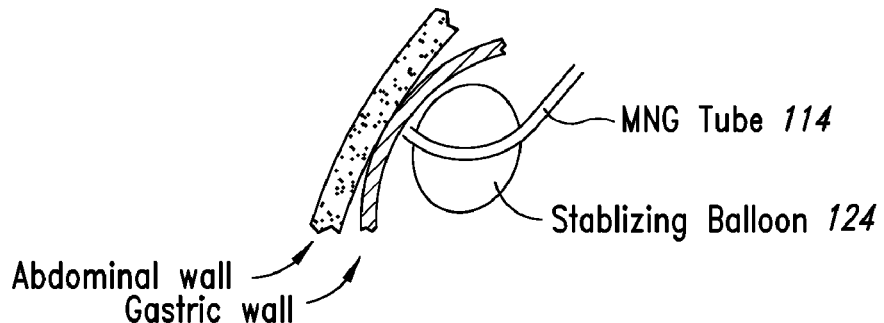
FIG. 42 shows a balloon orienting the tip of the magnetic nasogastric tube according to an embodiment.

For example, an embodiment is shown in FIG. 42 where a balloon 124 helps maintain the orientation of the tip of the magnetic nasogastric tube 114 so that the needle 106 will exit in the direction desired and selected from the outside.

Figure 43:
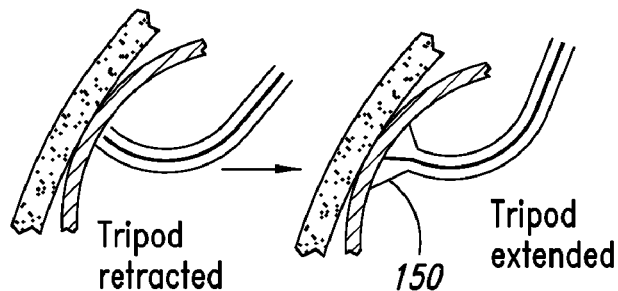
FIG. 43 shows a tripod opening to orient the tip of the magnetic nasogastric catheter according to an embodiment.

In another embodiment, shown in FIG. 43, a tripod 150, which opens when extended from the catheter 114, may keep the tip of the magnetic nasogastric tube 114 orthogonal to the mucosa.

Figure 44:
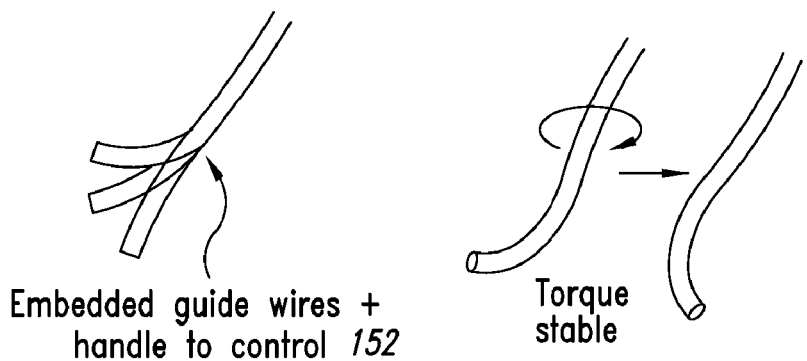
FIG. 44 shows controllable guide wires bending the tip of a magnetic nasogastric tube in the desired direction; torque stability allows the orientation of the tip of the magnetic nasogastric tube to be controlled by rotating the tube at the patient's mouth according to an embodiment.

Another embodiment of a magnetic nasogastric tube 114 is shown in FIG. 44 where the end of the magnetic nasogastric tube 114 may be controllable with guide wires 152 to move the tip or with a small built in curvature and torque stability so that rotation of the tube 114 will move the tip in a different direction. In some embodiments, an indexing mark on the tube, visible at the patient's mouth, allows the orientation of the tube in the patient's stomach to be known.

Figure 45:
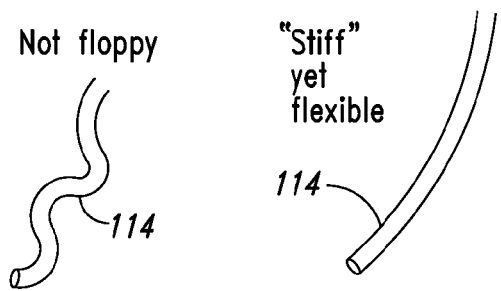
FIG. 45 shows the magnetic nasogastric tube is not "floppy" but can be sufficiently stiff to allow passage of the needle and wire according to an embodiment.

FIG. 45 shows an embodiment where the magnetic nasogastric tube 114 will be somewhat stiff so it is controllable and so that it is not "floppy."

This is important for orientation and so that the needle 106 can be extended from the tip of the tube 114 and through the wall of the stomach and abdomen.

Figure 46:
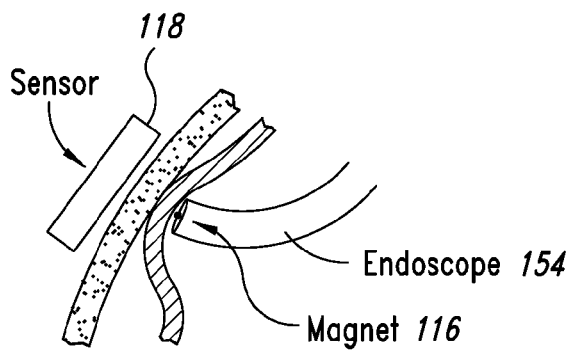
FIG. 46 shows an endoscope directing the tip of the needle in the desired direction and providing the stiffness needed to advance the needle; the endoscope can select the site on the mucosa of the stomach (guided by the magnetic sensor on the outside; and the endoscope can also be pushed against the mucosa to facilitate passage of the needle according to an embodiment.

It is shown in FIG. 46 that while unnecessary for the procedures described herein, an endoscope 154 may be used in some embodiments to facilitate placement of the gastrostomy tube 112. For example, an endoscope 154 can pick a spot on the wall and hold in the correct direction the end of the magnetic nasogastric tube 114, when the magnetic nasogastric tube 114 is passed via one of the endoscope channels. In this way the needle 106 may be substantially aimed at the site selected from the outside with the aid of a magnetic detection sensor device 118. The endoscope 154 can also be pressed against the mucosa and aimed in the desired direction.

A magnetic element 116 may be placed on the end of the needle 106 or on the end of the magnetic nasogastric catheter 114 used to pass the needle 106. This catheter 114 is thus also useful to protect the patient from the needle's sharp end as the needle 106 is passed through the esophagus into the stomach or to protect the endoscope 154 as the needle 106 is passed via the biopsy channel of the endoscope 154.

Figure 47:
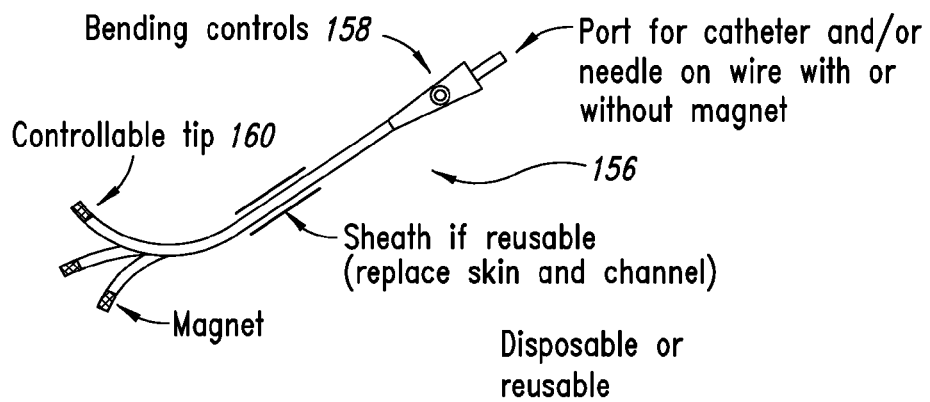
FIG. 47 shows an embodiment of a guide tube.

An embodiment is shown in FIG. 47 where a controllable guide tube instrument 156 has some of the features of an endoscope 154, but which is not an endoscope 154. The controllable guide tube instrument 156 may be used to guide the magnetic nasogastric tube 114 having a magnetic element 116 and in some embodiments, a needle 106. This new instrument 156 can be similar to an endoscope 154 but without suction, without optics, without irrigation, and without light. It can be a somewhat stiff tube with armor; flexible, and with a channel 164 for the magnetic nasogastric tube 114.

This controllable guide tube 156 can have a sheath 162 and a removable channel 164 so that when the sheath 162 and the channel 164 are removed and replaced, the next patient has a sterile guide tube 156 free of contamination from the previous patient. In addition or in alternative to the features stated above, some embodiments of the controllable guide tube 156 may have an optional stabilizing balloon 124.

Embodiments of the controllable guide tube instrument 156 would be far less expensive than an endoscope 154, and in some embodiments this tube 156 might be reusable using a sheath 162. In some embodiments, the controllable guide tube instrument 156 might be disposable and made out of simple materials at low cost. In some embodiments, the guide tube 156 can also be made out of materials that can be cleaned and then sterilized with vapor, liquid, or steam sterilization.

Figure 48:
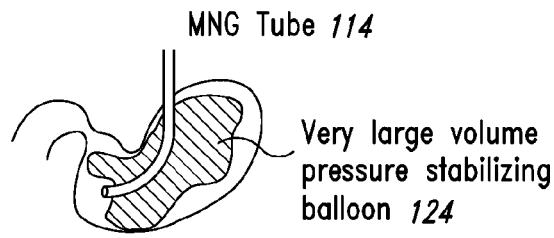
FIG. 48 shows a large balloon stabilizing the tube tip by filling up the stomach transiently until a needle is passed according to an embodiment.
Figure 49:
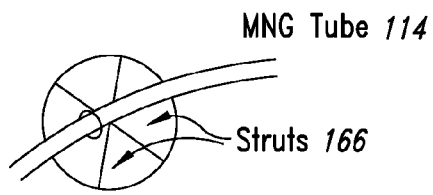
FIG. 49 shows a balloon with an internal structure to assure uniform inflation according to an embodiment.

FIGS. 48 and 49 show other embodiments of a magnetic nasogastric tube 114 that have a balloon 124 attached. In some situations, it may be useful to use a very large volume balloon 124 to stabilize the tip of the magnetic nasogastric tube 114 by filling up the volume of the stomach. This may help to provide stability as the needle 106 is passed through the gastric wall and abdominal wall to the outside of the skin. In other situations, the medical practitioner may have increased assurance that the area selected is expandable and free of other structures, by using a magnetic nasogastric tube 114 having a balloon 124 that includes an internal structure 166 formed so as to assure that the balloon 124 inflates uniformly in all directions and with part of the structure located in a known and suitable location relative to the balloon 124.

Figure 50:
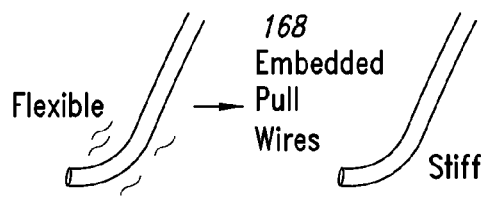
FIG. 50 shows that the guide tube is flexible, but when in position, wires are pulled and the guide tube guiding the magnetic nasogastric tube, magnet, and needle for insertion becomes stiff to facilitate keeping the magnetic nasogastric tube in position, which helps passage of the needle according to an embodiment.

In some embodiments, as shown in FIG. 50 for example, if a magnetic nasogastric catheter 114 is used to pass a needle 106 from the inside of the stomach to the outside of the abdominal wall, it may be useful to use a catheter 114 which is flexible when passed into the patient's body, but when in position to pierce the gastric and abdominal walls, the catheter 114 can be made rigid. In some embodiments, the magnetic nasogastric catheter 114 is formed with the use of wires 168 embedded in the tube's walls. These wires 166 may further assist in keeping the orientation of the tip of the catheter 114 and facilitating passing the needle 106 through the gastric and abdominal walls to the outside of the skin.

E. Embodiments of a Controllable Magnetic Nasogastric Tube

Additional non-limiting and non-exhaustive embodiments of a new type of nasogastric (NG) tube, a controllable magnetic nasogastrostomy (MNG) tube, and procedures for using the controllable magnetic nasogastric tube 114 are now described and illustrated in FIGS. 51-56.

Figure 51:
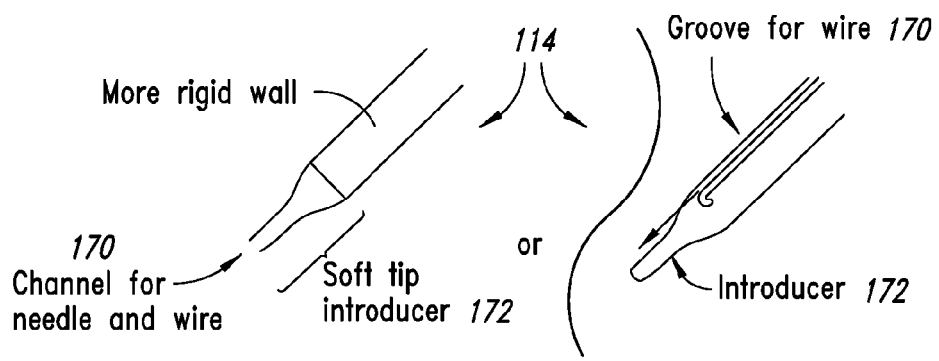
FIG. 51 shows a soft introducer tip for a controllable magnetic nasogastric tube having a groove for a guide wire and a magnetic nasogastric tube having a channel for a guide wire according to an embodiment.

In some embodiments, as shown in FIG. 51, the controllable magnetic nasogastric tube 114 will have one or more of the features of a diameter about 8 mm or 24 French, a flexible but not floppy constitution, a formation which is stable with regards to torque such that the tube may be operatively turned from one end and maintain the same turning component throughout a suitable length of the tube, a channel or groove 170 for a guide wire embedded in the controllable magnetic nasogastric tube or formed on the side of the controllable magnetic nasogastric tube 114, a soft introducer tip 172, an exit for the channel at very tip of the controllable magnetic nasogastric tube, an exit for the channel that is parallel with the soft introducer tip, a biopsy channel to introduce a wire or gas, and a suction channel to remove gas.

Figure 52:
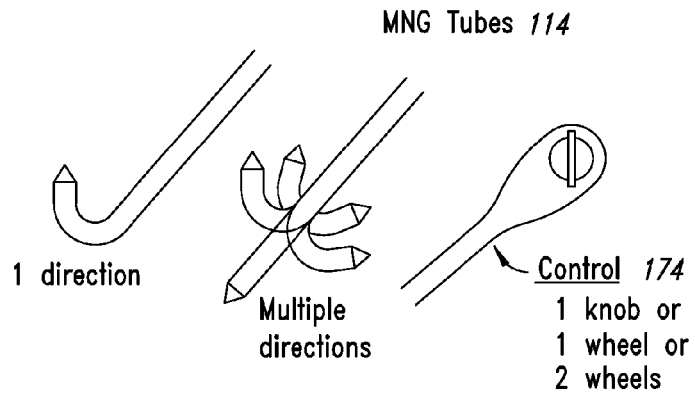
FIG. 52 shows bending the tip of the controllable magnetic nasogastric tube with a control handle; one direction may be all that is used as the torque stability makes the tip bending go in any direction according to an embodiment.

FIG. 52 shows additional features of a controllable magnetic nasogastric tube 114, for example, a control 174 for bending the tip in 1 to 4 directions to 90 degrees or 180 degrees. The control handle is formed on the proximal end, which remains outside the patient. In some embodiments, the control handle at the proximal end of the controllable magnetic nasogastric tube 114, which is outside the patient and manipulable by a medical practitioner, may have a visual and/or tactile queue to indicate the direction of the bend.

Figure 53:
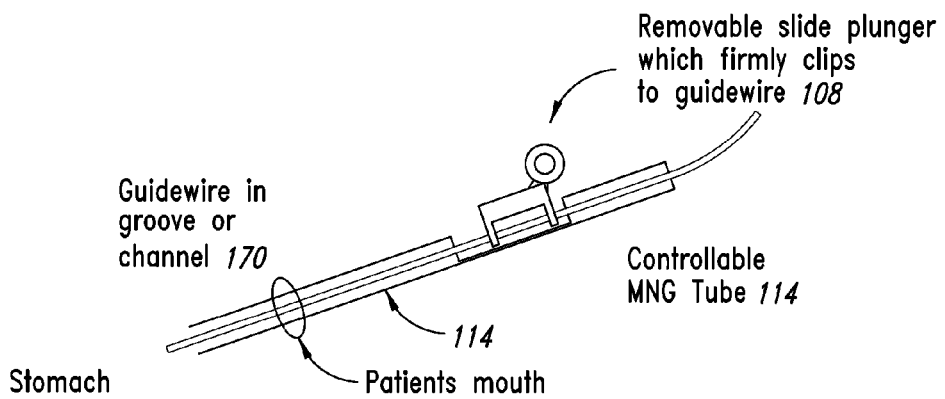
FIG. 53 shows a slide plunger attached to the guide wire for advancing a needle and the plunger can then be released according to an embodiment.

FIG. 53 shows additional features of a controllable magnetic nasogastric tube 114, for example, a slide plunger 176 which may attach to a guide wire 108 and be used to advance a needle 106 formed or attached on the tip of the guide wire 108 through the gastric and abdominal walls. The plunger 176 can then be released from the guide wire 108 as the controllable magnetic nasogastric tube 114 is removed.

The controllable magnetic nasogastric tube 114 may be removed after the wire 108 is secured outside the skin of the patient's abdomen. The guide wire 108 may be released by backing the controllable magnetic nasogastric tube 114 over the guide wire and out of the patient or by releasing the guide wire 108 from the channel or groove in the side of the controllable magnetic nasogastric tube and then backing out the controllable magnetic nasogastric tube.

Figure 54:
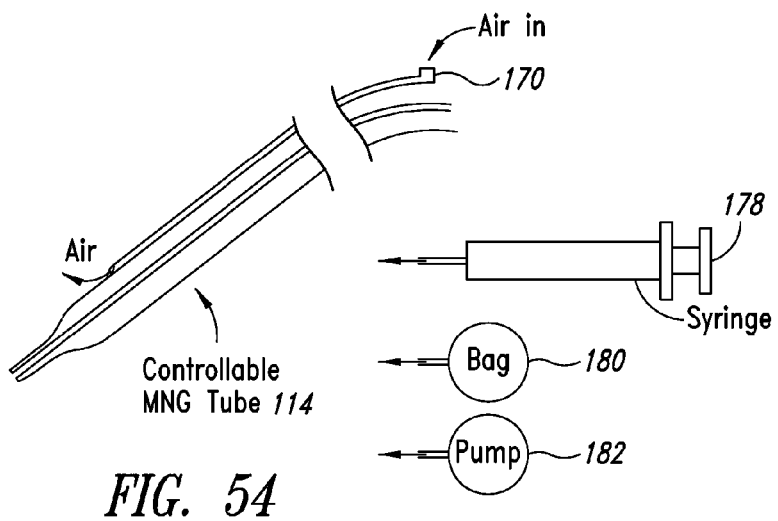
FIG. 54 shows an airport and an insufflation system according to an embodiment wherein a pump, syringe, or bag can be used to inflate the stomach, and a valve for preventing over distension may also be used.

The controllable magnetic nasogastric tube 114 may be formed with one or more devices or mechanisms to pass air or another medium of inflation into the patient. Several embodiments are shown in FIG. 54. For example, some embodiments of the controllable magnetic nasogastric tube 114 may have an air insufflation port 170. Some embodiments may have a valve for putting in air, and in some embodiments, a valve to prevent too much air or other medium and/or too much pressure in the site where the controllable magnetic nasogastric tube is placed. Other embodiments may use a simple bag 180 or a syringe 178 instead of a pump 182. Some embodiments may have measuring devices for gauging volume and/or pressure of the medium passed into the body through the controllable magnetic nasogastric tube 114.

Figure 55:
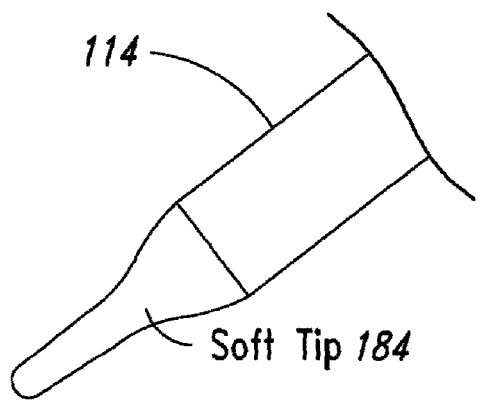
FIG. 55 shows a magnetic nasogastric tube with a soft tip for ease of introduction wherein the tip is softer and more flexible than is the shaft of the magnetic nasogastric tube according to an embodiment.

FIG. 55 shows an embodiment of a controllable magnetic nasogastric tube 114 having a smooth, gentle, soft tip 184 making this tube easy to introduce into a patient's body.

Figure 56:
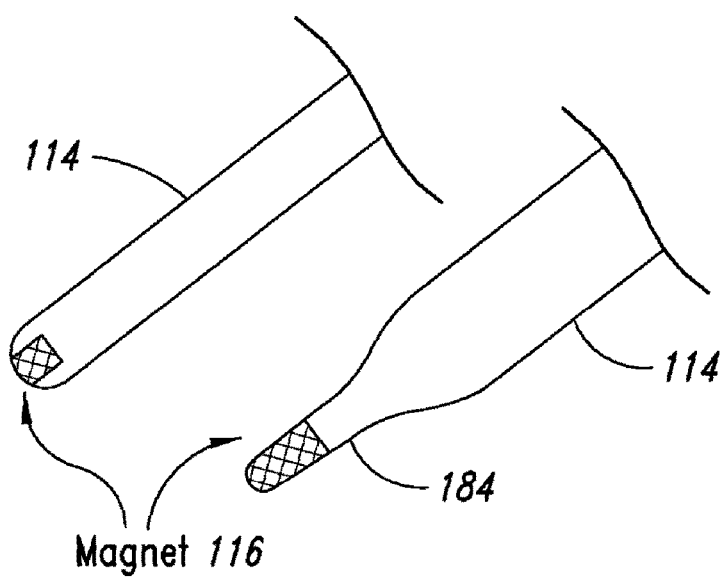
FIG. 56 shows a magnetic element in the tip of the magnetic nasogastric tube or in the tip of the soft flexible introducer according to an embodiment.

FIG. 56 shows a controllable magnetic nasogastric tube 114 having a magnetic element 116 on the tip; other embodiments may form a magnetic element in the tip of a soft rubber introducer, which may be passed via the magnetic nasogastric tube.

The multitude of features of the new controllable magnetic nasogastric tube described above provide many benefits that are not found in other devices or methods of performing percutaneous gastrostomy. For example, during a procedure, the controllable magnetic nasogastric tube has no need for light or vision in its distal end, and additionally, no need for a water source to wash the tip while the controllable magnetic nasogastric tube is inserted into a patient's body. Example embodiments of the new controllable magnetic nasogastric tube may be disposable or may be reusable. If the controllable magnetic nasogastric tube is reusable, it may be covered with a sheath that covers the channel into which the needle and guide wire are inserted. In these embodiments, the channel may be removed along with the sheath and both are replaced after each new procedure is performed on a patient so that each subsequent patient has a totally new or totally uncontaminated controllable magnetic nasogastric tube. In some embodiments, the sheath may be loose or tight, and if the sheath is tight, the technique for its use may involve a roll-up method of placement or an inflation method.

In some embodiments, a reusable controllable magnetic nasogastric tube may be formed from material that can be gas sterilized. Embodiments of the controllable magnetic nasogastric tube design are relatively simple compared to traditional endoscopic or similar devices and the new controllable magnetic nasogastric tube may be formed with few if any niches or inaccessible recesses. Accordingly, embodiments of the new controllable magnetic nasogastric tube are conducive to wash down and gas sterilization so that a sheath may not be necessary. In some embodiments, the design of the controllable magnetic nasogastric tube may permit the device to be sterilized in an autoclave, just like surgical instruments.

F. Additional Embodiments of Placing a Peg Tube

As described herein, embodiments having a magnet locator showing a substantially exact location of a magnet at a selected location on the stomach wall may now be used in medical practice. The distance from the skin to the magnet is determined with substantial precision. When used with endoscopic techniques, the placement of medical devices is improved. For example, if the distance from the skin to the magnet is excessive, an endoscopist may move the magnet onto another area of the gastric wall and use the external sensing device to find an area closer to the skin, which is better suited for placement of a PEG tube. Alternatively, the procedure may be considered too high risk because of excessive depth (e.g., possibly caused by adjacent liver or colon), and the procedure may be canceled because of the risk of hitting adjacent organs.

In another example, an indentation is no longer the only way that the endoscopist can determine whether a needle will enter the area selected. Instead, a ring of bright external lights on the sensing device may be seen inside the stomach via the endoscope. This will inform an endoscopist that if the guide channel is used, it will place the needle in the area selected.

In some embodiments, the lights on the sensing device outside the patient may be located on the tip of a cone or mound. In this way the cone is pressed against the abdomen very much like the standard method of using the finger of the person on the outside, then the lights are turned on and the substantially exact position of the planned insertion of the needle can be clearly seen from the inside by both the position of the indentation of the mound and the ring of lights. An examiner may still use the indentation but it is no longer the sole way to approximate where a needle will enter the gastric lumen.

In some medical procedures, a primary examiner and an assistant examiner work together to place a medical device in a living body. The use of the magnetic techniques described herein provide the assistant examiner with more knowledge about the desired location of the entrance to the gastric wall. The X and Y location of the magnet is clear (e.g., less than 1 mm precision), and the depth of the magnet is also clear, so the correct depth of needle is selected. This eliminates using more needle length than needed, especially if the target is missed. Accordingly, multiple excessively long insertions are no longer needed.

The magnet sensing system also has optional sensory aids (e.g., graphic indicators, sounds, etc), which inform the outside examiner that if a needle is inserted down the guide channel in the sensing device, it will go in the direction of the magnet. The sensory aids on the magnet sensing device may display the position and depth of the magnet, and may also provide a graphic guide path to inform the assistant examiner that if the needle is in the guide channel, the tip will go in the direction (in three dimensional space, using Cartesian coordinates X, Y and Z, for example) of the magnet. The length of needle needed is now known with substantial precision as well as the direction the needle should go to hit the magnet. The sensing device can be moved to place the guide path for the needle onto the magnet target.

The above embodiments relate to a new way to place a tube into the body, such as a PEG tube using magnetic and optical (light) guidance. A tube is placed inside the body with a magnet, localized where the tube and magnet are (e.g., with endoscopy, x-ray, ultrasound, etc.), then a magnet sensing device is used to locate the magnet inside the body and to advance a needle with a central wire, which supports placement of tubes for drainage, feeding, decompression, etc.

Additional embodiments are illustrated in FIGS. 57-66 and described in detail by way of the non-exhaustive and non-limiting examples herein. In particular, a method is shown for placing a tube from the inside by making the needle insertion from inside of the stomach. A PEG tube is used as an example, but small bowel tubes, colostomy tubes, etc., may also be possible with this method.

Figure 57:
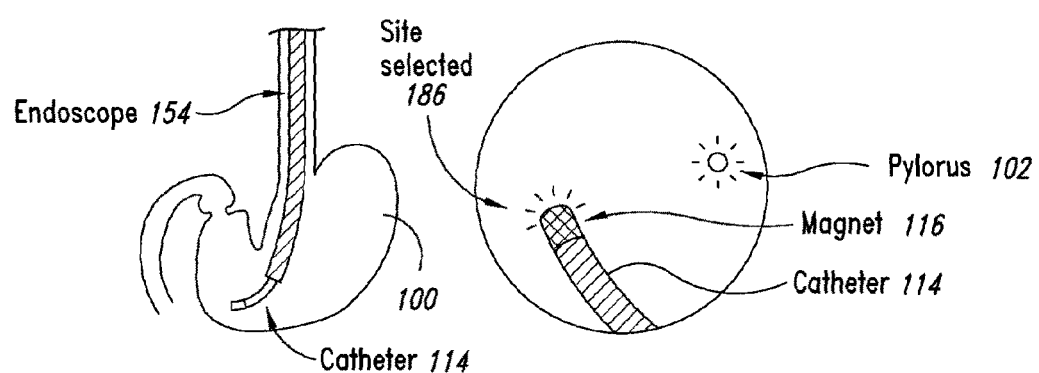
FIG. 57 shows an area of the gastric mucosa suited for PEG placement is identified and a catheter placed onto the area in accordance with one embodiment.

FIG. 57 shows an endoscope 154 placed into the stomach 100. An area is selected which the endoscopist believes would be suitable for the button seal on the PEG tube inside the stomach. A catheter 114 having a magnet 116 at its distal end is then advanced from the tip of the endoscope 154, under direct vision, to the area of the gastric mucosa selected for the PEG tube placement 186. In this embodiment, the endoscopist is careful to note the position of the pylorus 102 so as to avoid injury.

Figure 58:
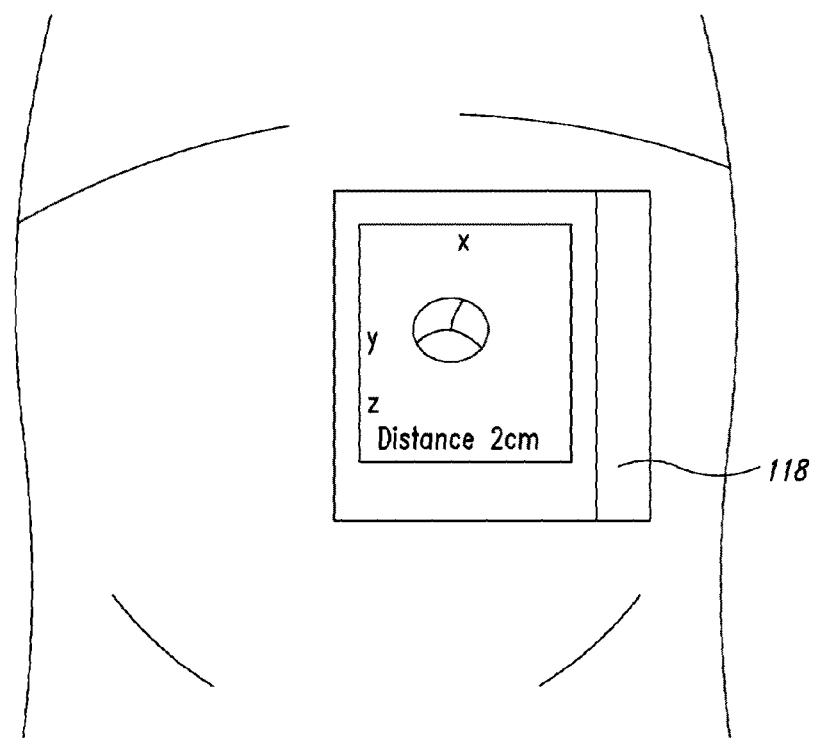
FIG. 58 shows a detector used to locate the position of a magnet on the tip of an endoscopic catheter in accordance with one embodiment.

FIG. 58 shows how an external magnet sensing device 118 may be used to locate the position of the magnet 116 from the anterior abdominal wall side. The device 118 locates the magnet 116 in three-dimensional space and determines the distance from the magnet to the skin surface. In one embodiment, the sensing device 118 of FIG. 58 can use similar techniques and components as otherwise described herein for locating and displaying the position, orientation, depth, etc., of a magnet 116 being sensed.

Figure 59:
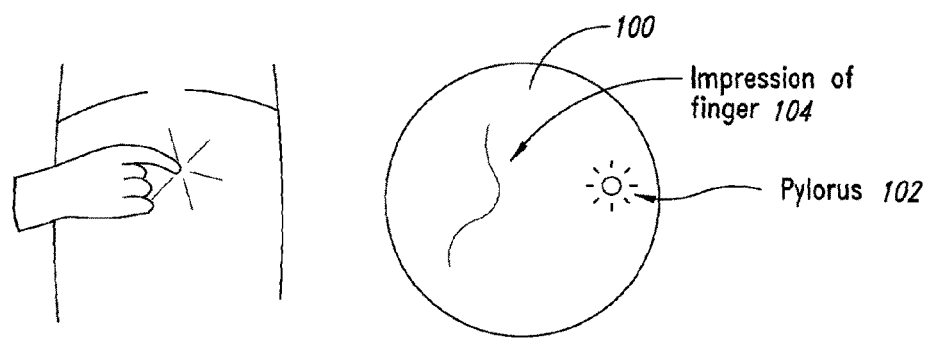
FIG. 59 shows palpation used to show that the location of an external site is close to the intraluminal site in accordance with one embodiment.

FIG. 59 shows how an assistant may then use light or a digital palpation 104 to confirm that the spot where the magnet is seen on the detector is below the rib cage and in a good position on the anterior abdominal wall for the PEG tube to exit the patient. Light from the inside (endoscope or bright light catheter) or from the outside (bright light such as an LED on the detector or as a free standing light) can confirm the reasonable position inside and outside for the PEG location.

FIGS. 60-63 show that when the site has been selected from the inside and outside, a catheter 140 held by an endoscope 154 may be used to push a needle 106 from the gastric lumen to the skin. This can be a very thin, fine needle or a thicker needle.

Figure 60:
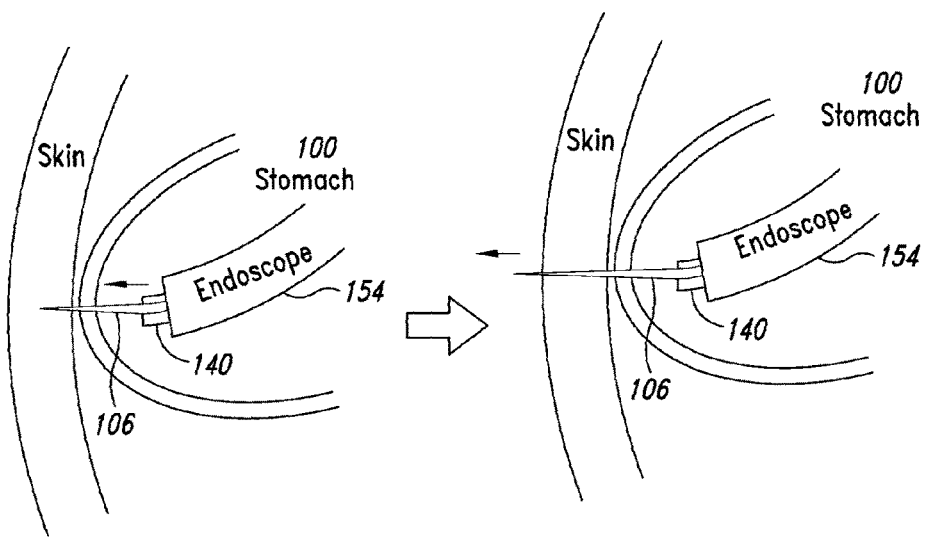
FIG. 60 shows a needle pushed through the gastric mucosa by advancing a catheter in an endoscope channel; this may be with the endoscope right against the gastric mucosa or with the endoscope back a distance from the mucosa in accordance with one embodiment.
Figure 61:
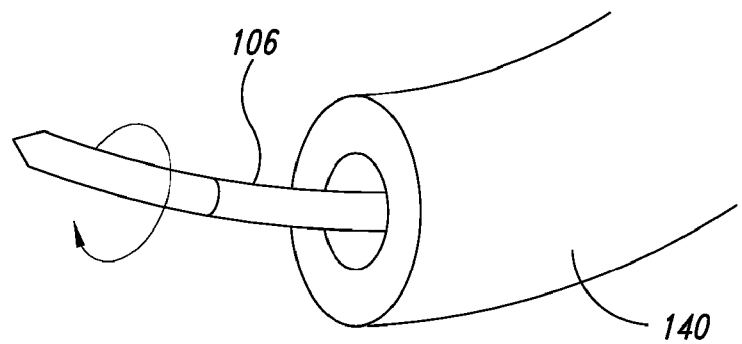
FIG. 61 shows that a needle may rotate to facilitate cutting as it exits the gastric lumen in accordance with one embodiment.
Figure 62:
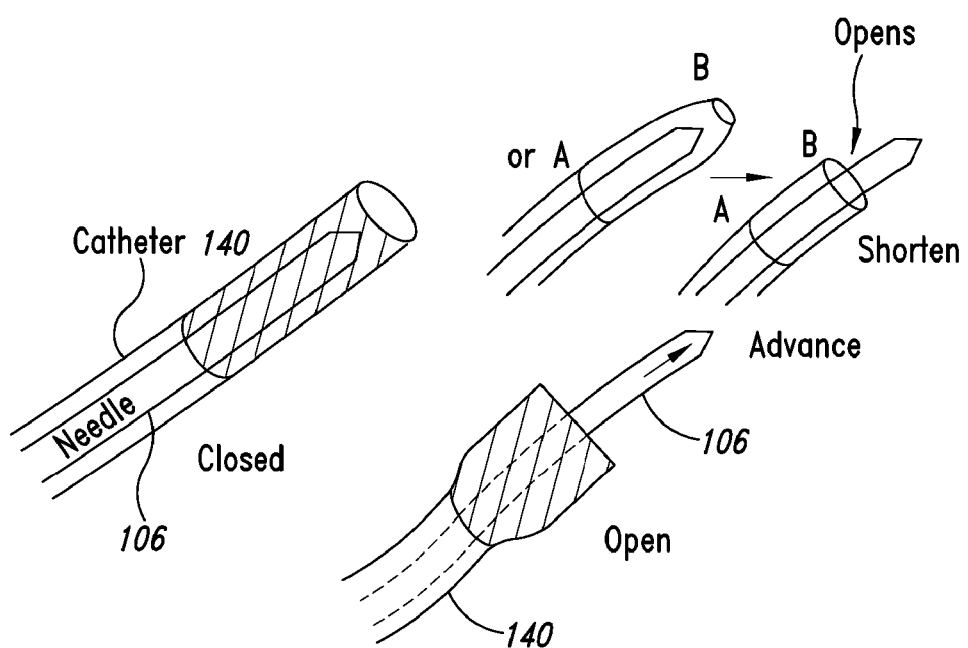
FIG. 62 shows a needle is enclosed inside the tip of a catheter until it is time to deploy; where the tip of the catheter is then pulled back (shortened) thereby stabilizing the catheter tip and widening the tip then allowing the tip of the needle catheter inside to exit in accordance with one embodiment.
Figure 63:
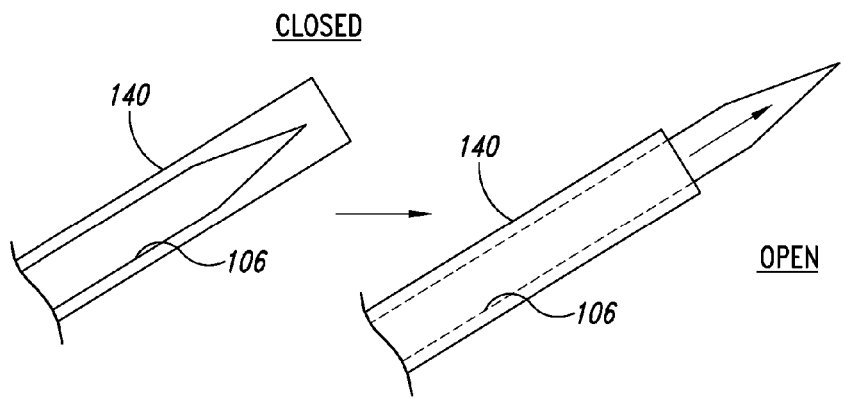
FIG. 63 shows a needle is inside an endoscopic catheter and exits when pushed at the proximal (outside) end of the catheter in accordance with one embodiment.

The needle 106 of FIG. 60 may be still except for advancing, or the needle may rotate, such as shown in FIG. 61. The needle 106 may advance from the endoscope 154, from the catheter 140, or from its own carrying overtube 188, such as shown in FIGS. 60-62.

The overtube 188 may be quiet or may have a function in which the tip retracts thereby stabilizing the tip so that the direction of the needle 106 can be controlled. This arrangement also covers the tip of the sharp catheter 140, preventing injury to the gastric or esophageal wall prior to the time when the operator wants to advance the needle 106. It will also protect the inside of the catheter 140 used to guide the needle tip into the stomach, for example the biopsy channel of the endoscope 154.

Figure 64:
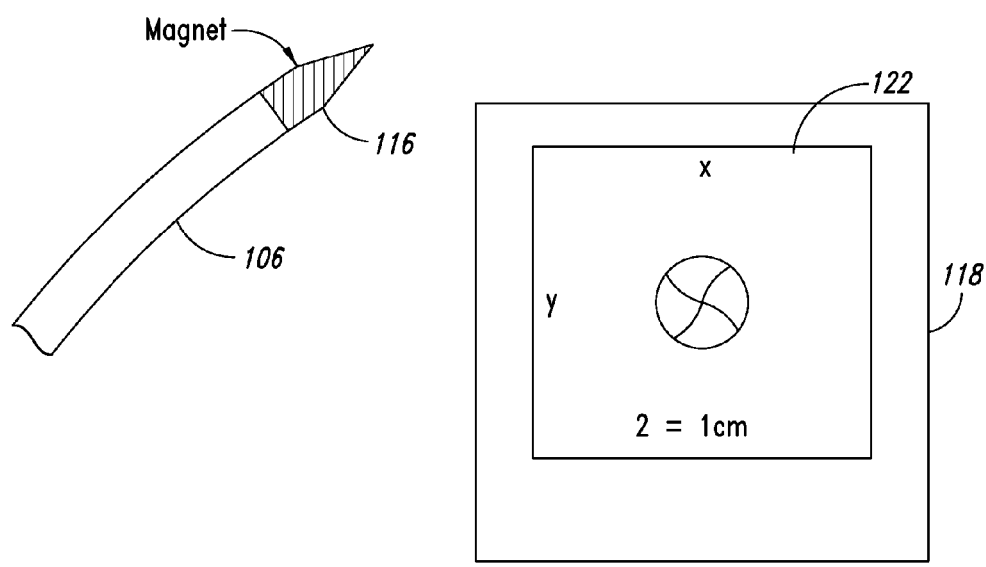
FIG. 64 shows how a magnet on the tip of a needle is seen in three-dimensional space by a detector enabling an examiner to see where the needle is moving as it is advanced from the gastric lumen to the outside in accordance with one embodiment.

FIG. 64 shows an embodiment wherein the tip of a cutting needle 106 (rotating or not) may be the magnet 116 itself. In this way the external magnet sensing device 118 may watch the path of the tip of the needle 106 as a three-dimensional projection on the screen 122.

In another embodiment, the magnet 116 may be located on a device/catheter separate from the needle. Thus, after a first magnetic nasogastric catheter 114 having the magnetic tip 116 is used to locate an insertion point in the gastric wall, the first catheter 114 is withdrawn and a second catheter 140 having the needle 106 at its tip is used to insert the needle 106 through the gastric wall. A double lumen catheter may allow for the magnet tip catheter to be inserted and, when position is selected, a needle tip catheter is extended out of the second channel.

Figure 65:
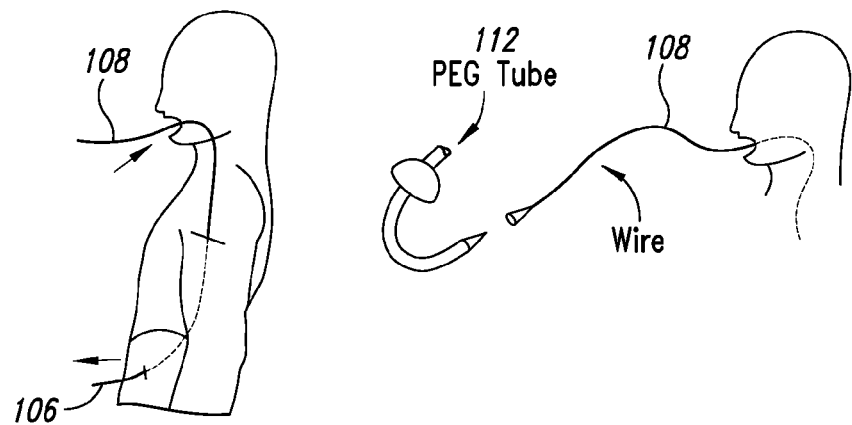
FIG. 65 shows a wire removed from an endoscope channel and attached to the tip of a PEG tube in accordance with one embodiment.

FIG. 65 shows that when the needle 106 exits the skin, it is pulled out manually and additional cable 108 is advanced through the patient's mouth. The proximal end (towards the patient's mouth) is then attached to the loop on the end of a PEG tube 112.

Figure 66:
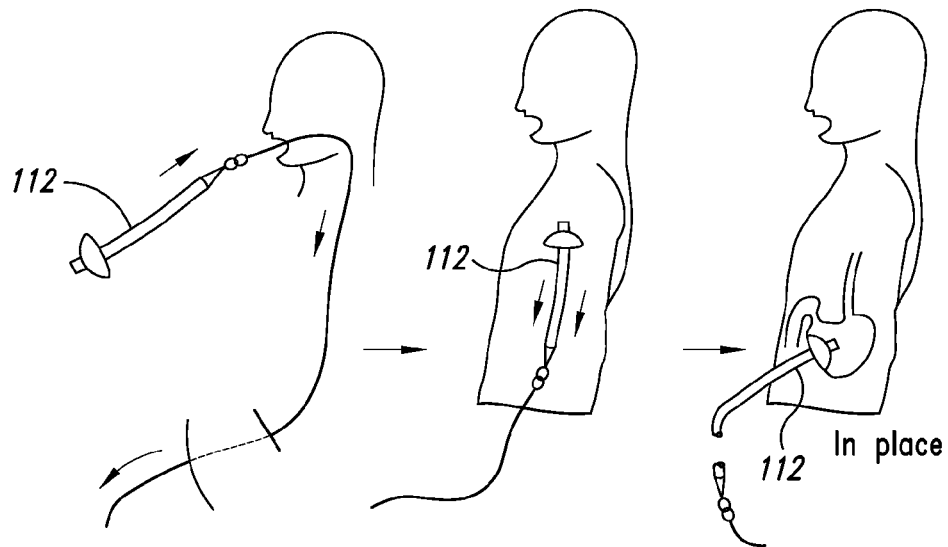
FIG. 66 shows a wire out of a patient's mouth attached to a PEG tube and pulled via the mouth into position on the skin of the anterior abdominal wall in accordance with one embodiment.

FIG. 66 shows that the PEG tube 112 is then pulled through the skin site until the pointed end emerges, and the PEG 112 is then placed into position with mild pressure.

One advantage of the approach proposed in the embodiments of FIGS. 57-66 is that it may be faster because the endoscopist does not have to grab the wire coming out of the needle in the gastric lumen. Another advantage is that the endoscopist knows with substantial precision where the PEG tube will be in the stomach, and the assistant knows with substantial precision where the PEG tube will be located on the anterior gastric wall. Additional advantages are improved accuracy, knowledge of the distance from the gastric wall to the skin, an ability to watch the progress of the needle tip, and fewer potential complications from having to grasp and hold the wire in the gastric lumen. Accordingly, this new procedure may be easier, faster, and safer than other approaches.

It is also clear from the description herein of non-limiting and non-exhaustive embodiments that a far safer method is provided for selecting a spot for PEG tube placement and insertion of a needle to accomplish the safe insertion, which reduces several risks to the patient, including, for example, not knowing where the selected site on the gastric wall contacts the skin on the outside, not knowing where the needle placed through the skin will enter into the stomach, and not knowing the direction that the needle should be directed to hit the selected gastric wall location. Another example is not knowing the distance from skin to the gastric wall, and therefore not knowing the length of needle to be inserted into the patient. Using excessive length may cause injury to adjacent organs, which would not be touched if excessive length were not used.

In addition to solutions and advantages already described, the embodiments can be more accurate, faster, have a higher success rate, and have a lower complication rate than with previous PEG placement procedures. The examiners know substantially where the needle must go to hit the target on the gastric wall. Increased precision in guidance increases the examiner's confidence and speeds the minimally invasive procedure. Further, less procedure time means more safety for the patient and reduced cost.

G. Additional Embodiments of Placing a Medical Devices

In addition to the examples for placing a PEG tube in a stomach, other medical devices can be placed in other locations of a living body. The target organ or space may be fairly small and it may be very difficult or impossible to safely place a needle into it from the outside of a patient through the skin. However, with the magnet locating system described herein, an external needle can be accurately and safely guided to the magnet already placed into the organ, and a connection created between the outside of the patient and the internal magnetic device. If the tip of the device is already in the space and must exit, an examiner can be reasonably sure that the tract or device will connect from the skin to the target space or organ.

The following list is a non-exhaustive, non-limiting list of applications where embodiments of the present invention may be employed for many organs for drainage, feeding, antibiotic infusion, etc. For example: Place PEG tube into the stomach; Place Percutaneous Endoscopic Jejunostomy (PEJ) tube into small bowel; Place tube into the colon (cecum, hep flex, splenic flex); Place tube into sigmoid colon; Place tube into renal calyx; Place tube into bladder; Place tube into abnormal collection of pus, fluid, cyst, etc.; Place tube into chest wall with air or fluid or purulence; Place tube into artery; Place tube into vein; Place tube into heart (RA, RV, LA, LV), which may be way to rapidly place pacer or defibrillation wire into RV or LV as one can be reasonably sure where the inside tip of the needle or wire is located, and if the magnet is in the RV and is advanced through the muscle to the skin, one can be reasonably sure it is in contact with the RV; Place tube from one vessel into another, such as artery to vein, artery to artery, and vein to vein; Place arteriovenous shunts; Place portocaval shunt; and Use to place diagnostic or therapeutic devices at laparoscopy or thoracoscopy. It is thus shown that the various embodiments provide a new, minimally invasive system, device, and method to place a medical device into a small or difficult to access space.

In one application, the techniques and devices described herein are useful for placing a medical device into an intestine, e.g., a small intestine. The small intestine in a body is typically loosely packed such that when pressure is applied, the intestine moves. Accordingly, penetrating the small intestine with a needle, catheter, or other medical device can be an elusive task for a medical practitioner.

Among the techniques described herein, additional embodiments are also useful for placing a medical device in the intestine. For example, a magnetic tipped wire may first be inserted into the intestine. Next, a magnetic detection sensor device may be used to detect, with substantial precision, the three dimensional location of the magnet. In one embodiment, the magnetic tipped wire has a particularly shaped magnet. Thus, when a magnet-tipped needle or other medical device is inserted through the body, via a guide channel in the magnetic detection sensor device, the attraction between the device and the magnetic tipped wire causes penetration of the intestine, regardless of the intestine's mobility.

In another embodiment, the magnetic tipped wire has additional structural elements to clamp the intestine in place. For example, an expandable tripod or other shaped structure may be released to sufficiently immobilize the intestine for penetration by the needle.

In still another embodiment, after the magnetic tipped wire is located with the magnetic detection sensor device, a clamping device is inserted through the magnetic detection sensor device and firmly clamps the intestine from the outside. Subsequently, the now immobilized intestine can be pierced with the needle or other medical device.

The systems, devices, and methods described herein in non-limiting and non-exhaustive embodiments for PEG placement may also be used in other embodiments for other diagnostic and therapeutic interventions. In addition, in each of the embodiments described above and below, it is recognized that several non-limiting and non-exhaustive variations are possible.

For example, one variation recognizes that some magnet sensing devices may not have lights. Other variations may have lights on a cone, small mound, hill, protrusion, or other suitably shaped device so pushes in can more readily be seen inside. In variations, the lights may be placed in a location or pattern suitable to a particular use. For example, the magnet sensing device may have lights in a ring so the endoscopist can see the light coming from the outside. In another example, the lights may be formed at the apex of a protrusion.

In another embodiment, the system may provide substantially precise localization of a desired target from the outside of the patient and then guide the diagnostic or therapeutic catheter to this location (e.g., using X, Y, Z Cartesian coordinates) with substantial precision. The system may also provide direction and a guide path displayed on the screen of the magnet sensing device.

Figure 67:
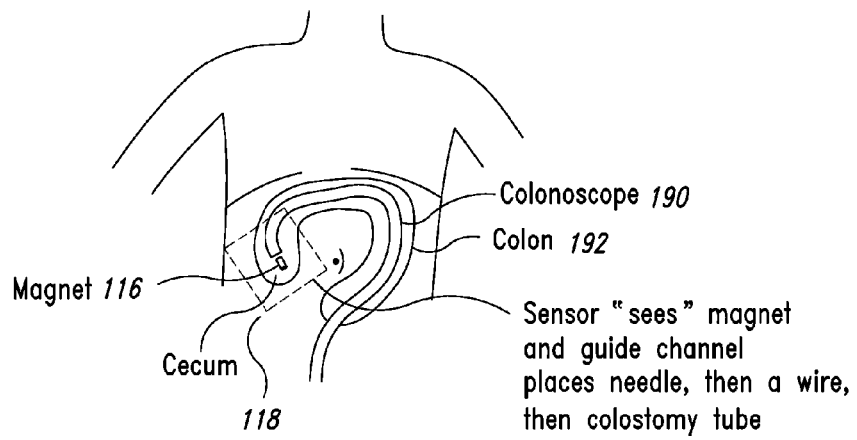
FIG. 67 shows a colonoscope placing a magnet, which is used to place a tube through the skin into the colon where desired in accordance with one embodiment.

FIG. 67 shows another embodiment using magnets and possibly lights, as in the PEG tube placement embodiment described above. In FIG. 66, a colostomy tube placement into the colon is shown. A colonoscope 190 is used to guide a device having a magnet 116 into the patient's colon 192. A magnetic sensing device 118 informs the practitioner of the location of the magnet from the outside.

Figure 68:
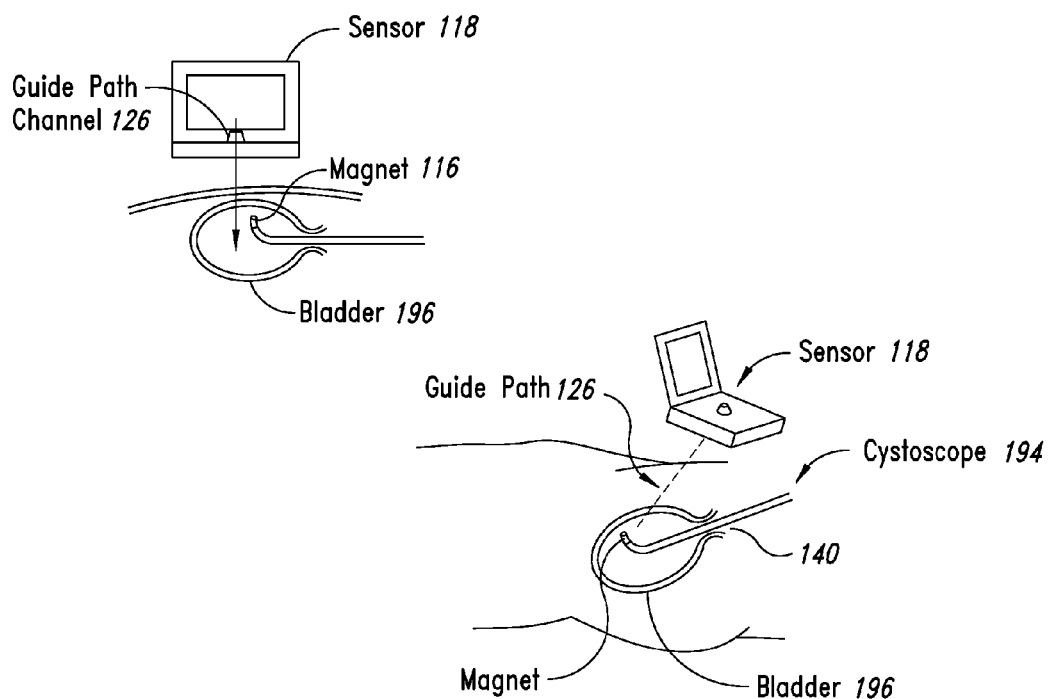
FIG. 68 shows a cystosomy tube placement into the bladder in accordance with one embodiment.

FIG. 68 shows another embodiment where a cystoscope 194 places a magnet 116 on the bladder wall, and the system is used to pass a catheter 140 through the skin into the bladder. A light may be used to predict where the catheter 140 will enter the bladder, and the cystoscope 194 image determines whether this will be an acceptable spot for the catheter 140.

Figure 69:
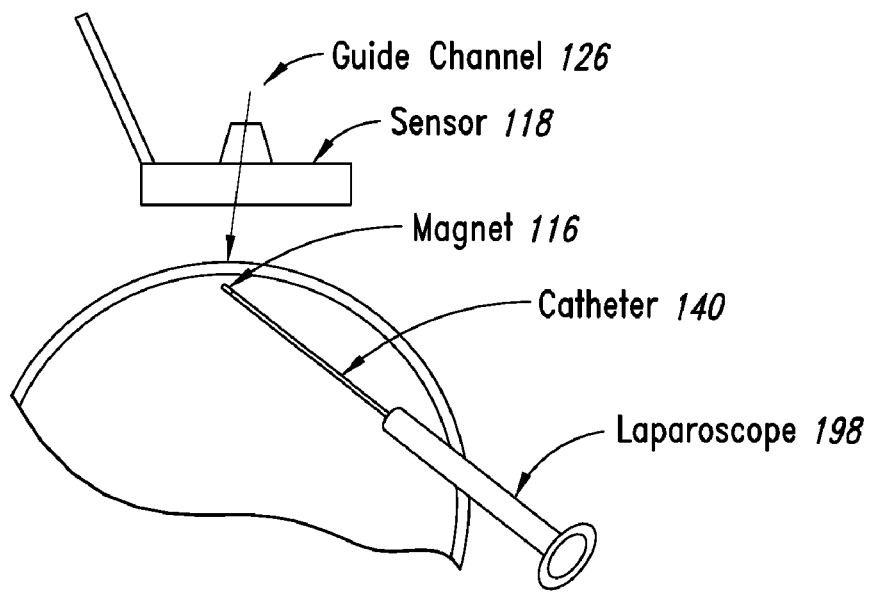
FIG. 69 shows a magnet directed laparoscopically to select a spot for a second penetration, and the area is detected from the outside using the sensing device in accordance with one embodiment.

FIG. 69 shows another embodiment where a laparoscope 198 is used to guide substantially precise entrance of additional catheters 140 and needles 106. At laparoscopy under direct vision, a target is selected for an additional tube 140. This spot may be one free of blood vessels to avoid bleeding, or free of adhesions to avoid complications with adhesions. A magnet 116 in a catheter 140 marks this spot in the patient's abdominal cavity. The external magnetic sensing device 118 locates the magnet (at the target) and gives a guide path 126 (direction and depth) as to how to get to the magnetic marker through the skin to the target.

Figure 70:
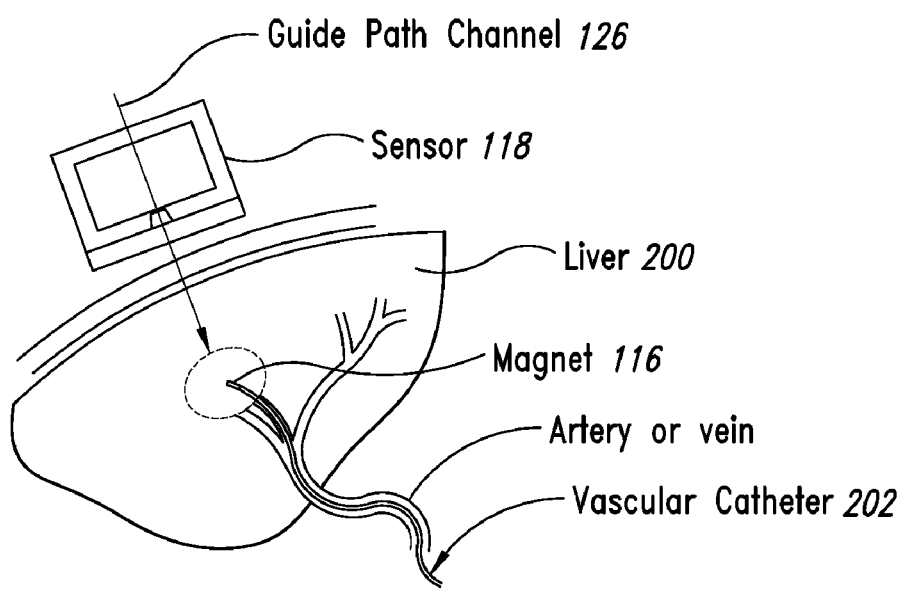
FIG. 70 shows a magnet passed intravascularly into an area using x-ray guidance, the magnet is located using a sensing device, and a diagnostic or therapeutic catheter is guided to the magnet placed at a target (e.g., tumor, etc.) in accordance with one embodiment.

FIG. 70 shows another embodiment where a magnet can be placed using a catheter under x-ray guidance. The magnet 116 can then be located and the system used to guide a percutaneous (e.g., vascular) catheter 202 to the spot. In this embodiment, a catheter 202 with a magnet 116 may be passed into an artery or vein (e.g., under x-ray, CT, MRI or ultrasound guidance) into the target lesion or organ.

Figure 71:
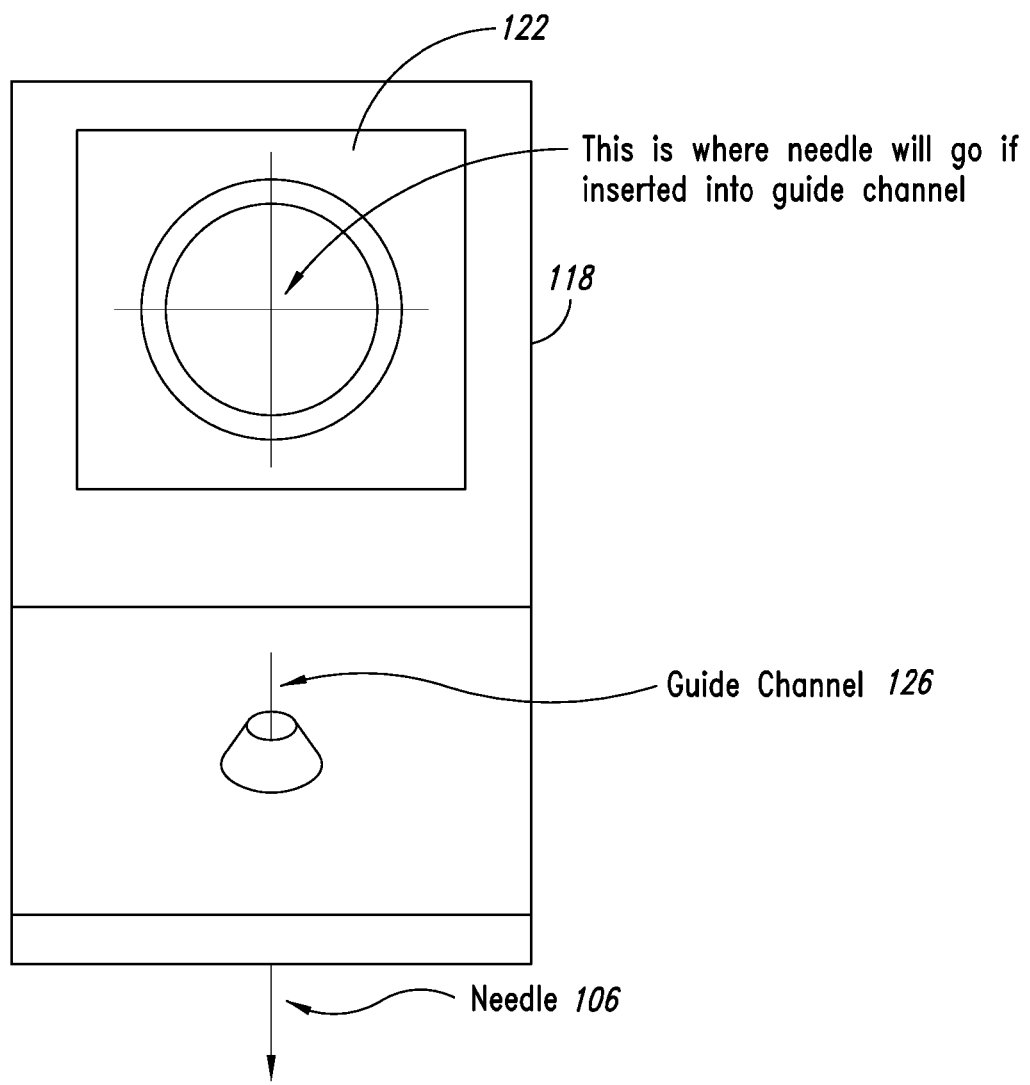
FIG. 71 shows a screen on a sensing device giving the substantially precise location of a magnet on a catheter, the depth, the direction and a guide path for a device when inserted into the guide channel of the sensing device in accordance with one embodiment.

FIG. 71 shows another embodiment where the substantially precise location of a magnet 116 is determined with a magnet sensing device 118, which also gives a substantially precise guide path 126 to pass a needle 106 or other catheter to the location of the magnet 116.

Figure 72:
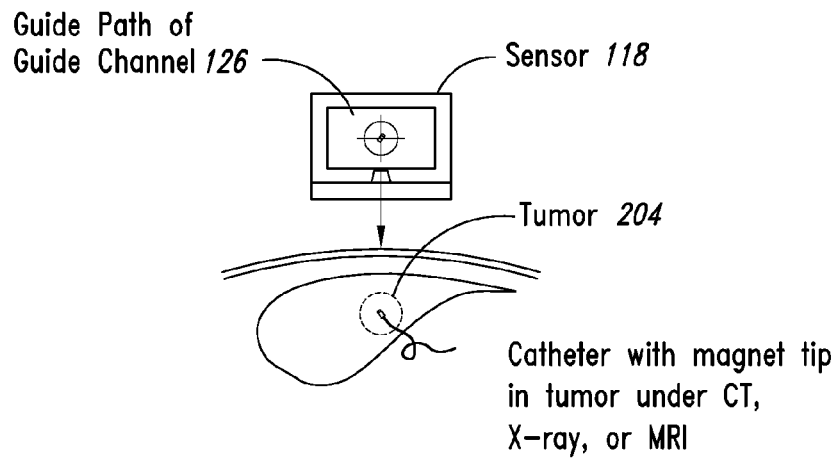
FIG. 72 shows a catheter placed under guidance (e.g., x-ray, CT, MRI or ultrasound) into a target tumor, and the detector detects a magnet and directs therapy to the target with a guide path, including depth in accordance with one embodiment.

For example if a tumor 204 in the liver is the problem, a magnetic tipped catheter can be inserted into a vein and then into the tumor 204 under x-ray guidance. The magnet sensing device 118 is then used to determine with substantial precision the location of the tumor 204 (with the magnetic tipped catheter in position). A magnet sensing device 118 and guide path 126 directs the examiner to the proper depth of the target and the X, Y, Z location, such as represented in FIG. 72.

A catheter may then be placed (e.g., through the skin or by endoscope or laparoscope) to get the catheter (or needle) to the magnet's location. Next, the magnet can be removed, and diagnosis is obtained via the catheter (e.g., aspiration, biopsy, brushing, etc.) or therapy is performed (e.g., heating, cooling, mechanical removal of tissue, RF ablation mono or bipolar, use of radiation catheter to perform RT, etc.). A catheter can also be placed and used for infusions of therapy such as cryotherapy, radiation therapy using a radiation emitting small catheter, infusion of chemotherapy, etc.

Accordingly, anywhere a catheter or needle can be placed; a magnet on a catheter can be inserted through a needle or catheter and then located to facilitate diagnosis and therapy. In a manner similar to that for placement of a PEG tube as described above, it may be possible to place a tube into a target using imaging guidance (x-ray, CT, MRI, ultrasound, PET, with or without contrast agents), with a magnet on the tip of the tube so its substantially precise location can be found from outside the body. Once the tube is placed, a second needle-tipped wire or catheter could be inserted through the first tube and advanced from the target to the outside of the patient or to an adjacent organ to facilitate positioning of a diagnostic or therapeutic device.

Figure 73:
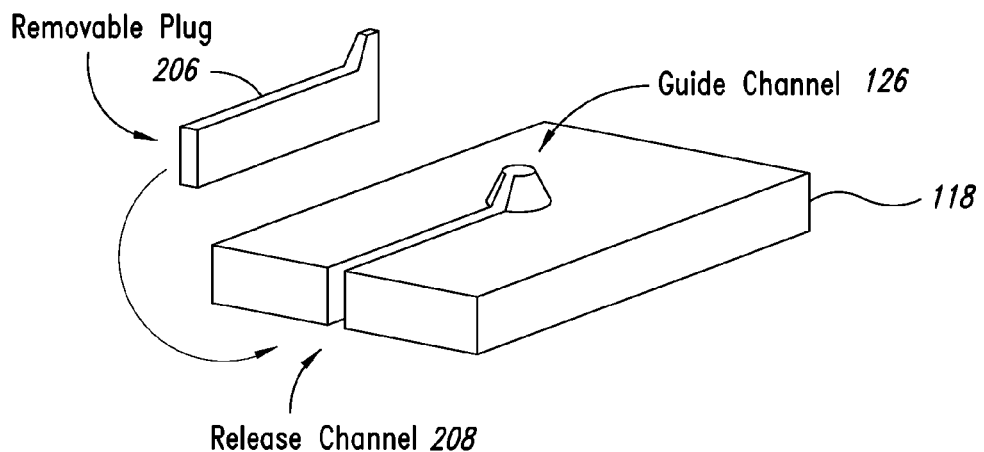
FIG. 73 shows a sensing device with a mechanism to release the needle or wire from the guide channel.

FIG. 73 shows another embodiment where a magnet sensing device 118 may be separated after a needle or wire is placed into the target. FIG. 73 shows one embodiment where a "release channel" 208 is used. The release channel 208 may be permanently open or may be temporarily closed during guidance and opened to release the magnet sensing device 118. For instance, a removable plug 206 may be provided to temporarily keep the release channel 208 closed during guidance, and then removed to release the magnet sensing device 118. In embodiments with a release mechanism, the reusable magnet sensing device 118 may still be covered by a sterile sheath 162.

From the foregoing it will be appreciated that, although specific embodiments have been described herein for purposes of illustration, various modifications may be made without deviating from the spirit and scope of the invention. Accordingly, the invention is not limited by this disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A medical device system, comprising:
a needle having a tip including a permanent magnet; and
a magnet sensing device including a plurality of sensors configured to detect a magnetic field of the permanent magnet, the magnet sensing device operable to localize a position of the permanent magnet relative to the magnet sensing device and to indicate a path of the needle on a display.

2. The system according to claim 1, wherein the path is a three-dimensional projection.

3. The system according to claim 1, wherein the magnet sensing device includes an audible indicator operable to provide a representation of the position of the permanent magnet relative to the magnet sensing device.

4. The system according to claim 1, further comprising a light emitting element coupled to the magnet sensing device.

5. The system according to claim 4, wherein the light emitting element is configured to provide visible light with sufficient brightness to penetrate tissue of a body such that the light is visible from a location inside the body.

6. The system according to claim 4, wherein the magnet sensing device and the light emitting element are in physically separable housings.

7. The system according to claim 4, wherein the light emitting element is positioned on a face of the magnet sensing device, the light emitting element operable to confirm the position of the permanent magnet relative to the magnet sensing device.

* * * * *